(12) United States Patent
Xu et al.

(10) Patent No.: US 11,981,936 B1
(45) Date of Patent: May 14, 2024

(54) TELA VARIANTS, COMPOSITIONS, AND METHODS

(71) Applicant: New England Biolabs, Inc., Ipswich, MA (US)

(72) Inventors: Shuang-Yong Xu, Lexington, MA (US); Andrew F. Gardner, Manchester, MA (US); Daniel Heiter, Topsfield, MA (US); Pei-Chung Hsieh, Topsfield, MA (US); Rebecca Kucera, Hamilton, MA (US); Juan Pan, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 18/478,512

(22) Filed: Sep. 29, 2023

(51) Int. Cl.
*C12N 9/12* (2006.01)
*C12N 9/02* (2006.01)
*C12P 19/34* (2006.01)
*C12Q 1/6844* (2018.01)

(52) U.S. Cl.
CPC ............ *C12N 9/0069* (2013.01); *C12P 19/34* (2013.01); *C12Q 1/6846* (2013.01); *C12Y 113/12007* (2013.01)

(58) Field of Classification Search
None
See application file for complete search history.

(56) References Cited

U.S. PATENT DOCUMENTS

| | | | |
|---|---|---|---|
| 6,875,748 B2 | 4/2005 | Manthorpe et al. | |
| 9,109,250 B2 | 9/2015 | Hill | |
| 9,499,847 B2 | 11/2016 | Porter et al. | |
| 10,501,782 B1 | 12/2019 | Porter et al. | |
| 11,149,302 B2 | 10/2021 | Rothwell et al. | |
| 2009/0011976 A1 | 1/2009 | Ludvigsen et al. | |

FOREIGN PATENT DOCUMENTS

| | | |
|---|---|---|
| WO | 2010086626 A1 | 8/2010 |
| WO | 2012017210 A1 | 2/2012 |
| WO | 2014020154 A1 | 2/2014 |
| WO | 2016132129 A1 | 8/2016 |

OTHER PUBLICATIONS

Genbank Accession No. WP_006312144.1, Jul. 5, 2004.
McGrath, et al., JBC, 298, 5, 101951, 2022.
McGrath, Thesis—TelA: An agrobacerial telomere resolvase, Feb. 2020.
Genbank Accession No. 4E0G_A, Mar. 3, 2012.
Aihara, et al., Mol Cell, 27(6):901-913, 2007.
Knott, et al., The Unusual Linear Plasmid Generating Systems of Prokaryotes (ch. 4 Bacteriophages Edited by Renos Savva) 2019.
Karda, et al., Gene Therapy, 26, 86-92, 2019.
Wingfield, Curr Protoc Protein Sci, 88: 6.14.1-6.14.3, 2017.
Forloni, et al., Cold Spring Harb Protoc, 2018.
Shi, et al., 2013, Plos Biology vol. 11 e1001472.
Huang, et al., 2012, J. Biol. Chem., 287, 25551-25563.

*Primary Examiner* — Richard G Hutson

(74) *Attorney, Agent, or Firm* — New England Biolabs, Inc

(57) ABSTRACT

The present disclosure relates, according to some embodiments, to telomere resolvases (e.g., TelA variants) having a turnover number over 1.

21 Claims, 25 Drawing Sheets
Specification includes a Sequence Listing.

SEQUENCE LISTING

```
Sequence total quantity: 24
SEQ ID NO: 1              moltype = AA  length = 337
FEATURE                   Location/Qualifiers
source                    1..337
                          mol_type = protein
                          organism = synthetic construct
VARIANT                   1
                          note = X may be T, M-T or M-H8-S-G-T
VARIANT                   97
                          note = X corresponds to D202 of wild type TelA and may be K
                          or R (or optionally any amino acid other than D or A (or
                          any amino acid other than D or A or P)
VARIANT                   98
                          note = X may be E or A
VARIANT                   337
                          note = X may be G or G-H6
SEQUENCE: 1
XGVATSIVEK IERAEFNTAG RKPTVLLRIA DFIAAMNGMD AKQDMQALWD AEIAIMNGRA    60
QTTIISYITK YRNAIREAFG DDHPMLKIAT GDAAMYXXAR RVKMEKIANK HGALITFENY   120
RQVLKICEDC LKSSDPLMIG IGLIGMTGRR PYEVFTQAEF SPAPYGKGVS KWSILFNGQA   180
KTKQGEGTKF GITYEIPVLT RSETVLAAYK RLRESGQGKL WHGMSIDDFS SETRLLLRDT   240
VFNLFEDVWP KEELPKPYGL RHLYAEVAYH NFAPPHVTKN SYFAAILGHN NNDLETSLSY   300
MTYTLPEDRD NALARLKRTN ERTLQQMATI APVSRKX                            337

SEQ ID NO: 2              moltype = AA  length = 338
FEATURE                   Location/Qualifiers
source                    1..338
                          mol_type = protein
                          organism = synthetic construct
SEQUENCE: 2
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYKEA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKG                           338

SEQ ID NO: 3              moltype = AA  length = 338
FEATURE                   Location/Qualifiers
source                    1..338
                          mol_type = protein
                          organism = synthetic construct
SEQUENCE: 3
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYKAA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKG                           338

SEQ ID NO: 4              moltype = AA  length = 338
FEATURE                   Location/Qualifiers
source                    1..338
                          mol_type = protein
                          organism = synthetic construct
SEQUENCE: 4
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYREA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKG                           338

SEQ ID NO: 5              moltype = AA  length = 338
FEATURE                   Location/Qualifiers
source                    1..338
                          mol_type = protein
                          organism = synthetic construct
SEQUENCE: 5
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYRAA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKG                           338

SEQ ID NO: 6              moltype = AA  length = 338
FEATURE                   Location/Qualifiers
```

```
source                  1..338
                        mol_type = protein
                        organism = synthetic construct
SEQUENCE: 6
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYDEA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKG                          338

SEQ ID NO: 7            moltype = AA  length = 348
FEATURE                 Location/Qualifiers
source                  1..348
                        mol_type = protein
                        organism = synthetic construct
SEQUENCE: 7
MHHHHHHHHS GTGVATSIVE KIERAEFNTA GRKPTVLLRI ADFIAAMNGM DAKQDMQALW    60
DAEIAIMNGR AQTTIISYIT KYRNAIREAF GDDHPMLKIA TGDAAMYKEA RRVKMEKIAN   120
KHGALITFEN YRQVLKICED CLKSSDPLMI GIGLIGMTGR RPYEVFTQAE FSPAPYGKGV   180
SKWSILFNGQ AKTKQGEGTK FGITYEIPVL TRSETVLAAY KRLRESGQGK LWHGMSIDDF   240
SSETRLLLRD TVFNLFEDVW PKEELPKPYG LRHLYAEVAY HNFAPPHVTK NSYFAAILGH   300
NNNDLETSLS YMTYTLPEDR DNALARLKRT NERTLQQMAT IAPVSRKG               348

SEQ ID NO: 8            moltype = AA  length = 348
FEATURE                 Location/Qualifiers
source                  1..348
                        mol_type = protein
                        organism = synthetic construct
SEQUENCE: 8
MHHHHHHHHS GTGVATSIVE KIERAEFNTA GRKPTVLLRI ADFIAAMNGM DAKQDMQALW    60
DAEIAIMNGR AQTTIISYIT KYRNAIREAF GDDHPMLKIA TGDAAMYREA RRVKMEKIAN   120
KHGALITFEN YRQVLKICED CLKSSDPLMI GIGLIGMTGR RPYEVFTQAE FSPAPYGKGV   180
SKWSILFNGQ AKTKQGEGTK FGITYEIPVL TRSETVLAAY KRLRESGQGK LWHGMSIDDF   240
SSETRLLLRD TVFNLFEDVW PKEELPKPYG LRHLYAEVAY HNFAPPHVTK NSYFAAILGH   300
NNNDLETSLS YMTYTLPEDR DNALARLKRT NERTLQQMAT IAPVSRKG               348

SEQ ID NO: 9            moltype = AA  length = 344
FEATURE                 Location/Qualifiers
source                  1..344
                        mol_type = protein
                        organism = synthetic construct
SEQUENCE: 9
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYKEA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKGHH HHHH                   344

SEQ ID NO: 10           moltype = AA  length = 344
FEATURE                 Location/Qualifiers
source                  1..344
                        mol_type = protein
                        organism = synthetic construct
SEQUENCE: 10
MTGVATSIVE KIERAEFNTA GRKPTVLLRI ADFIAAMNGM DAKQDMQALW DAEIAIMNGR    60
AQTTIISYIT KYRNAIREAF GDDHPMLKIA TGDAAMYREA RRVKMEKIAN KHGALITFEN   120
YRQVLKICED CLKSSDPLMI GIGLIGMTGR RPYEVFTQAE FSPAPYGKGV SKWSILFNGQ   180
AKTKQGEGTK FGITYEIPVL TRSETVLAAY KRLRESGQGK LWHGMSIDDF SSETRLLLRD   240
TVFNLFEDVW PKEELPKPYG LRHLYAEVAY HNFAPPHVTK NSYFAAILGH NNNDLETSLS   300
YMTYTLPEDR DNALARLKRT NERTLQQMAT IAPVSRKGHH HHHH                   344

SEQ ID NO: 11           moltype = AA  length = 442
FEATURE                 Location/Qualifiers
source                  1..442
                        mol_type = protein
                        organism = synthetic construct
SEQUENCE: 11
MLAAKRKTKT PVLVERIDQF VGQIKEAMKS DDASRNRKIR DLWDAEVRYH FDNGRTEKTL    60
ELYIMKYRNA LKAEFGPKST PLAICNMKKL RERLNTYIAR GDYPKTGVAT SIVEKIERAE   120
FNTAGRKPTV LLRIADFIAA MNGMDAKQDM QALWDAEIAI MNGRAQTTII SYITKYRNAI   180
REAFGDDHPM LKIATGDAAM YKEARRVKME KIANKHGALI TFENYRQVLK ICEDCLKSSD   240
PLMIGIGLIG MTGRRPYEVF TQAEFSPAPY GKGVSKWSIL FNGQAKTKQG EGTKFGITYE   300
IPVLTRSETV LAAYKRLRES GQGKLWHGMS IDDFSSETRL LLRDTVFNLF EDVWPKEELP   360
KPYGLRHLYA EVAYHNFAPP HVTKNSYFAA ILGHNNNDLE TSLSYMTYTL PEDRDNALAR   420
LKRTNERTLQ QMATIAPVSR KG                                           442

SEQ ID NO: 12           moltype = AA  length = 442
```

```
FEATURE                 Location/Qualifiers
source                  1..442
                        mol_type = protein
                        organism = synthetic construct
SEQUENCE: 12
MLAAKRKTKT PVLVERIDQF VGQIKEAMKS DDASRNRKIR DLWDAEVRYH FDNGRTEKTL    60
ELYIMKYRNA LKAEFGPKST PLAICNMKKL RERLNTYIAR GDYPKTGVAT SIVEKIERAE   120
FNTAGRKPTV LLRIADFIAA MNGMDAKQDM QALWDAEIAI MNGRAQTTII SYITKYRNAI   180
REAFGDDHPM LKIATGDAAM YREARRVKME KIANKHGALI TFENYRQVLK ICEDCLKSSD   240
PLMIGIGLIG MTGRRPYEVF TQAEFSPAPY GKGVSKWSIL FNGQAKTKQG EGTKFGITYE   300
IPVLTRSETV LAAYKRLRES GQGKLWHGMS IDDFSSETRL LLRDTVFNLF EDVWPKEELP   360
KPYGLRHLYA EVAYHNFAPP HVTKNSYFAA ILGHNNNDLE TSLSYMTYTL PEDRDNALAR   420
LKRTNERTLQ QMATIAPVSR KG                                            442

SEQ ID NO: 13           moltype = AA  length = 442
FEATURE                 Location/Qualifiers
source                  1..442
                        mol_type = protein
                        organism = synthetic construct
SEQUENCE: 13
MLAAKRKTKT PVLVERIDQF VGQIKEAMKS DDASRNRKIR DLWDAEVRYH FDNGRTEKTL    60
ELYIMKYRNA LKAEFGPKST PLAICNMKKL RERLNTYIAR GDYPKTGVAT SIVEKIERAE   120
FNTAGRKPTV LLRIADFIAA MNGMDAKQDM QALWDAEIAI MNGRAQTTII SYITKYRNAI   180
REAFGDDHPM LKIATGDAAM YDEARRVKME KIANKHGALI TFENYRQVLK ICEDCLKSSD   240
PLMIGIGLIG MTGRRPYEVF TQAEFSPAPY GKGVSKWSIL FNGQAKTKQG EGTKFGITYE   300
IPVLTRSETV LAAYKRLRES GQGKLWHGMS IDDFSSETRL LLRDTVFNLF EDVWPKEELP   360
KPYGLRHLYA EVAYHNFAPP HVTKNSYFAA ILGHNNNDLE TSLSYMTYTL PEDRDNALAR   420
LKRTNERTLQ QMATIAPVSR KG                                            442

SEQ ID NO: 14           moltype = AA  length = 11
FEATURE                 Location/Qualifiers
source                  1..11
                        mol_type = protein
                        organism = synthetic construct
SEQUENCE: 14
MHHHHHHHHS G                                                         11

SEQ ID NO: 15           moltype = AA  length = 6
FEATURE                 Location/Qualifiers
source                  1..6
                        mol_type = protein
                        organism = synthetic construct
SEQUENCE: 15
HHHHHH                                                                6

SEQ ID NO: 16           moltype = DNA  length = 26
FEATURE                 Location/Qualifiers
source                  1..26
                        mol_type = other DNA
                        organism = synthetic construct
SEQUENCE: 16
aataacaata tcatgatatt gttatt                                         26

SEQ ID NO: 17           moltype = DNA  length = 1092
FEATURE                 Location/Qualifiers
source                  1..1092
                        mol_type = other DNA
                        organism = synthetic construct
SEQUENCE: 17
gtttaacttt aagaaggaga tatacatatg accggcgtgg cgacgtctat cgtagagaaa    60
atcgagcgcg cggaatttaa cacggcggga cgtaagccta ctgtcctttt gcgtattgct   120
gacttcattg cagctatgaa tggtatggac gcgaagcaag atatgcaggc gctttgggat   180
gctgaaattg ccattatgaa tggtcgtgcc cagaccacta tcattagtta tatcacgaag   240
tatcgcaacg ccatccgcga agcgttcggt gacgaccacc ctatgttaaa gatcgccact   300
ggagatgccg caatgtatga cgaggctcgc cgtgtcaaga tggagaaaat tgctaataaa   360
catggagcac tgattacttt cgaaaattat cgtcaagtgt tgaaaatttg cgaggactgt   420
ctgaaatcat ctgacccgct tatgatcggg attggcctta ttggaatgac tggccgccgc   480
ccttacgagg tattcacaca ggcggagttc tcgccagcgc catatggcaa aggagtctcg   540
aagtggagta ttcttttcaa cggtcaggcc aagaccaaac aaggtgaggg tactaaattc   600
ggaatcacat atgagatccc agtactgact cgttctgaaa cagttttagc tgcatacaaa   660
cgtttgcgcg aatctggcca gggaaagtta tggcacggaa tgagtatcga tgatttctcg   720
agtgaaactc gccttttgtt acgcgatacc gtcttcaatc tgttcgaaga cgtctggcct   780
aaagaagaac ttccgaagcc gtatggtttg cgccacctgt acgcagaggt agcatatcat   840
aacttcgcgc cacctcacgt gactaagaat tcctacttt gggacataat                900
aataacgatt ggagacaag tctttcatat atgacctata cccttcctga ggaccgtgat   960
aatgccttag ctcgtttgaa gcgcactaac gaacgcacgt tgcaacagat ggcaactatc  1020
gccccggtga gccgcaaggg tcaccatcac catcaccatt gactcgaggg ctcttcctgc  1080
atcacgggag at                                                     1092
```

```
SEQ ID NO: 18              moltype = DNA   length = 57
FEATURE                    Location/Qualifiers
source                     1..57
                           mol_type = other DNA
                           organism = synthetic construct
variation                  28
                           note = N may be any of A, C, G, or T
variation                  29
                           note = N may be any of A, C, G, or T
variation                  30
                           note = B may be C, G, or T, but not A
SEQUENCE: 18
atcgccactg gagatgccgc aatgtatnnb gaggctcgcc gtgtcaagat ggagaaa      57

SEQ ID NO: 19              moltype = DNA   length = 57
FEATURE                    Location/Qualifiers
source                     1..57
                           mol_type = other DNA
                           organism = synthetic construct
variation                  28
                           note = V may be A, C, or G, but not T
variation                  29
                           note = N may be any of A, C, G, or T
variation                  30
                           note = N may be any of A, C, G, or T
SEQUENCE: 19
tttctccatc ttgacacggc gagcctcvnn atacattgcg gcatctccag tggcgat      57

SEQ ID NO: 20              moltype = DNA   length = 30
FEATURE                    Location/Qualifiers
source                     1..30
                           mol_type = other DNA
                           organism = synthetic construct
SEQUENCE: 20
gtttaacttt aagaaggaga tatacatatg                                    30

SEQ ID NO: 21              moltype = DNA   length = 57
FEATURE                    Location/Qualifiers
source                     1..57
                           mol_type = other DNA
                           organism = synthetic construct
SEQUENCE: 21
ctcgggtagg gcaactagtg catctccgca gatgcaggaa gagccctcga gtcaatg      57

SEQ ID NO: 22              moltype = DNA   length = 78
FEATURE                    Location/Qualifiers
source                     1..78
                           mol_type = other DNA
                           organism = synthetic construct
SEQUENCE: 22
cggccagtgg gatccaataa caatatcatg atattgttat tcgtacagga atccgtacct   60
cagactcgta tcttcacg                                                 78

SEQ ID NO: 23              moltype = AA    length = 348
FEATURE                    Location/Qualifiers
source                     1..348
                           mol_type = protein
                           organism = synthetic construct
SEQUENCE: 23
MHHHHHHHHS GTGVATSIVE KIERAEFNTA GRKPTVLLRI ADFIAAMNGM DAKQDMQALW    60
DAEIAIMNGR AQTTIISYIT KYRNAIREAF GDDHPMLKIA TGDAAMYDEA RRVKMEKIAN   120
KHGALITFEN YRQVLKICED CLKSSDPLMI GIGLIGMTGR RPYEVFTQAE FSPAPYGKGV   180
SKWSILFNGQ AKTKQGEGTK FGITYEIPVL TRSETVLAAY KRLRESGQGK LWHGMSIDDF   240
SSETRLLLRD TVFNLFEDVW PKEELPKPYG LRHLYAEVAY HNFAPPHVTK NSYFAAILGH   300
NNNDLETSLS YMTYTLPEDR DNALARLKRT NERTLQQMAT IAPVSRKG               348
```

-continued

```
SEQ ID NO: 24          moltype = AA  length = 442
FEATURE                Location/Qualifiers
source                 1..442
                       mol_type = protein
                       organism = synthetic construct
SEQUENCE: 24
MLAAKRKTKT PVLVERIDQF VGQIKEAMKS DDASRNRKIR DLWDAEVRYH FDNGRTEKTL   60
ELYIMKYRNA LKAEFGPKST PLAICNMKKL RERLNTYIAR GDYPKTGVAT SIVEKIERAE  120
FNTAGRKPTV LLRIADFIAA MNGMDAKQDM QALWDAEIAI MNGRAQTTII SYITKYRNAI  180
REAFGDDHPM LKIATGDAAM YAEARRVKME KIANKHGALI TFENYRQVLK ICEDCLKSSD  240
PLMIGIGLIG MTGRRPYEVF TQAEFSPAPY GKGVSKWSIL FNGQAKTKQG EGTKFGITYE  300
IPVLTRSETV LAAYKRLRES GQGKLWHGMS IDDFSSETRL LLRDTVFNLF EDVWPKEELP  360
KPYGLRHLYA EVAYHNFAPP HVTKNSYFAA ILGHNNNDLE TSLSYMTYTL PEDRDNALAR  420
LKRTNERTLQ QMATIAPVSR KG                                          442
```

US 11,981,936 B1

TELA VARIANTS, COMPOSITIONS, AND METHODS

SEQUENCE LISTING STATEMENT

This disclosure includes a Sequence Listing submitted electronically in .xml format under the file name "NEB-475.xml" created on Sep. 29, 2023, and having a size of 31.3 KB. This Sequence Listing is incorporated herein in its entirety by this reference.

BACKGROUND

Replication of linear chromosomes can be confounded by the difficulty of priming the lagging strand at each end. Some prokaryotes, including *Agrobacterium tumefaciens* and *Borrelia* species, have covalently closed telomeres, obviating this problem, but creating another challenge—division of replicated chromosomes into daughter cells. These hairpin telomeres allow replication to proceed, but result in a circular replication intermediate comprising the original chromosome and the replicated chromosome, the ends of which are joined at telomere junctions. A telomere resolvase separates these conjoined chromosomes for each to be properly segregated into daughter cells by a telomere resolvase. More specifically, these enzymes cleave the conjoined chromosomes at the telomere junctions and form hairpin telomeres on each chromosome's end. Unlike other cellular enzymes that may iteratively catalyze a reaction hundreds or thousands of times in a normal cell cycle, telomere resolvases are tightly regulated. Such regulation may limit the utility of these enzymes as molecular tools.

SUMMARY

Accordingly, needs have arisen for telomere resolvases with an activity profile that is more compatible for use as a molecular tool. For example, cells may regulate the activity of a wild-type telomere resolvase by producing the enzyme in a form that does not catalyze more than one reaction. An enzyme that does not turnover may serve the cell's goal of tight regulation of the reaction (avoiding potentially devastating consequences of more promiscuous chromosome cleavage), but such an enzyme may have limited use as a molecular tool in vitro. The present disclosure provides, in some embodiments, telomere resolvases (e.g., TelA variants) having a turnover number over 1.

According to some embodiments, a variant protelomerase (e.g., TelA) may comprise an amino acid sequence according to SEQ ID NO:1, capable of cleaving and rejoining a polynucleotide comprising a nucleotide sequence according to SEQ ID NO:16 and having a turnover number≥1.1, wherein the amino acid sequence has at least 95% (e.g., at least 97%, at least 98%, at least 99%) identity to SEQ ID NO:1 and has at least one (e.g., at least 2, at least 3, or all) of the following properties: (a) X1 is T, M-T or M-$H_8$-S-G-T; (b) X97 is K or R; (c) X98 is A; and (d) X337 is G or G-$H_6$, provided that if X1 is M-$H_8$-S-G-T, X337 is G and if X337 is G-$H_6$, X1 is T or M-T. A variant protelomerase (e.g., TelA) amino acid sequence may have at least one (e.g., at least 2, at least 3, or all) of the following additional properties: (e) Y96 is Y; (f) R100 is R; (g) R101 is R; and (h) K103 is K. A variant protelomerase (e.g., TelA) amino acid sequence, in some embodiments, may have all of the properties (e)-(h). According to some embodiments, a variant protelomerase (e.g., TelA) amino acid sequence may have both of the following properties: (a) X1 is T, M-T or M-$H_8$-S-G-T, and (b) X97 is K or R. According to some embodiments, a variant protelomerase (e.g., TelA) amino acid sequence may have all of the following properties: (a) X1 is M-T, (b) X97 is K or R, and (d) X337 is G. A variant protelomerase (e.g., TelA) amino acid sequence may have all of the following properties: (a) X1 is M-$H_8$-S-G-T, (b) X97 is K or R, and (d) X337 is G, in some embodiments. A variant protelomerase (e.g., TelA) amino acid sequence, in some embodiments, may have all of the following properties: (a) X1 is M-T, (b) X97 is K or R, and (d) X337 is G-$H_6$.

According to some embodiments, a variant protelomerase (e.g., TelA) may comprise an amino acid sequence according to SEQ ID NO:1, capable of cleaving and rejoining a polynucleotide comprising a nucleotide sequence according to SEQ ID NO:16 and having a turnover number≥1.1, wherein the amino acid sequence has at least 95% (e.g., at least 97%, at least 98%, at least 99%) identity to SEQ ID NO:1 and has at least one (e.g., at least 2, at least 3, or all) of the following properties: (a) the amino acid sequence comprises a T, M-T or M-$H_8$-S-G-T that corresponds to X1 of SEQ ID NO:1; (b) the amino acid sequence comprises a K or R that corresponds to X97 of SEQ ID NO:1; (c) the amino acid sequence comprises an A that corresponds to X98 of SEQ ID NO:1; and/or (d) the amino acid sequence comprises a G or G-$H_6$ that corresponds to X337 of SEQ ID NO:1, provided that if X1 is M-$H_8$-S-G-T, X337 is G and if X337 is G-$H_6$, X1 is T or M-T. A variant protelomerase (e.g., TelA) amino acid sequence may have at least one (e.g., at least 2, at least 3, or all) of the following additional properties: (e) the amino acid sequence comprises a Y that corresponds to Y96 of SEQ ID NO:1; (f) the amino acid sequence comprises a R that corresponds to R100 of SEQ ID NO:1; (g) the amino acid sequence comprises a R that corresponds to R101 of SEQ ID NO:1; and (h) the amino acid sequence comprises a K that corresponds to K103 of SEQ ID NO:1. A variant protelomerase (e.g., TelA) amino acid sequence, in some embodiments, may have all of the properties (e)-(h). According to some embodiments, a variant protelomerase (e.g., TelA) amino acid sequence may have both of the following properties: (a) the amino acid sequence comprises a T, M-T or M-$H_8$-S-G-T that corresponds to X1 of SEQ ID NO:1; and (b) the amino acid sequence comprises a K or R that corresponds to X97 of SEQ ID NO:1. According to some embodiments, a variant protelomerase (e.g., TelA) amino acid sequence may have all of the following properties: (a) X1 is M-T, (b) X97 is K or R, and (d) X337 is G. A variant protelomerase (e.g., TelA) amino acid sequence may have all of the following properties: (a) X1 is M-$H_8$-S-G-T, (b) X97 is K or R, and (d) X337 is G, in some embodiments. A variant protelomerase (e.g., TelA) amino acid sequence, in some embodiments, may have all of the following properties: (a) X1 is M-T, (b) X97 is K or R, and (d) X337 is G-$H_6$.

Compositions and kits are also provided (e.g., for cutting DNA to form ends and closing the ends), which may comprise, for example, any of the disclosed variant protelomerases (e.g., TelA variants). Compositions and kits optionally may further include one or more of a buffering agent (e.g., HEPES, MES, MOPS, TAPS, tricine, Tris, ACES, ADA, BES, Bicine, CAPS, carbonic acid/bicarbonic acid, CHES, citric acid, DIPSO, EPPS, histidine, MOPSO, phosphoric acid, PIPES, POPSO, TAPS, TAPSO, triethanolamine), an excipient, a salt, a protein, a stabilizer, a detergent, a polyanion (e.g., spermidine, spermine, putrescine, polyethylenimine, 1,4,7-triazacyclononane, cyclen, ethylenediamine, 1,3,5,-triazinane), a polynucleotide (e.g., a TelA substrate comprising at least one copy of SEQ ID NO:16), a cell, a biological fluid or secretion, an aptamer, a pH indicator, a crowding agent, a sugar, a starch, cellulose, a glass-forming agent, a lipid, an oil, aqueous media, and/or a support. For example, a composition or kit may include any of the disclosed variant protelomerases (e.g., TelA variants) and a buffer (e.g., a storage buffer or a reaction buffer). A composition or kit may include (may further include) a salt (e.g., wherein the salt comprises NaCl, MgCl$_2$, MnCl$_2$, CaCl$_2$, an amino acid salt or any combination thereof), a protein, a stabilizer, a detergent (e.g., wherein the detergent is selected from an ionic detergent, a non-ionic, and a zwitterionic detergent), a polyanion, a polynucleotide, a cell, a biological fluid or secretion, an aptamer, a pH indicator, a crowding agent, a sugar, a starch, cellulose, a glass-forming agent, a lipid, an oil, aqueous media, a support, or any combination thereof. A composition may comprise, in some embodiments, variant TelA DNA substrate and the variant TelA at a molar ratio of ≥2, ≥3, ≥4, ≥5, ≥6. A kit may comprise, for example, any of the disclosed variant protelomerases (e.g., TelA variants) and a buffer (e.g., a storage buffer or a reaction buffer) and the buffer are in separate containers. In some embodiments, a composition or kit may comprise a polynucleotide, wherein the polynucleotide is an adapter comprising the sequence of SEQ ID NO:16.

The present disclosure further relates to methods of forming closed DNA ends. For example, a method may comprise contacting any of the disclosed variant protelomerases (e.g., TelA variants) and a variant TelA DNA substrate (e.g., a circular DNA or a closed linear DNA) having a nucleotide sequence comprising at least one copy of SEQ ID NO:16 to produce TelA cleavage products. In some embodiments, the contacting further comprises contacting the variant TelA DNA substrate and the variant TelA at a molar ratio of ≥2, ≥3, ≥4, ≥5, ≥6. In some embodiments, the contacting further comprises contacting the variant TelA, the variant TelA DNA substrate, and a reaction buffer. According to some embodiments, TelA cleavage products may comprise linear DNA molecules, each with at least one closed end formed by the variant TelA. According to some embodiments, cleavage products may comprise cleaved DNA with newly closed ends and the variant TelA at a molar ratio of ≥2, ≥3, ≥4, ≥5, ≥6.

BRIEF DESCRIPTION OF THE FIGURES

FIG. 19A shows results of an example protelomerase activity assay for variant TelA in which molar ratios of substrate over the enzyme homodimer are shown in the figure legend. FIG. 19B shows the time-dependent hairpin product formation with 25 nM enzyme and 200 nM substrate for TelA wild-type (gray) and ΔN105/D97K variant (blue). The light gray area on the bottom represents product amount of a single-turnover reaction.

BRIEF DESCRIPTION OF THE SEQUENCES

Figure 1B:
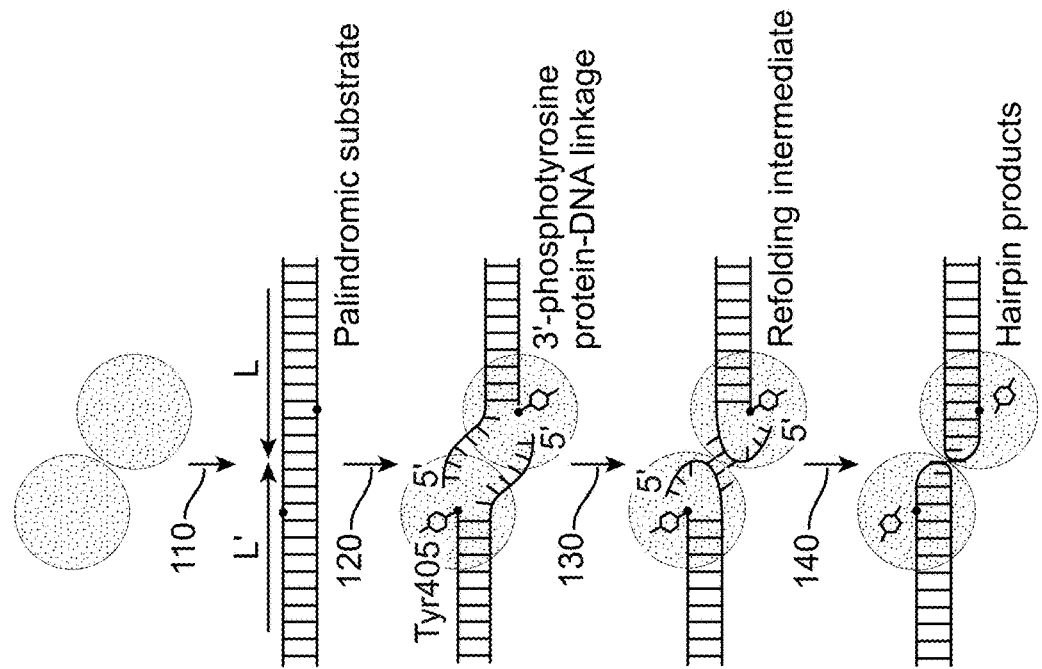
FIG. 1B illustrates the catalytic mechanism of an example telomere resolvase in which two molecules of the enzyme (circles) bind a palindromic target site (originally 50 bp, minimally ~26 bp) on a linear DNA, breaking the phosphate backbone of each strand to form a double-strand break across the palindromic target site with each side of the break having a 3'-phosphotyrosine-DNA linkage and a free 5' overhang. The enzyme facilitates formation of a refolding intermediate on each side of the break in which the free 5' overhang is brought near the 3'-phosphotyrosine-DNA linkage. The respective 5' and 3' ends are then ligated to form an intramolecular hairpin and the tyrosine residue is released.

Some embodiments of this disclosure relate to the following provided sequences of example polynucleotides and/or example polypeptides.

```
SEQ ID NO: 1 is an example sequence of TelA variants, wherein X1 may be T, M-T
or M-H8-S-G-T, X97 corresponds to D202 of wild type TelA and may be K or R (or
optionally any amino acid other than D or A (or any amino acid other than D or
A or P)), X98 may be E or A, and X337 may be G or G-H6.
XGVATSIVEKIERAEFNTAGRKPTVLLRIADFIAAMNGMDAKQDMQALWDAEIAIMNGRAQTTIISYITKYRNAIREAF
GDDHPMLKIATGDAAMYXXARRVKMEKIANKHGALITFENYRQVLKICEDCLKSSDPLMIGIGLIGMTGRRPYEVFTQA
EFSPAPYGKGVSKWSILFNGQAKTKQGEGTKFGITYEIPVLTRSETVLAAYKRLRESGQGKLWHGMSIDDFSSETRLLL
RDTVFNLFEDVWPKEELPKPYGLRHLYAEVAYHNFAPPHVTKNSYFAAILGHNNNDLETSLSYMTYTLPEDRDNALARL
KRTNERTLQQMATIAPVSRKX SEQ ID NO: 2 is an example of a variant TelA of SEQ ID NO: 1, wherein X1 is MT.
This sequence may be referred to as "ΔN105/D97K". In some embodiments,
optionally M1 may be M-H8-SG or G337 may be G-H6.
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYKEARRVKMEKIANKHGALITFENYRQVLKICEDCLKSSDPLMIGIGLIGMTGRRPYEVETQ
AEFSPAPYGKGVSKWSILFNGQAKTKQGEGTKFGITYEIPVLTRSETVLAAYKRLRESGQGKLWHGMSIDDFSSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKG SEQ ID NO: 3 is an example of a variant TelA of SEQ ID NO: 1, wherein X1 is MT,
K97 constitutes a substitution at the position corresponding to D202 of wild
type TelA, and A98 constitutes a substitution at the position corresponding to
E203 of wild type TelA. This sequence may be referred to as "ΔN105/D97K/E98A".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYKAARRVKMEKIANKHGALITFENYRQVLKICEDCLKSSDPLMIGIGLIGMTGRRPYEVFTQ
```

-continued

AEFSPAPYGKGVSKWSILFNGQAKTKQGEGTKFGITYEIPVLTRSETVLAAYKRLRESGQGKLWHGMSIDDFSSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKG

SEQ ID NO: 4 is an example of a variant TelA of SEQ ID NO: 1, wherein X1 is MT
and R97 constitutes a substitution at the position corresponding to D202 of
wild type TelA. This sequence may be referred to as "ΔN105/D97R".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYREARRVKMEKIANKHGALITFENYRQVLKICEDCLKSSDPLMIGIGLIGMTGRRPYEVFTQ
AEFSPAPYGKGVSKWSILFNGQAKTKQGEGTKFGITYEIPVLTRSETVLAAYKRLRESGQGKLWHGMSIDDFSSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKG SEQ ID NO: 5 is an example of a variant TelA of SEQ ID NO: 1, wherein X1 is MT,
R97 constitutes a substitution at the position corresponding to D202 of wild
type TelA, and A98 constitutes a substitution at the position corresponding to
E203 of wild type TelA. This sequence may be referred to as "ΔN105/D97R/E98A".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYRAARRVKMEKIANKHGALITFENYRQVLKICEDCLKSSDPLMIGIGLIGMTGRRPYEVETQ
AEFSPAPYGKGVSKWSILFNGQAKTKQGEGTKFGITYEIPVLTRSETVLAAYKRLRESGQGKLWHGMSIDDFSSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKG SEQ ID NO: 6 is an example of a variant TelA of SEQ ID NO: 1, wherein X1 is MT.
This sequence may be referred to as "ΔN105/D97".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYDEARRVKMEKIANKHGALITFENYRQVLKICEDCLKSSDPLMIGIGLIGMTGRRPYEVFTQ
AEFSPAPYGKGVSKWSILFNGQAKTKQGEGTKFGITYEIPVLTRSETVLAAYKRLRESGQGKLWHGMSIDDESSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKG SEQ ID NO: 7 is an example of a variant TelA of SEQ ID NO: 1, wherein X1 is
M(H)$_8$SGT. This sequence may be referred to as "N-terminally His-tagged
ΔN105/D97K" or simply as "ΔN105/D97K"
MHHHHHHHHSGTGVATSIVEKIERAEFNTAGRKPTVLLRIADFIAAMNGMDAKQDMQALWDAEIAIMNGRAQTTIISYI
TKYRNAIREAFGDDHPMLKIATGDAAMYKEARRVKMEKIANKHGALITFENYRQVLKICEDCLKSSDPLMIGIGLIGMT
GRRPYEVFTQAEFSPAPYGKGVSKWSILFNGQAKTKQGEGTKFGITYEIPVLTRSETVLAAYKRLRESGQGKLWHGMSI
DDFSSETRLLLRDTVFNLFEDVWPKEELPKPYGLRHLYAEVAYHNFAPPHVTKNSYFAAILGHNNNDLETSLSYMTYTL
PEDRDNALARLKRTNERTLQQMATIAPVSRKG SEQ ID NO: 8 is an example of a variant TelA of SEQ ID NO: 1, wherein X1 is
M(H)$_8$SGT. This sequence may be referred to as "N-terminally His-tagged
ΔN105/D97R" or simply as "ΔN105/D97R".
MHHHHHHHHSGTGVATSIVEKIERAEFNTAGRKPTVLLRIADFIAAMNGMDAKQDMQALWDAEIAIMNGRAQTTIISYI
TKYRNAIREAFGDDHPMLKIATGDAAMYREARRVKMEKIANKHGALITFENYRQVLKICEDCLKSSDPLMIGIGLIGMT
GRRPYEVFTQAEFSPAPYGKGVSKWSILFNGQAKTKQGEGTKFGITYEIPVLTRSETVLAAYKRLRESGQGKLWHGMSI
DDFSSETRLLLRDTVFNLFEDVWPKEELPKPYGLRHLYAEVAYHNFAPPHVTKNSYFAAILGHNNNDLETSLSYMTYTL
PEDRDNALARLKRTNERTLQQMATIAPVSRKG SEQ ID NO: 9 is an example of a variant TelA of SEQ ID NO: 1, wherein X337 is
G(H)$_6$. This sequence may be referred to as "C-terminally His-tagged ΔN105/D97K"
so simply "ΔN105/D97K".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYKEARRVKMEKIANKHGALITFENYRQVLKICEDCLKSSDPLMIGIGLIGMTGRRPYEVFTQ
AEFSPAPYGKGVSKWSILFNGQAKTKQGEGTKFGITYEIPVLTRSETVLAAYKRLRESGQGKLWHGMSIDDESSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKGHHHHHH SEQ ID NO: 10 is an example of a variant TelA of SEQ ID NO: 1, wherein X337 is
G(H)$_6$. This sequence may be referred to as "C-terminally His-tagged ΔN105/D97R"
so simply "ΔN105/D97R".
MTGVATSIVEKIERAEFNTAGRKPTVLLRIADFIAAMNGMDAKQDMQALWDAEIAIMNGRAQTTIISYITKYRNAIREA
FGDDHPMLKIATGDAAMYREARRVKMEKIANKHGALITFENYRQVLKICEDCLKSSDPLMIGIGLIGMTGRRPYEVFTQ
AEFSPAPYGKGVSKWSILFNGQAKTKQGEGTKFGITYEIPVLTRSETVLAAYKRLRESGQGKLWHGMSIDDESSETRLL
LRDTVFNLFEDVWPKEELPKPYGLRHLYAEVAYHNFAPPHVTKNSYFAAILGHNNNDLETSLSYMTYTLPEDRDNALAR
LKRTNERTLQQMATIAPVSRKGHHHHHH SEQ ID NO: 11 is an example variant TelA having a D202K substitution. This
sequence may be referred to as "D202K". In some embodiments, optionally M1 may
be M-H$_8$-SG or G442 may be G-H$_6$.
MLAAKRKTKTPVLVERIDQFVGQIKEAMKSDDASRNRKIRDLWDAEVRYHFDNGRTEKTLELYIMKYRNALKAEFGPKS
TPLAICNMKKLRERLNTYIARGDYPKTGVATSIVEKIERAEFNTAGRKPTVLLRIADFIAAMNGMDAKQDMQALWDAEI
AIMNGRAQTTIISYITKYRNAIREAFGDDHPMLKIATGDAAMYKEARRVKMEKIANKHGALITFENYRQVLKICEDCLK
SSDPLMIGIGLIGMTGRRPYEVFTQAEFSPAPYGKGVSKWSILFNGQAKTKQGEGTKFGITYEIPVLTRSETVLAAYKR
LRESGQGKLWHGMSIDDFSSETRLLLRDTVFNLFEDVWPKEELPKPYGLRHLYAEVAYHNFAPPHVTKNSYFAAILGHN
NNDLETSLSYMTYTLPEDRDNALARLKRTNERTLQQMATIAPVSRKG -continued SEQ ID NO: 12 is an example variant TelA having a D202R substitution. This
sequence may be referred to as "D202R". In some embodiments, optionally MI may
be M-H$_8$-SG or G442 may be G-H$_6$.
MLAAKRKTKTPVLVERIDQFVGQIKEAMKSDDASRNRKIRDLWDAEVRYHFDNGRTEKTLELYIMKYRNALKAEFGPKS
TPLAICNMKKLRERLNTYIARGDYPKTGVATSIVEKIERAEFNTAGRKPTVLLRIADFIAAMNGMDAKQDMQALWDAEI
AIMNGRAQTTIISYITKYRNAIREAFGDDHPMLKIATGDAAMYREARRVKMEKIANKHGALITFENYRQVLKICEDCLK
SSDPLMIGIGLIGMTGRRPYEVFTQAEFSPAPYGKGVSKWSILFNGQAKTKQGEGTKFGITYEIPVLTRSETVLAAYKR
LRESGQGKLWHGMSIDDFSSETRLLLRDTVFNLFEDVWPKEELPKPYGLRHLYAEVAYHNFAPPHVTKNSYFAAILGHN
NNDLETSLSYMTYTLPEDRDNALARLKRTNERTLQQMATIAPVSRKG SEQ ID NO: 13 is wild type TelA (WP_006312144.1)
MLAAKRKTKTPVLVERIDQFVGQIKEAMKSDDASRNRKIRDLWDAEVRYHFDNGRTEKTLELYIMKYRNALKAEFGPKS
TPLAICNMKKLRERLNTYIARGDYPKTGVATSIVEKIERAEFNTAGRKPTVLLRIADFIAAMNGMDAKQDMQALWDAEI
AIMNGRAQTTIISYITKYRNAIREAFGDDHPMLKIATGDAAMYDEARRVKMEKIANKHGALITFENYRQVLKICEDCLK
SSDPLMIGIGLIGMTGRRPYEVFTQAEFSPAPYGKGVSKWSILFNGQAKTKQGEGTKFGITYEIPVLTRSETVLAAYKR
LRESGQGKLWHGMSIDDFSSETRLLLRDTVFNLFEDVWPKEELPKPYGLRHLYAEVAYHNFAPPHVTKNSYFAAILGHN
NNDLETSLSYMTYTLPEDRDNALARLKRTNERTLQQMATIAPVSRKG SEQ ID NO: 14 is an example of an optional N-terminal His tag.
MHHHHHHHHSG SEQ ID NO: 15 is an example of an optional C-terminal His tag.
HHHHHH SEQ ID NO: 16 is an example TelA recognition sequence comprising a 13bp
inverted repeat. Cleavage occurs between A10 and T11.
AATAACAATATCATGATATTGTTATT SEQ ID NO: 17 is an example coding sequence for a variant TelA (SEQ ID NO: 6
comprising a C-terminal His tag), wherein lower case sequences (positions 1-27
and 1063-1092) are vector sequences and NdeI and XhoI sites flank the coding
sequence (28-1062).
gtttaactttaagaaggagatatacatATGACCGGCGTGGCGACGTCTATCGTAGAGAAAATCGAGCGCGCGGAATTTA
ACACGGCGGGACGTAAGCCTACTGTCCTTTTGCGTATTGCTGACTTCATTGCAGCTATGAATGGTATGGACGCGAAGCA
AGATATGCAGGCGCTTTGGGATGCTGAAATTGCCATTATGAATGGTCGTGCCCAGACCACTATCATTAGTTATATCACG
AAGTATCGCAACGCCATCCGCGAAGCGTTCGGTGACGACCACCCTATGTTAAAGATCGCCACTGGAGATGCCGCAATGT
ATGACGAGGCTCGCCGTGTCAAGATGGAGAAAATTGCTAATAAACATGGAGCACTGATTACTTTCGAAAATTATCGTCA
AGTGTTGAAAATTTGCGAGGACTGTCTGAAATCATCTGACCCGCTTATGATCGGGATTGGCCTTATTGGAATGACTGGC
CGCCGCCCTTACGAGGTATTCACACAGGCGGAGTTCTCGCCAGCGCCATGGCAAAGGAGTCTCGAGTGGAGTATTC
TTTTTAACGGTCAGGCCAAGACCAAACAAGGTGAGGGTACTAAATTCGGAATCACATATGAGATCCCAGTACTGACTCG
TTCTGAAACAGTTTTAGCTGCATACAAACGTTTGCGCGAATCTGGCCAGGGAAAGTTATGGCACGGAATGAGTATCGAT
GATTTCTCGAGTGAAACTCGCCTTTTGTTACGCGATACCGTCTTCAATCTGTTCGAAGACGTCTGGCCTAAAGAAGAAC
TTCCGAAGCCGTATGGTTTGCGCCACCTGTACGCAGAGGTAGCATATCATAACTTCGCGCCACCTCACGTGACTAAGAA
TTCCTACTTTGCGGCTATTTTGGGACATAATAATAACGATTTGGAGACAAGTCTTTCATATATGACCTATACCCTTCCT
GAGGACCGTGATAATGCCTTAGCTCGTTTGAAGCGCACTAACGAACGCACGTTGCAACAGATGGCAACTATCGCCCCGG
TGAGCCGCAAGGGTCACCATCACCATCACCATTGActcgagggctcttcctgcatcacgggagat SEQ ID NO: 18 is an example forward mutagenic primer ("D97X-forward")
comprising a random codon, wherein N28 may be any of A, C, G, or T, N29 may be
any of A, C, G, or T, and B30 may be C, G, or T, but not A.
ATCGCCACTGGAGATGCCGCAATGTATNNBGAGGCTCGCCGTGTCAAGATGGAGAAA SEQ ID NO: 19 is an example reverse mutagenic primer ("D97X-reverse")
comprising a random codon, wherein V28 may be A, C, or G, but not T, N29 may be
any of A, C, G, or T, and N30 may be any of A, C, G, or T.
TTTCTCCATCTTGACACGGCGAGCCTCVNNATACATTGCGGCATCTCCAGTGGCGAT SEQ ID NO: 20 is an example forward primer ("F1").
GTT TAA CTT TAA GAA GGA GAT ATA CAT ATG SEQ ID NO: 21 is an example reverse primer ("R2").
CTC GGG TAG GGC AAC TAG TGC ATC TCC GCA GAT GCA GGA AGA GCC CTC GAG TCA ATG SEQ ID NO: 22 is an example TelA substrate comprising a FAM label at the 5' end
comprising a TelA recognition sequence (underlined) from A16-T41 (SEQ ID NO: 16).
FAM-
CGGCCAGTGGGATCCAATAACAATATCATGATATTGTTATTCGTACAGGAATCCGTACCTCAGACTCGTATCTTCACG SEQ ID NO: 23 is an example of a variant TelA of SEQ ID NO: 1, wherein X1 is
M(H)$_8$SGT. This sequence may be referred to as "N-terminally His-tagged ΔN105/D97"
or simply as "ΔN105/D97".
MHHHHHHHHSGTGVATSIVEKIERAEFNTAGRKPTVLLRIADFIAAMNGMDAKQDMQALWDAEIAIMNGRAQTTIISYI
TKYRNAIREAFGDDHPMLKIATGDAAMYDEARRVKMEKIANKHGALITFENYRQVLKICEDCLKSSDPLMIGIGLIGMT
GRRPYEVFTQAEFSPAPYGKGVSKWSILFNGQAKTKQGEGTKFGITYEIPVLTRSETVLAAYKRLRESGQGKLWHGMSI
DDFSSETRLLLRDTVFNLFEDVWPKEELPKPYGLRHLYAEVAYHNFAPPHVTKNSYFAAILGHNNNDLETSLSYMTYTL
PEDRDNALARLKRTNERTLQQMATIAPVSRKG -continued SEQ ID NO: 24 is an example variant TelA having a D202A substitution. This
sequence may be referred to as "D202A". In some embodiments, option-
ally M1 may be
M-H$_8$-SG or G442 may be G-H$_6$.
MLAAKRKTKTPVLVERIDQFVGQIKEAMKSDDASRNRKIRDLWDAEVRYHFDNGRTEKTLELYIMKYRNALKAEFGPKS
TPLAICNMKKLRERLNTYIARGDYPKTGVATSIVEKIERAEFNTAGRKPTVLLRIADFIAAMNGMDAKQDMQALWDAEI
AIMNGRAQTTIISYITKYRNAIREAFGDDHPMLKIATGDAAMYAEARRVKMEKIANKHGALITFENYRQVLKICEDCLK
SSDPLMIGIGLIGMTGRRPYEVFTQAEFSPAPYGKGVSKWSILFNGQAKTKQGEGTKFGITYEIPVLTRSETVLAAYKR
LRESGQGKLWHGMSIDDFSSETRLLLRDTVFNLFEDVWPKEELPKPYGLRHLYAEVAYHNFAPPHVTKNSYFAAILGHN
NNDLETSLSYMTYTLPEDRDNALARLKRTNERTLQQMATIAPVSRKG

DETAILED DESCRIPTION

Replication of linear chromosomes can be confounded by the difficulty of priming the lagging strand at each end. Some prokaryotes, including *Agrobacterium tumefaciens* and *Borrelia* species, have covalently closed telomeres, obviating this problem, but giving rise to another challenge—division of replicated chromosomes into daughter cells. These hairpin telomeres allow replication to proceed, but result in a circular replication intermediate comprising the original chromosome and the replicated chromosome, the ends of which are joined at telomere junctions in a head-to-head, tail-to-tail configuration. These conjoined chromosomes are separated by a telomere resolvase for each to be properly segregated into daughter cells. These enzymes cleave the conjoined chromosomes at the telomere junctions and form hairpin telomeres on each chromosome's head and tail ends. In each cell cycle, since only two catalytic events are needed for successful replication, telomere resolvases may be tightly regulated enzymes which may limit their utility as molecular tools. For example, telomere resolvases may not be capable of catalyzing more than one reaction per enzyme. This limitation of one enzyme molecule per catalytic reaction may be advantageous in a cell, where promiscuous and/or supernumerary activity could result in unwanted (and possibly lethal) chromosomal cleavage events. But, this same characteristic could blunt or compromise potential uses of telomere resolvases as reagents. The present disclosure relates, in some embodiments, to telomere resolvases (e.g., a TelA variants) having a turnover number≥1.1.

TelA proteomerase from *Agrobacterium tumefacien* C58 strain is required for the organism's linear DNA replication and resolves the circular dimeric DNA at the inverted-repeat junctions to regenerate the intact linear DNA with hairpin telomeres. TelA recognizes a minimal 26-bp sequence (namely, 5' AATAACAATA†TCA*TGATATTGTTATT 3' (SEQ ID NO:16), wherein the dagger † marks the cleavage site, the asterisk * denotes the center of the 13-bp inverted repeat, and the underlined portion is the overhang left after cleavage) in double-stranded DNA to generate hairpin ends (telomeres) after cleavage and ligation. An example cleavage reaction is shown in FIG. 1B comprising binding 110 of the minimal sequence (bar), cutting 120 at the cleavage sites, refolding 130, and ligation 140 across the respective 5' and 3' ends (curved lines).

General Considerations

Aspects of the present disclosure can be understood in light of the provided descriptions, figures, sequences, embodiments, section headings, and examples, none of which should be construed as limiting the entire scope of the present disclosure in any way. Accordingly, the innovations set forth herein should be construed in view of the full breadth and spirit of the disclosure.

Each of the individual embodiments described and illustrated herein has discrete components and features which can be readily separated from or combined with the components and/or features of any of the other several embodiments without departing from the scope or spirit of the present teachings. Lists of example species within a particular genus may vary in length at different places throughout the disclosure. Species lists shortened for convenience shall not be construed to exclude example species listed elsewhere in the specification. Any recited method can be carried out in the order of events recited or in any other order which is logically possible. Unless otherwise expressly stated to be required herein, each component, feature, and method step disclosed herein is optional and the disclosure contemplates embodiments in which each optional element may be expressly excluded. As such, this statement is intended to serve as antecedent basis for use of such exclusive terminology as "solely," "only" and the like in connection with the recitation of claim elements or use of a "negative" limitation. It is further intended to serve as antecedent basis for use of such elective terminology as "optionally" and the like in connection with the recitation of one or more claim elements.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "amino acid salt" refers to molecules formed by or comprising an anion of an amino acid (e.g., A, C, D, E, F, G, H, I, K, L, M, N, P, Q, R, S, T, V, W, Y) and a cation of a base (e.g., sodium, potassium, calcium, magnesium, manganese). Examples include glycine sodium salt, sodium aspartate salt, sodium glutamate salt, sodium lysinate, sodium serinate, threonine sodium salt, sodium alaninate, glycine potassium salt, potassium aspartate salt, potassium glutamate salt, potassium lysinate, potassium serinate, threonine potassium salt, potassium alaninate, glycine calcium salt, calcium aspartate salt, calcium glutamate salt, calcium lysinate, calcium serinate, threonine calcium salt, and calcium alaninate.

In the context of the present disclosure, "buffer" and "buffering agent" refer to a chemical entity or composition that itself resists and, when present in a solution, allows such solution to resist changes in pH when such solution is contacted with a chemical entity or composition having a higher or lower pH (e.g., an acid or alkali). Examples of suitable non-naturally occurring buffering agents that may be used in disclosed compositions, kits, and methods include HEPES, MES, MOPS, TAPS, tricine, and Tris. Additional examples of suitable buffering agents that may be included in disclosed compositions, kits, and methods include ACES, ADA, BES, Bicine, CAPS, carbonic acid/bicarbonate acid, CHES, citric acid, DIPSO, EPPS, histidine, MOPSO, phosphoric acid, PIPES, POPSO, TAPS, TAPSO, and triethanolamine.

In the context of the present disclosure, "closed end" refers to duplex DNA or RNA in which the upper strand and the lower strand are covalently joined (e.g., by phosphodiester bonds) and form single polynucleotide molecule having a hairpin. A circular, single-stranded DNA molecule with one or more inverted repeats may have a like number of closed ends upon intramolecular hybridization of such repeats. For example, a circular, single-stranded DNA molecule comprising a first half of an inverted repeat spanning half the circle and the second half of the inverted repeat spanning the other half of the circle may form a linear, duplex DNA with two closed ends, one at each end.

In the context of the present disclosure, "container" refers to a human-made container. A container may comprise one or more walls (e.g., defining an interior volume) and optionally one or more openings. Containers comprising one or more openings may further comprise one or more closures (e.g., a removable closures) for some or all such openings. A closure optionally may comprise an aperture or a septum, for example, to provide fluid communication with a volume of the container and a connected or inserted tube or syringe. Examples of containers include boxes, cartons, bottles, tubes (e.g., test tubes, microcentrifuge tubes), plates (e.g., 96-well, 384-well plates), vials, pipette tips, and ampules. Containers and/or closures may comprise any desired material including paper, plastics, glass, silicone, composites, metals, alloys, or combinations thereof. Containers and/or closures may comprise materials that are compostable, recyclable, and/or sustainable.

In the context of the present disclosure and with respect to an amino acid residue or a nucleotide base position, "corresponding to" refers to positions that lie across from one another when sequences are aligned, e.g., by the BLAST algorithm. An amino acid position in a functional or structural motif in one polymerase may correspond to a position within a functionally equivalent functional or structural motif in another polymerase.

In the context of the present disclosure, "detergent" "surfactant" refer to amphipathic molecules including anionic surfactants, cationic surfactants, nonionic surfactants, and zwitterionic surfactants. Examples include NONIDET NP-40®, sodium dodecyl sulfate, octoxinol-9, lecithin, poloxamers, sphingophospholipids, lecithin, IGEPAL® CA 630, polysorbate 20, polysorbate 80, propylene glycol stearate, polyethylene glycol monodecyl ethers, CHAPS, CHAPSO, glycerophospholipids, palmitoyl lysophosphatidyl-L-serine, oleic acid and caprylic acid and any of the surfactants and detergents disclosed in U.S. Pat. No. 6,875, 748 and US20090011976.

In the context of the present disclosure, "fusion" refers to two or more polypeptides, subunits, or proteins covalently joined to one another (e.g., by a peptide bond). For example, a protein fusion may refer to a non-naturally occurring polypeptide comprising a protein of interest covalently joined to a second polypeptide. Examples of a second polypeptide include a reporter protein, a purification tag, and expression tag, a polynucleotide binding protein, an enzyme, a conjugation tag (e.g., a SNAP® tag), and a peptide linker. Unless otherwise disclosed, the protein of interest may be nearer to the N-terminal end or nearer to the C-terminal end than the second polypeptide to which it is joined. A fusion may comprise a non-naturally occurring combined polypeptide chain comprising two proteins or two protein domains joined directly to each other by a peptide bond or joined through a peptide linker.

In the context of the present disclosure, "immobilized" refers to covalent attachment of an enzyme to a solid support with or without a linker. Examples of solid supports include beads (e.g., magnetic, agarose, polystyrene, polyacrylamide, chitin). Beads may include one or more surface modifications (e.g., $O^6$-benzylguanine, polyethylene glycol) that facilitate covalent attachment and/or activity of an enzyme of interest. For example, a support may comprise a ligand and an enzyme may have a receptor for such ligand or an enzyme may comprise a ligand and a support may comprise a receptor for such ligand. Receptor-ligand binding may be covalent or non-covalent. Non-covalent attachment (e.g., avidin:biotin, chitin:CBP) may be useful in some embodiments, for example, where the level of dissociation of the binding partner is deemed tolerable. A linker may be disposed between a support and an enzyme. For example, linker disposed between a support and an enzyme may have a first covalent bond to the support and a second covalent bond to the enzyme. An immobilized enzyme comprising a ligand-receptor attachment may have a linker disposed between the support and the ligand-receptor attachment, a linker disposed between the enzyme and the ligand-receptor attachment, or both. An immobilized enzyme comprising a linker may also comprise an optional covalent bond directly between the enzyme and the support. A linker may be of any desired length and have any desired range of motion. A peptide linker may comprise one or more repeats (e.g., 1-10 repeats) of glycine-serine.

In the context of the present disclosure, "non-naturally occurring" refers to a molecule (e.g., a polynucleotide, polypeptide, carbohydrate, or lipid) or composition that does not exist in nature. Such a molecule or composition may differ from naturally occurring molecules or compositions in one or more respects. For example, a polymer (e.g., a polynucleotide, polypeptide, or carbohydrate) may differ in the kind and arrangement of the component parts (e.g., nucleotide sequence, amino acid sequence, or sugar molecules). A polymer may differ from a naturally occurring polymer with respect to the molecule(s) to which it is linked. For example, a "non-naturally occurring" polypeptide (e.g., protein) may differ from naturally occurring polypeptides in its secondary, tertiary, or quaternary structure, by having (or lacking) a chemical bond (e.g., a covalent bond including a peptide bond, a phosphate bond, a disulfide bond, an ester bond, and ether bond, and others) to a lipid, a carbohydrate, a second polypeptide (e.g., a fusion protein), or any other molecule. Similarly, a "non-naturally occurring" polynucleotide or nucleic acid may comprise (or lack) one or more other modifications (e.g., an added label or other moiety) to the 5'-end, the 3' end, and/or between the 5'- and 3'-ends (e.g., methylation) of the nucleic acid. A "non-naturally occurring" molecule or composition may differ from naturally occurring compositions in one or more of the following respects: (a) having components that are not combined in nature, (b) having components in ratios and/or concentrations not found in nature, (c) lacking one or more components otherwise found in naturally occurring molecules or compositions (e.g., a cell-free composition, a chromosome-free composition, a histone-free composition, a polymerase-free composition, a cell membrane-free composition), (d) having a form not found in nature (e.g., dried, freeze dried, lyophilized, crystalline, aqueous, immobilized), and (e) having one or more additional components beyond those found in nature (e.g., a buffering agent, a detergent, a dye, a solvent or a preservative).

In the context of the present disclosure, an amino acid sequence having a percent identity to a reference sequence may be disclosed with or without specifying one or more of the variant positions. For example, if a 300-amino acid polypeptide is disclosed as having an amino acid sequence having at least 90% identity to a 300-amino acid reference sequence, the sequence may differ from the reference sequence at any positions up to 10. If a 300-amino acid polypeptide is disclosed as having an amino acid sequence having at least 90% identity to a 100-amino acid reference sequence and having a D97K substitution, the sequence may differ from the reference sequence as noted at position 97 and differ from the reference sequence at up to 29 other positions.

With reference to an amino acid, "position" refers to the place such amino acid occupies in the primary sequence of a peptide or polypeptide numbered from its amino terminus to its carboxy terminus.

In the context of the present disclosure, "substitution" refers to an amino acid residue at a position in a comparator amino acid sequence that differs with respect to a corresponding position of a reference amino acid sequence, where the comparator and reference sequences are at least 60% identical to each other or at least 70% identical to each other or at least 80% identical to each other. A reference sequence and comparator sequence may have the same length or similar lengths (e.g., differing by ≤12%, ≤5%, ≤1%). A substitute amino acid residue at a position, in addition to differing from the corresponding position of a reference amino acid sequence, may differ from the amino acid at the corresponding position of all naturally-occurring sequences that are at least 60% identical to each other or at least 70% identical to each other or at least 80% identical to the reference sequence. Optionally, a substitute amino acid may have different properties than the amino acid in the corresponding position of the reference sequence. Optionally, a substitute amino acid may have similar properties to the amino acid in the corresponding position of the reference sequence (a "conservative" substitution). For example, a non-polar amino acid (e.g., A, V, L, I, M, W, and F (and optionally C, G, and P) may substitute for another non-polar amino acid, a polar amino acid (e.g., N, Q, S, T, and Y) may substitute for another polar amino acid (e.g., C, D, E, H, K, N, P, Q, R, S, and T), a positively charged amino acid (H, K, and R) may substitute for another positively charged amino acid, and a negatively charged amino acid (e.g., D and E) may substitute for another negatively charged amino acid. A substitute amino acid may be a natural amino acid (e.g., replacing another natural amino acid or a non-natural amino acid). A substitute amino acid may be a non-natural amino acid (e.g., replacing a natural amino acid or another non-natural amino acid).

Figure 1A:
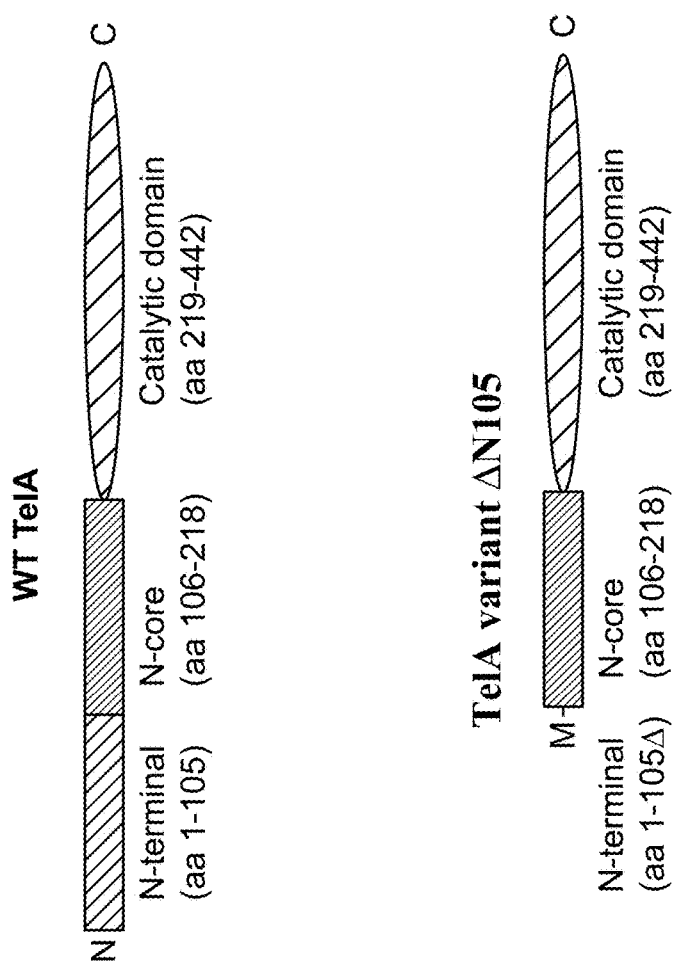
FIG. 1A illustrates domain organization of an example wild type telomere resolvase (TelA) and an example variant TelA in which the 105 N-terminal amino acid residues are deleted and replaced with a methionine (M) residue. This deletion/replacement may be referred to herein as "ΔN105". Example amino acid numbering for each domain is provided. Over 50 homologs of wild type TelA have been identified in *Agrobacterium* and *Rhizobium* species. Examples include ResT having a 32 bp target, phage PY54-Tel having a 42 bp target, TelN having a 56 bp target, and TelK having a 54 bp target.

In the context of the present disclosure, "TelA" refers to a protein comprising in an N-terminal to C-terminal direction, an N-terminal helical domain, a core domain ("N-core"), and a catalytic region comprising a reactive tyrosine and a coordinating amino acid pentad, but lacks a C-terminal stirrup domain. An example, of this domain organization is illustrated in FIG. 1A. A wild-type TelA may have a turnover number ≤1.1 or ≤1.2. TelA includes In the context of the present disclosure, "TelA variant" refers to a non-naturally occurring variant of TelA that recognizes the sequence

```
                                        (SEQ ID NO: 16)
5' . . . AATAACAATA▼TCATGATATTGTTATT . . . 3'
3' . . . TTATTGTTATAGTACT▲ATAACAATAA . . . 5'
``` and cleaves phosphodiester bonds where indicated by the arrows. A variant TelA may comprise one or more amino acids in addition to a wild-type TelA (e.g., one or more insertions and/or extensions). For example, a variant TelA may comprise (e.g., at its amino terminal end or carboxy terminal end) 1-25 amino acids. Such additional amino acids may enable, facilitate and/or enhance translation, expression, cellular sorting, inactivation (e.g., by including a protease recognition and/or cleavage site), and/or purification. Such additional amino acids may constitute a linker, for example, to a support (e.g., a magnetic bead) or another protein. A variant TelA may include one (or more) amino acid fewer than a wild-type TelA (e.g., one or more deletions anywhere along the length of the sequence).

In some embodiments, a variant TelA may comprise, in an N-terminal to C-terminal direction, a core domain ("N-core") spanning amino acids corresponding to amino acids 106-218 of SEQ ID NO:13 and a catalytic domain spanning amino acids corresponding to amino acids 219-442 of SEQ ID NO:13. Optionally, a variant TelA may be free of or may comprise an N-terminal domain (e.g., spanning 105 amino acids) corresponding to amino acids 1-105 of SEQ ID NO:13. A variant TelA may have an amino acid sequence sharing any desired degree of sequence identity with a wild-type TelA up to (but excluding) 100% identity. For example, a variant TelA may have an amino sequence having at least 75%, at least 80%, at least 85%, at least 90%, at least 92%, at least 94%, at least 95%, at least 98%, or at least 99% identity to SEQ ID NO:1, optionally wherein X1 is selected from T, M-T and M-$H_8$-S-G-T, X97 is any amino acid other than D or A, X98 is E or A, and/or X337 is selected from G and G-$H_6$. For example, a variant TelA may have an amino sequence having at least 75%, at least 80%, at least 85%, at least 90%, at least 92%, at least 94%, at least 95%, at least 98%, or at least 99% identity to SEQ ID NO:1, optionally wherein X1 is selected from T, M-T and M-$H_8$-S-G-T, Y96 is Y (e.g., not a substitution, insertion, or deletion), X97 is any amino acid other than D or A, X98 is E or A, R100 is R (e.g., not a substitution, insertion, or deletion), R101 is R (e.g., not a substitution, insertion, or deletion), K103 is K (e.g., not a substitution, insertion, or deletion), and/or X337 is selected from G and G-$H_6$. A variant TelA may have an amino sequence having at least 75%, at least 80%, at least 85%, at least 90%, at least 92%, at least 94%, at least 95%, at least 98%, or at least 99% identity to SEQ ID NO:1, optionally wherein X1 is selected from T, M-T and M-H$_8$-S-G-T, X97 is K or R, X98 is E or A, and/or X337 is selected from G and G-H$_6$. A variant TelA may have an amino sequence having at least 75%, at least 80%, at least 85%, at least 90%, at least 92%, at least 94%, at least 95%, at least 98%, or at least 99% identity to SEQ ID NO:1, optionally wherein X1 is selected from T, M-T and M-H$_8$-S-G-T, Y96 is Y (e.g., not a substitution, insertion, or deletion), X97 is K or R, X98 is E or A, R100 is R (e.g., not a substitution, insertion, or deletion), R101 is R (e.g., not a substitution, insertion, or deletion), K103 is K (e.g., not a substitution, insertion, or deletion), and/or X337 is selected from G and G-H$_6$. A variant TelA may have an amino sequence having at least 75%, at least 80%, at least 85%, at least 90%, at least 92%, at least 94%, at least 95%, at least 98%, or at least 99% identity to SEQ ID NO:1 and having at least one additional positively charged side within 10 Å of the alpha carbon of the amino acid corresponding to D97, wherein the one additional positively charged side chain constitutes a substitution relative to wild-type enzyme.

Example variants are shown in Table 1 which sets forth the required degree of sequence identity to a reference wild type sequence and the position of required substitutions (numbering according to the reference sequence).

TABLE 1

Variant TelA

| Sequence Identity | Reference sequence | Substitution(s) at | Example substitutions | Example SEQ ID NO |
|---|---|---|---|---|
| (a) ≥90%, ≥92%, ≥94%, ≥95%, ≥97%, ≥98%, or ≥99%; and (b) <100% | SEQ ID NO: 13 | 1-105 202 203 442 1-105; and 202 1-105; 202; and 203 1-105; 202; 203; and 442 1-105; 202; 203; and 442 | ΔN105 D202K or D202R E203A G and G-H$_6$ ΔN105/D97K ΔN105/D97K/ E98A N-terminally His-tagged ΔN105/D97K C-terminally His-tagged ΔN105/D97K | 1-10 2-5, 7-12 3, 5 2-6, 9-10 2-5, 7, 9 3, 5 7-8 9-10 |

Figure 2A:
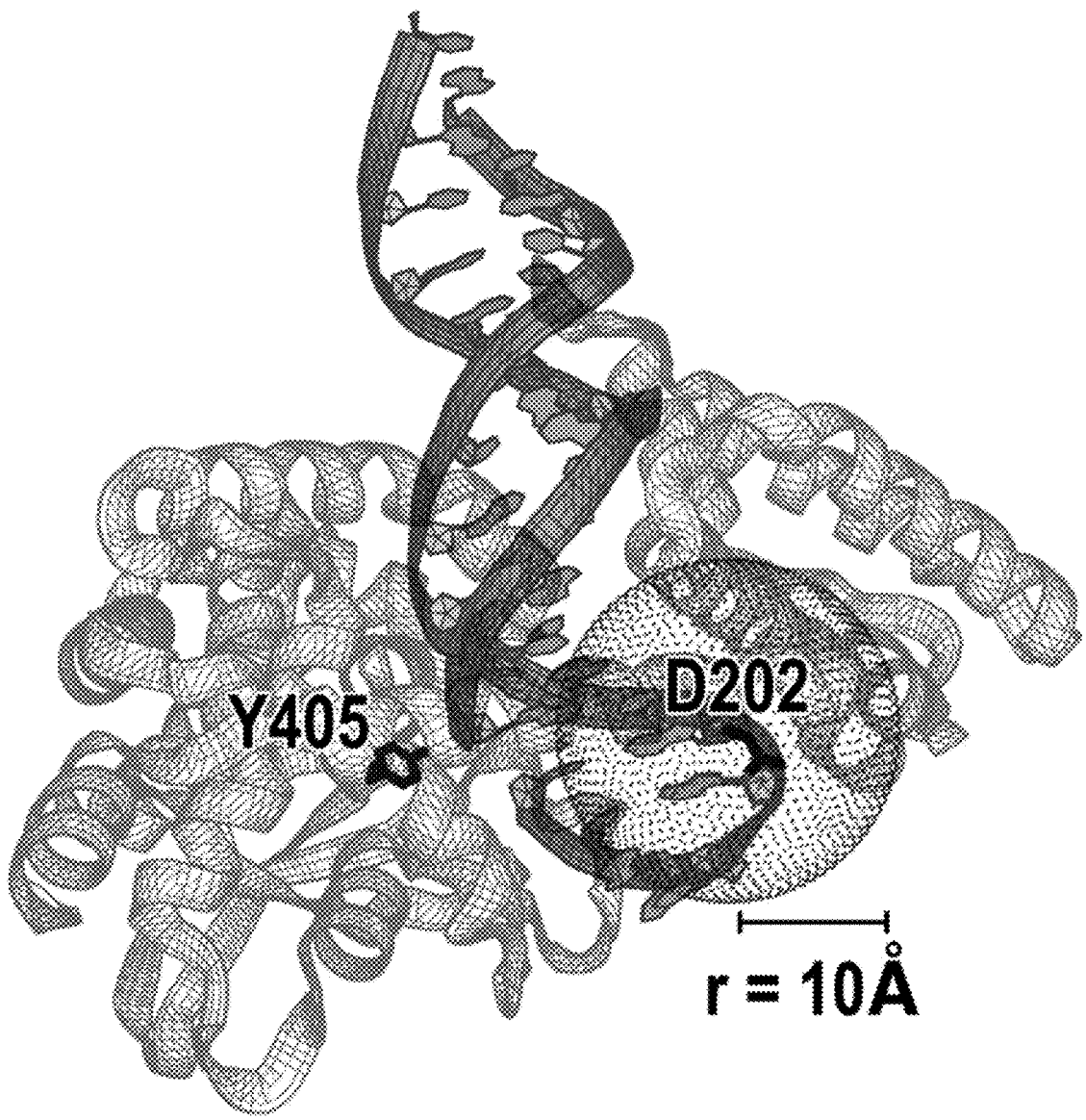
FIG. 2A shows an example structure of a TelA monomer (e.g., ribbons and sheets having lighter colors) bound to a DNA molecule (darker helical shape) based on TelA (Genbank accession 4E0G). The sphere marks a volume 10 Å in diameter that is enlarged in FIG. 2B.
Figure 2B:
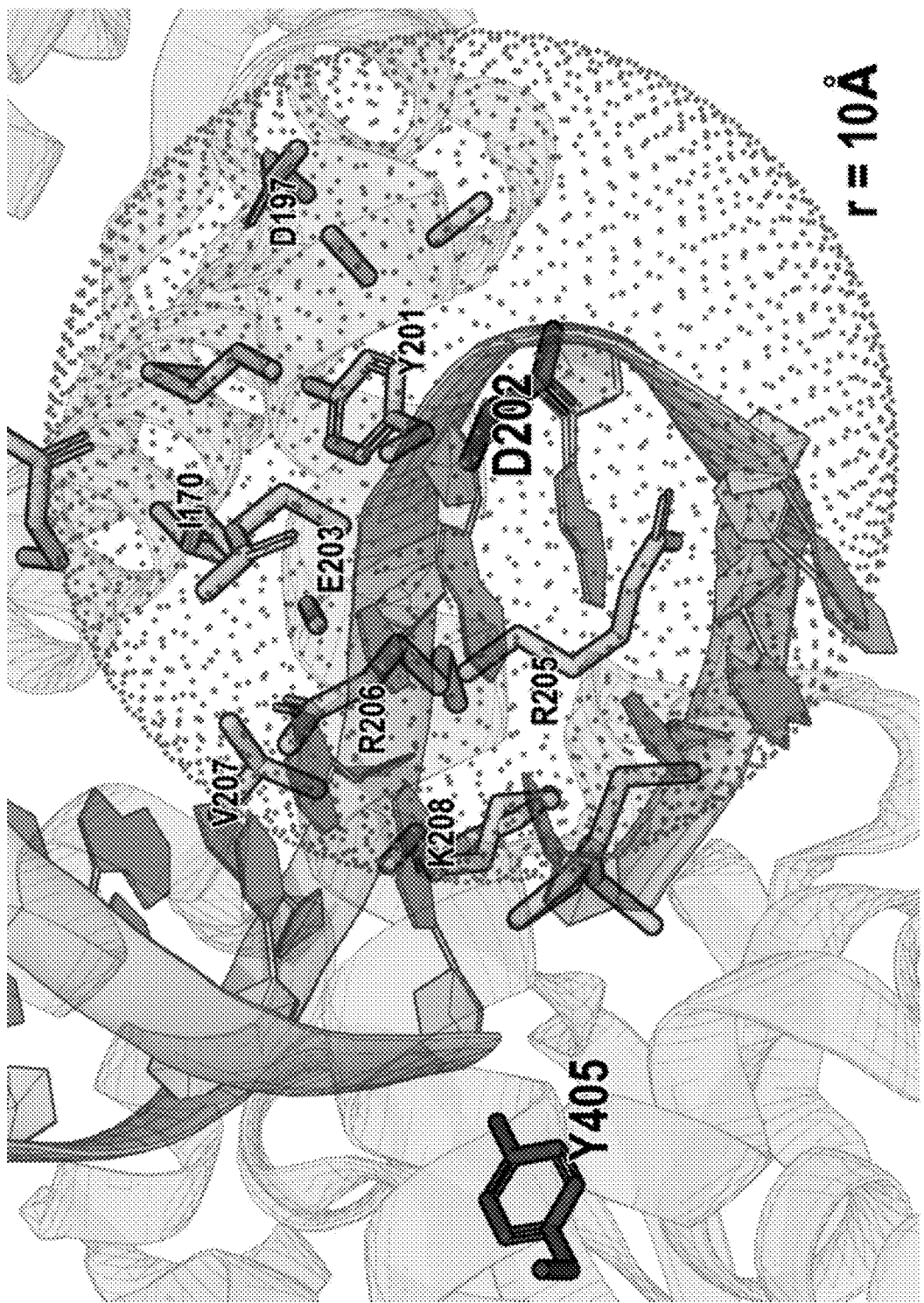
FIG. 2B shows an example illustration of TelA active site residues contacting hairpin DNA structure.

The active site of a variant TelA may retain, according to some embodiments, conserved catalytic site residues of the wild-type. For example, a variant TelA may have an active site comprising or defined by amino acids, in part or in whole, occupying the space defined by a sphere with a radius of 10 Å (angstrom) extending from the alpha carbon of residue D202 of wild-type TelA (e.g., as shown in FIG. 2B (conserved tyrosine 405 highlighted for reference); Shi, K et al., 2013, Plos Biology vol. 11 e1001472 ("Shi 2013"); Huang W M et al., 2012, J. Biol. Chem., 287, 25551-25563 ("Huang")) or extending from the alpha carbon of residue D97 of ΔN105/D97K or extending from the alpha carbon of residue D97 of ΔN105/D97R. For example, a variant TelA may have an active site comprising or defined by amino acids (e.g., I, D, Y, D, E, R, R, V, k, and/or Y) that correspond respectively to I170, D197, Y201, D202, E203, R205, R206, V207, K208, and/or Y405 or SEQ ID NO:13 or that correspond respectively to 165, D92, Y96, X97, X98, R100, R101, V102, K103, and/or Y300 OF SEQ ID NO:1.

In some embodiments, a variant TelA may comprise an active site like wild-type TelA. For example, amino acids corresponding to X97 of SEQ ID NO:1 may interact with DNA as shown in FIG. 2A and set forth in Shi 2013; and Huang. For example, Y96, X97, and R100 may interact with DNA bases ($T_{14}$ and $A_{16}$) and backbone phosphates in the hairpin formed by $T_{11}$-$A_{16}$ of SEQ ID NO:16, wherein $T_{11}$ and $A_{16}$ base pair with one another and $C_{12}$ and $G_{15}$ base pair with one another, while $A_{13}$ and $T_{14}$ are unpaired in the loop. A variant TelA, in some embodiments, may have a structure comprising α-helix and/or β-sheet (e.g., FIG. 2A and FIG. 2B).

A variant TelA may have catalytic activity (e.g., at least 50%, at least 60%, at least 70%, or at least 80% of its maximal activity) at and/or following exposure to temperatures in ranges X to Y, where X is any of 20° C., 25° C., 30° C., 35° C., 40° C., 45° C. and Y is any of 30° C., 35° C., 40° C., 45° C., 50° C., 55° C., 60° C. For example, a variant TelA may have catalytic activity at and/or following exposure to temperatures in ranges 25° C.-55° C., 30° C.-45° C., 30° C.-60° C., or 35° C.-55° C. A variant TelA may or may not have activity outside of a provided temperature range. A variant TelA may be inactivated at temperatures≥65° C., ≥70° C., ≥75° C., ≥80° C. (e.g., ≥30 minutes).

Catalytic activity of a variant TelA may persist across a range of salt concentrations, temperatures and/or pH. For example, a variant TelA may display catalytic activity under a range of conditions and/or following removal from exposure to such conditions. A variant TelA may have catalytic activity at and/or following exposure to a pH from X† to Y†, where X† is any of pH 4, 4.5, 5, 5.5, 6, 6.5, 7, and Y† is any of pH 6.5, 7, 7.5, 8, 8.5, 9, 9.5, 10, 10.5, 11 and X†<Y†. For example, a variant TelA may be active at pH 6.5-10 and/or pH 7-9.

A TelA variant may catalyze more than one telomere junction cleavage event, more than one hairpin telomere formation event, or both more than one telomere junction cleavage event and more than one hairpin telomere formation event. A TelA variant may have a turnover number≥1.1, ≥1.2, ≥1.3, ≥1.4, ≥1.5, ≥1.6, ≥1.7, ≥1.8, ≥1.9, or ≥2.0, for example, with respect to a linear duplex oligo DNA substrate having at least one recognition sequence according to SEQ ID NO:16. A TelA variant may have a turnover number≤2, ≤3, ≤4, ≤5, or ≤10. Unless otherwise indicated, concentrations of TelA refer to the concentration of TelA monomers even though DNA binding, cleavage, and/or ligation by a variant TelA may depend on formation of a dimer comprising two molecules of variant TelA per substrate molecule.

In the context of the present disclosure, "turnover number", applied to an enzyme, refers the number of reactions an enzyme performs before ceasing to function. Turnover number may be expressed, for example, as the moles of substrate that a mole of the enzyme can convert to product before it ceases to function. The theoretical upper limit for turnover number is infinity, representing an enzyme that ceaselessly converts substrate to product without being consumed, degraded or otherwise inactivated by its activity. The theoretical lower limit for turnover number is one, representing a stoichiometric reaction in which every molecule of enzyme catalyzes only one reaction before being consumed, degraded or otherwise inactivated. With respect to dimeric enzymes, turnover number may be expressed in terms of the dimer, the substrate of the dimer, and the products of the dimer. For example, turnover number for a telomere resolvase dimer may be expressed in terms of the dimer's cleavage of both strands of a substrate double-stranded DNA and formation of hairpin closures across each of the two double-stranded ends.

All publications, patents, and patent applications mentioned in this specification are herein incorporated by reference to the same extent as if each individual publication, patent, or patent application was specifically and individually indicated to be incorporated by reference. Reagents referenced in this disclosure may be made using available materials and techniques, obtained from the indicated source, and/or obtained from New England Biolabs, Inc. (Ipswich, MA).

Most bacterial genomes exist in cells as circular double-stranded DNA (dsDNA) in various sizes ranging from ~2-8 million base pairs (mbp). In some cases, however, the genomes of bacteria, bacteriophages (phages), and plasmids can exist as liner forms with hairpin at the termini of chromosome or covalently bound protein at the ends for protection and replication (extension). In *Agrobacterium tumefacien* C58 strain, the genome of 2.076 mbp exist as a linear DNA with hairpins at both ends. The left and right hairpins are also called left and right telomeres, which are catalyzed and formed by the enzyme TelA protelomerase (442 aa residues, 50.33 kDa) encoded in the bacterial genome. The enzyme has a domain arrangement (FIG. 1A) comprising, in an N-terminal to C-terminal direction, an N-terminal domain spanning 105 amino acids 1-105, a core domain ("N-core") spanning amino acids 106-218, and a catalytic domain spanning amino acids 219-442. The 50-bp target site of TelA contains two directs repeats: the external 9-bp repeats and the internal 13-bp repeats. A serial deletion study indicated that the internal 13-bp repeats is required for TelA binding, cleavage, ligation, and hairpin formation. The external repeat of 9-bp can be deleted without greatly affecting TelA activity. Thus, the minimal TelA site is 26 bp with 13-bp inverted repeat (5' AATAACAATATCA*TGATATTGTTATT 3' (SEQ ID NO:16), * shows the center of the symmetry). TelA cleaves the 26-bp dsDNA site and generates 6 base single-stranded DNA intermediate (FIG. 1B), and by base stacking and non-standard base pairing, the 6 base 5' overhang of the top strand folds back and ligated to the 3' end of the bottom strand to form the hairpin structure, leaving 2 nucleotides in the hairpin as orphan bases. TelA protelomerase catalyzes the target recognition of TOS site (Telomerase Occupancy Site), introduces nicks on both strands, forms single-stranded DNA (ssDNA) refolding intermediate, and performs ligation of DNA ends to form left and right telomeres as the enzyme forms a 3' phosphotyrosine enzyme-DNA linked intermediate. The Tyr405 residue is involved in catalysis (cleavage and ligation) in conjunction with a few other critical residues. The catalytic Tyr residue is conserved in all protelomerases, some recombinases and topoisomerases (FIG. 2A).

Protelomerase is useful to generate unit length ds linear DNA with hairpin ends for DNA vaccine development, for DNA vector-based gene therapy, and for engineering plural potent stem cells. A circular plasmid or viral vector with TOS (protelomerase occupancy site) and gene of interest insert can be amplified by rolling circle amplification (RCA) in test tube, and the RCA-amplified DNA can be cleaved/ligated by protelomerase to form unit-length linear dsDNA for transfection into mammalian cells. The hairpin protected ends have been shown to increase DNA stability and enhanced gene expression after transfection into recipient cells.

Part of the N-terminal region of TelA is dispensable for TelA catalytic activity. Deletion of N-terminal region from 11 to 72 residues did not show any negative mutational effects on protein stability or enzyme activity. Deletion of N-terminal 86 and 106 aa residues did not alter TelA activity, but the truncations may have affected enzyme stability as more protein breakdown products were detected in partially purified enzyme preparations. But a larger deletion of 123 aa residues in the N-terminus reduced TelA activity, and deletion of 140 aa residues totally abolished TelA activity. Deletion of 10 amino acid residues at the C-terminus of TelA did not affect TelA protein stability and enzymatic activity.

Divalent cations can also affect TelA activity. TelA activity was assessed on double-strand duplex oligos containing a 36-bp target site. WT enzyme can achieve 35-40% telomere resolution in 10 min. Addition of 4 mM $MgCl_2$ or $CaCl_2$) showed enhanced activity, resulting in 95-100% telomere resolution in 10 min at 30° C. It is known that divalent cations are not required for Tyr-medicated catalytic activity, but it is not clear how $Mg^{2+}$ or $Ca^{2+}$ cations stimulate TelA activity by binding to the protein or binding to the negatively charged DNA backbone phosphates.

The stimulation of TelA activity can also be achieved by site-directed mutagenesis. A TelA variant (D202A) in ΔN106 background (N-terminal 1-106 aa deletion) ΔN106/D202A displays enhanced enzyme activity compared to the wild-type (WT) enzyme). (It will be understood that the actual position of the amino acid substitution counting from the N-terminus after the 106 aa deletion is D96, not D202.) It was proposed that the N-terminal region 1-106 may have an inhibitory function to the full-length enzyme. Thus, deletion of the N-terminal region from 1-106 in conjunction with D202 (a.k.a. D96 in ΔN106) to Ala substitution resulted in an enzyme with "hyperactive" property. Here the "hyperactive" enzyme property was likely caused by N-terminal 106 aa deletion and D202A (a.k.a. D96A) aa substitution. Here the "hyperactive" variant enzyme (ΔN106/D202A) is defined by approximately 2-fold increase in telomere resolution activity. WT enzyme has ~40-45% telomere resolution activity in $Mg^{2+}$ buffer, compared to the D202A variant with 100% telomere resolution activity in the same buffer. Interestingly, the N-terminal deletion variant ΔN106 is less sensitive to divalent cations since it showed similar activity in the presence of 0.2 mM EDTA, or in buffers with 2 mM of $Mg^{2+}$ or $Ca^{2+}$.

Enzymes and Compositions

The present disclosure relates, in some embodiments, to TelA variants having one or more desirable properties including, for example, high turnover relative to wild-type and/or recognition and type IIS cleavage of SEQ ID NO:16 and compositions comprising such variants. A variant enzyme composition may comprise, for example, a variant enzyme (e.g., having an amino acid sequence at least 85% identical to one or more of SEQ ID NOS:1-12) and having at least one substitution relative to wild-type enzyme. A variant protelomerase composition may be free of one or more other catalytic activities. For example, a variant TelA composition may be free of proteases (e.g., non-specific proteases or proteases having specific cleavage recognition sites), free of nucleases (e.g., RNases and/or DNases), free of polymerase activity, free of RNA and/or DNA modification activity, free of kinase activity, and/or free of phosphorylation and/or glycosylation activities, in each case, under desired test conditions (e.g., conditions of time, temperature, pH, salinity, model or intended substrate and/or others), for example, conditions intended to replicate conditions of a specific use of the variant TelA composition or intended to represent conditions for a range of uses.

According to some embodiments, a variant TelA composition may comprise, for example, a variant TelA and, optionally, any of (including one or more of) a buffering agent (e.g., a storage buffer, a reaction buffer), an excipient, a salt (e.g., NaCl, MgCl$_2$, MgCl$_2$, CaCl$_2$, an amino acid salt), a protein (e.g., an RNA polymerase, a DNA binding protein, a DNA ligase), a stabilizer, a detergent (for example, ionic, non-ionic, and/or zwitterionic detergents (e.g., octoxinol-9, lecithin, poloxamers, propylene glycol stearate, N-Lauroylsarcosine, polysorbate 20, glycerophospholipids, oleic acid, and caprylic acid), a polyanion (e.g., spermidine, spermine, putrescine), a polynucleotide (e.g., a substrate DNA comprising a nucleotide sequence including SEQ ID NO:16), a cell (e.g., intact, digested, or any cell-free extract), a biological fluid or secretion (e.g., mucus, pus, blood, urine, saliva), an aptamer, a pH indicator (e.g., azolitimin, bromocresol purple, bromothymol blue, methylene blue, cresol red, neutral red, naphtholphthalein, phenol red), a crowding agent, a sugar (e.g., a mono, di, tri, tetra, or higher saccharide), a starch, cellulose, a glass-forming agent (e.g., glycerol, raffinose, stachyose, or trehalose for lyophilization), a lipid, an oil, aqueous media, a support (e.g., a bead) and/or (non-naturally occurring) combinations thereof. Combinations may include for example, two or more of the listed components (e.g., a salt and a buffer) or a plurality of species of a single listed component (e.g., two different salts or two different sugars). In some embodiments, a composition may comprise 0.5-25 mM MgCl$_2$, e.g., 2 mM MgCl$_2$ and/or 0.5-100 mM KCl (e.g., 25-75 mM KCl). Compositions may comprise one or more polyanions at any desired concentration (e.g., individually or total concentrations of 0.1-10 mM, 0.5-5 mM, 1 mM, 1.5 mM, 2 mM, 2.5 mM, 3 mM, 3.5 mM, 4 mM, 4.5 mM or 5 mM) and may be included to bind negatively charged molecules. In some embodiments, a composition may comprise a salt (e.g., a mineral salt, an amino acid salt) in a concentration in a range of 20 mM, 30 mM, 40, mM, 50 mM, or 60 mM to 50 mM, 75 mM, 100 mM, 200 mM, 300 mM, 450 mM, or 500 mM. Example polyanions include spermidine, spermine, putrescine, polyethylenimine, 1,4,7-triazacyclononane, cyclen, ethylenediamine, or 1,3,5,-triazinane. According to some embodiments, variant TelA compositions may comprise (a) a variant TelA, (b) a buffer, and optionally (c) a polynucleotide (e.g., a substrate DNA) or a cellular extract or a cell-free preparation comprising a polynucleotide (e.g., a substrate DNA comprising a nucleotide sequence including SEQ ID NO:16). A composition, according to some embodiments, may include a detergent (e.g., octoxinol-9, lecithin, poloxamers, propylene glycol stearate, N-Lauroylsarcosine, polysorbate 20, glycerophospholipids, oleic acid, and caprylic acid) at a concentration in a range of 0.001%, 0.005%, 0.01%, 0.05, or 0.1% to 0.01%, 0.05%, 0.1%, 0.5%, 1%, 2%, 3%, 4%, or 5%, in each case (w/v). A composition, according to some embodiments, may comprise a salt (e.g., a mineral salt, an amino acid salt) in a concentration in a range of 20 mM, 30 mM, 40, mM, 50 mM, or 60 mM to 50 mM, 75 mM, 100 mM, 200 mM, 300 mM, 450 mM, or 500 mM and a detergent (e.g., octoxinol-9, lecithin, poloxamers, propylene glycol stearate, N-Lauroylsarcosine, polysorbate 20, glycerophospholipids, oleic acid, and caprylic acid) at a concentration in a range of 0.001%, 0.005%, 0.01%, 0.05, or 0.1% to 0.01%, 0.05%, 0.1%, 0.5%, 1%, 2%, 3%, 4%, or 5%, in each case (w/v). In some embodiments, an added protein (e.g., an RNA polymerase, a DNA binding protein, a DNA ligase) may enhance binding, cleavage, ligation, specific activity, turnover and/or another property of variant TelA. For example, a composition comprising a variant TelA and a DNA ligase (e.g., T4 DNA ligase, Hi-T4 DNA ligase, salt T4 DNA ligase, *E. coli* DNA ligase, T7 DNA ligase, Taq DNA ligase) may display higher turnover than the variant TelA alone under the same reaction conditions.

In some embodiments, protelomerases (e.g., variant protelomerases) and compositions comprising one or more protelomerases (e.g., one or more TelA variants) may have any desirable form including, for example, a liquid, a gel, a film, a powder, a cake, and/or any dried or lyophilized form. A TelA composition may comprise a TelA and a support or matrix, for example, a film, gel, fabric, column or bead comprising, for example, a magnetic material, agarose, polystyrene, polyacrylamide, and/or chitin. A variant protelomerase and compositions comprising a variant protelomerase may be active at higher temperatures. For example, a TelA or a TelA composition may display protelomerase activity at 30° C.-70° C., 37° C.-65° C., 40° C.-65° C., or 45° C.-65° C. that equals or exceeds the activity of wild type TelA with the same substrate under the same conditions. Aqueous compositions (e.g., comprising a variant TelA) may include, for example, one or more elements that reduce the composition's melting temperature including, for example, DMSO, methanol, glycerol, ethylene glycol, propylene glycol, sugars, amino acids, and proteins among others.

In some embodiments, a TelA may be encoded by a nucleic acid sequence that, when transcribed, translated, and/or processed, results in an amino acid sequence having at least 75%, at least 80%, at least 85%, at least 88%, at least 90%, at least 91%, at least 93%, at least 95%, at least 96%, at least 97%, at least 98% or at least 99% identity to one or more of SEQ ID NOS: 1-12. In some embodiments, a variant protelomerase (e.g., a variant TelA) may be encoded by a nucleic acid sequence that, when transcribed, translated, and/or processed, results in an amino acid sequence according to Table 1, for example, an amino acid sequence having at least 75%, at least 80%, at least 85%, at least 88%, at least 90%, at least 91%, at least 93%, at least 95%, at least 96%, at least 97%, at least 98% or at least 99% identity to one or more of SEQ ID NOS:1-12 and including one or more substitutions, insertions and/or deletions relative to SEQ ID NO: 16. A nucleic acid encoding a variant protelomerase (e.g., a variant TelA) may be included in an expression cassette, expression vector, or other expressible form suitable for in vitro or in vivo expression (e.g., in *E. coli* or other bacteria or *P. pastoris* or other yeast). A nucleic acid encoding a TelA may be modified or optimized (e.g., codon optimized) for expression in a desired organism or cell-free expression system.

Kits

The present disclosure further relates to kits including a telomere resolvase (e.g., TelA). For example, a kit may include a telomere resolvase (e.g., TelA) and other enzymes (e.g., other resolvases, enzymes other than resolvases, or both), an example substrate (e.g., a fluorescently labeled DNA having a TelA target site), buffering agents, or combinations thereof. Enzymes may be included in a storage buffer (e.g., comprising glycerol and a buffering agent). A kit may include a reaction buffer which may be in concentrated form, and the buffer may contain additives (e.g. glycerol or a glycerol alternative), salt (e.g. KCl), reducing agent, EDTA or detergents, among others. A kit comprising dNTPs may include one, two, three of all four of dATP, dTTP, dGTP and dCTP. A kit comprising rNTPs may include one, two, three of all four of rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) a telomere resolvase (e.g., TelA); and (ii) a buffer. A telomere resolvase (e.g., TelA) may have a lyophilized form or may be included in a buffer (e.g., a storage buffer or a reaction buffer in concentrated form). A kit may contain a telomere resolvase (e.g., TelA) in a mastermix suitable for receiving and amplifying a template nucleic acid. A telomere resolvase (e.g., TelA) may be a purified enzyme so as to contain substantially no DNA or RNA and no nucleases. The reaction buffer in (ii) and/or storage buffers containing the DNA polymerase in (i) may include non-ionic, ionic e.g. anionic or zwitterionic surfactants and crowding agents. A kit may include a telomere resolvase (e.g., TelA) and the reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g. a CD-ROM, a flash drive). Instructions may be provided remotely using, for example, cloud or internet resources with a link or other access instructions provided in or with a kit.

Methods and Workflows

The present disclosure further provides methods for cleaving and rejoining DNA. A method may comprise, for example, contacting a variant TelA and a variant TelA DNA substrate having a nucleotide sequence comprising at least one copy of SEQ ID NO:16 (and optionally a reaction buffer) to produce a TelA cleavage products. In some embodiments, the molar ratio of variant TelA DNA substrate to variant TelA is ≥2, ≥3, ≥4, ≥5, ≥6, ≥7, ≥8, ≥9, or ≥10. A variant TelA DNA substrate may comprise or may be circular DNA and/or linear DNA. A population of linear DNA substrate molecules may have species having two closed ends, species having one open end and one closed, species having two open ends, or combinations thereof. TelA cleavage products may comprise linear DNA molecules, each with at least one closed end or if the substrate also comprises linear DNA molecules, at least one more closed end per product molecule that the corresponding substrate molecules. For example, a first linear DNA substrate may be ligated to first adapter having a nucleotide sequence comprising at least one copy of SEQ ID NO:16 at one end of the first linear DNA substrate and ligated to a second adapter having a nucleotide sequence comprising at least one copy of SEQ ID NO:16 at the other end of the first linear DNA substrate, thereby forming a first adapter tagged TelA DNA substrate. Contacting this substrate with a variant TelA may produce a linear DNA cleavage product having two closed ends.

A second linear DNA substrate may be ligated to first adapter having a nucleotide sequence comprising at least one copy of SEQ ID NO:16 at one end of the second linear DNA substrate and ligated to a second adapter having a nucleotide sequence lacking SEQ ID NO:16 at the other end of the second linear DNA substrate, thereby forming a second adapter tagged TelA DNA substrate. Contacting this second substrate with a variant TelA may produce a linear DNA cleavage product having one closed end (corresponding to where the copy of SEQ ID NO:16 had been) and one open end (corresponding to the end that had the adapter without SEQ ID NO:16).

EXAMPLES

Some specific example embodiments may be illustrated by one or more of the examples provided herein.

Example 1: Small-Scale Ni Beads Purification of ΔN105/D97X Variants

D97X variant proteins were purified from 15-30 mL IPTG-induced cells. T7 expression cells (15-30 mL) C2566 carrying D97X variants were grown to late log phase, and cells were cooled down at room temperature (r.t.) for 30 min. IPTG was added to a final concentration of 0.5 mM and IPTG induction was carried out at 18° C. overnight (~20 h). Cells were pelleted at 4° C. and resuspended in 1 mL of cell lysis buffer (50 mM NaH$_2$PO$_4$, 0.3 M NaCl, 10 mM imidazole, adjusted pH to 7.4 with NaOH). Cells were lysed by sonication (small sonication tip, 3 times with 15 sec burst) while tubes were sitting on ice. Cell debris was removed by centrifugation at 14,000 g for 15 min. Clarified lysates were mixed with 100 mL of Ni magnetic beads (prewashed with cell lysis buffer) and further mixed in a roller for 1 h at 4° C. Eppendorf tubes with beads and lysates were placed in a magnet and the beads were attached to the side of the magnet. Lysates were removed by 1 mL pipette and 1 mL of fresh wash buffer (50 mM NaH$_2$PO$_4$, 0.3 M NaCl, 20 mM imidazole, adjusted pH to 7.4 with NaOH) was added to each tube. After three rounds of washing, the D97X variant proteins were eluted by addition of 200 mL of elution buffer (50 mM NaH$_2$PO$_4$, 0.3 M NaCl, 250 mM imidazole, adjusted pH to 7.4 with NaOH) by gently inverting the test tube and placed the tubes onto magnet. Eluted proteins were mixed with equal volume of glycerol. After measuring the protein concentration, each variant protein was diluted to 90-100 ng/μl (90-100 mg/mL) in an enzyme storage buffer (0.2 M NaCl, 20 mM Tris-HCl, pH 7.5, 10 mM DTT, 50% glycerol, 0.5 mM EDTA), and kept at −20° C. for next step activity assays.

Figure 3A:
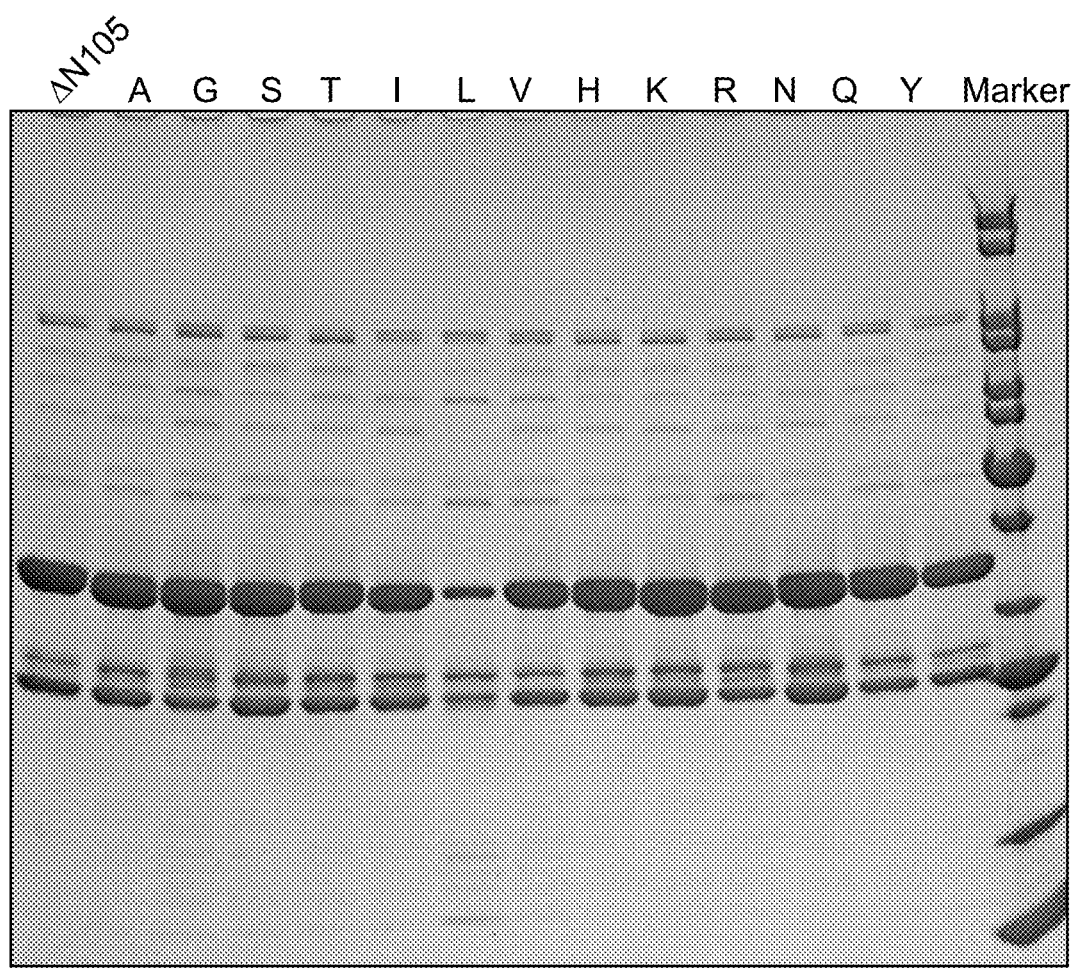
FIG. 3A shows an example small-scale purification of TelA variants (ΔN105/D97X) by Ni magnetic beads. Leftmost lane contained TelA variant including a 105-amino acid N-terminal deletion. Letters marking the other lanes indicate the amino acid included in place of D97 (e.g. A=D97A, K=D97K) in addition to the N-terminal deletion. D97P variant was not purified since previous experiment showed that D202P in full-length background had significant decrease in activity. The protein yield of D97L was much reduced. The rest of the D97X mutants showed comparable expression level as compared to ΔN105/D97. The predicted molecular mass of 6×His tagged D97X variants is ~38.8 kDa (344 aa) while the apparent MW was ~36 kDa.

Results are shown in FIG. 3A. A D97P variant was not purified for this example since some experimental work showed that D202P in full-length background was observed to have a notable drop in activity. Protein yield of D97L was reduced. The rest of the D97X variants showed comparable expression level as compared to ΔN105/D97. The predicted molecular weight of 6×His tagged D97X variants is ~38.8 kDa (344 aa). The amino acid substitution in each variant (e.g. A=D97A, K=D97K) is indicated on top of the protein gel.

Example 2: Purification of TelA Variants

Cell cultures (2 L) expressing the TelA of interest were grown to mid-log phase were induced with 0.4 mM IPTG at 18° C. overnight. Cell pellets were resuspended in 60 mL of cell lysis buffer (50 mM NaH$_2$PO$_4$, 0.3 M NaCl, adjusted pH to 7.4 with NaOH) in a 100 mL metal beaker. Cells were lysed by sonication using a medium tip (30 sec bursts for 20 times) on ice. Cell debris was removed by centrifugation at 15,000 g for 30 min. The clarified lysate was loaded onto a Ni-agarose column (12 mL) prewashed with cell lysis buffer by gravity flow. The protein binding/loading step was repeated three times to maximize protein binding to the Ni agarose resin. After extensive washing with 150 mL of wash buffer (30 mL×5, 50 mM NaH$_2$PO$_4$, 0.3 M NaCl, 5 mM imidazole, adjusted pH to 7.4 with NaOH), the 6×His-tagged TelA variant was eluted in 22.5 mL (7.5 mL×3) of elution buffer 50 mM NaH$_2$PO$_4$, 0.3 M NaCl, 250 mM imidazole, adjusted pH to 7.4 with NaOH). Protein concentration was determined by OD$_{280}$ reading on a Nanodrop machine.

Subsequent chromatography steps included DEAE, heparin, and SP-HP columns, in each case, using corresponding loading, washing, and elution buffers. Eluted protein was dialized into storage buffer (50% glycerol, 300 mM NaCl, 20 mM Tris pH 7.4, 0.1 mM EDTA, 1 mM DTT).

Figure 3B:
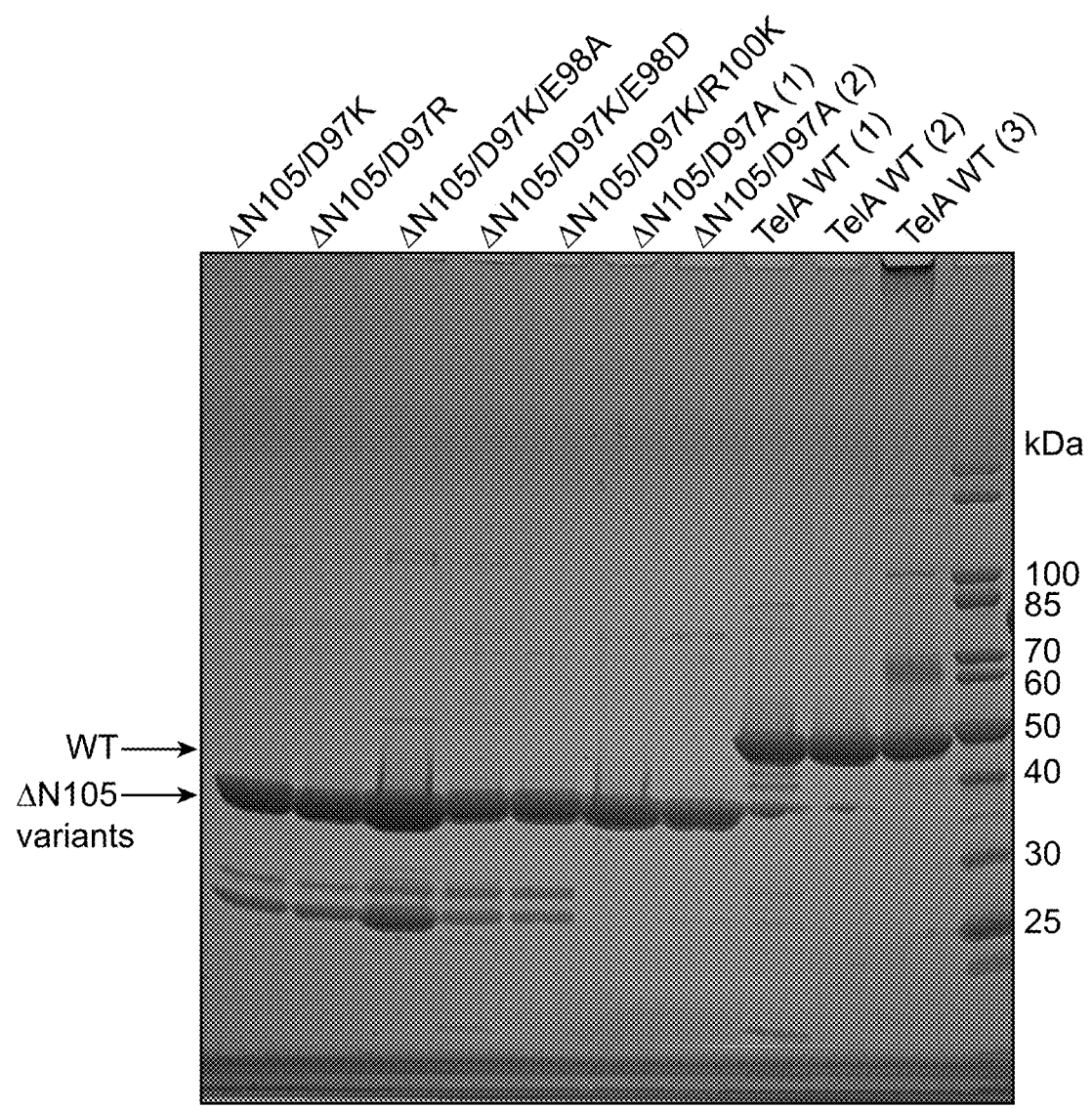
FIG. 3B shows example results of purification of TelA WT enzyme and TelA variants in ΔN105 deletion background.

Results are shown in FIG. 3B. Most of the WT and mutants were purified by chromatography through three columns as described here, except ΔN105/D97A (1) which was purified via more columns. The WT enzyme in Heparin purifications step was eluted in two major peaks, probably reflecting two different oligomerization state (monomer and dimer). Enzymes eluted in both peaks are active in cleaving duplex oligos with a TelA site. Lanes marked TelA WT (1) and TelA WT (2) were derived from the major peak elution of two independent preparations and TelA WT (3) was pooled from the minor peak elution.

Example 3: Protelomerase Activity Assay

Figure 4:
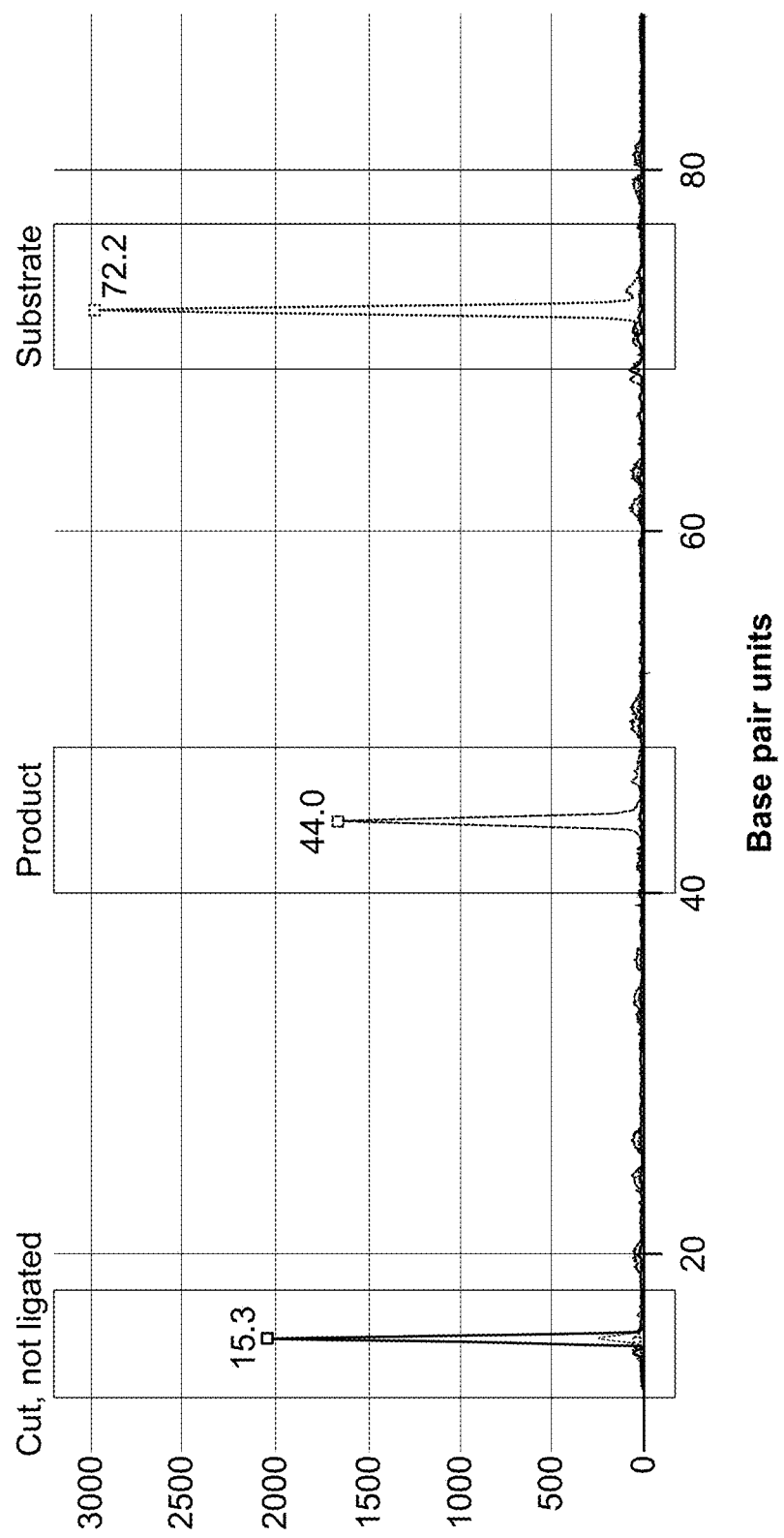
FIG. 4 shows results for example capillary electrophoresis (CE) assays using TelA-treated, FAM labeled substrates after heating at 95° C. for 10 min. FAM-labeled DNA Substrate=right peak, hairpin product with 2 orphan bases=center peak, and product with 6-nt 5' overhang (cut-only; not ligated)=left peak.

Activity assays were performed with reaction conditions described here using a 5' FAM-labeled oligo substrate according to SEQ ID NO:22. Products were analyzed by capillary electrophoresis. Nearly equal amounts of two DNA strands were mixed together in PCR tube (5% slight access of unlabeled strand) in TE buffer and heated at 95° C. for 5 min, and gradually cooled down to r.t. The duplex oligos were diluted to 1250 nM as a stock substrate. 1 μL of duplex oligos (25 nM), 1 μL of TelA variant enzyme (95 ng/mL and 47.5 ng/mL), 5 μL of 10× ThermoPol buffer, 43 μL of TE, were mixed in an Eppendorf tube and incubated at 30° C. for 30 min. 5 μL of 1% SDS was added to the tube to stop the enzyme reaction. The reacted substrate/product was diluted 5-fold in 0.1% SDS and analyzed by capillary electrophoresis (CE) assay. The untreated substrate and cut-only oligos (not ligated with hairpin) were used as controls for the CE assay. Example peaks observed in the CE assay are shown in FIG. 4.

TABLE 2 shows example results of a D97X variant activity assays using fluorescent duplex oligos and proteins purified according to EXAMPLE 1. D97K, D97R, and D97Q showed enhanced activity compared to D97A and ΔN105/D97. D97H also showed small increase in activity. Each variant tested displated a "cut only" of 0%.

TABLE 2

| D97X Variant | Product | Substrate |
| --- | --- | --- |
| ΔN105 | 7.72% | 92.28% |
| G | 41.63% | 58.37% |
| A | 62.95% | 37.05% |
| S | 55.80% | 44.20% |

TABLE 2-continued

| D97X Variant | Product | Substrate |
| --- | --- | --- |
| T | 53.49% | 46.51% |
| V | 36.58% | 63.42% |
| I | 40.54% | 59.46% |
| R | 91.14% | 8.86% |
| H | 66.26% | 33.74% |
| K | 92.73% | 7.27% |
| N | 61.39% | 38.61% |
| Q | 75.15% | 24.85% |
| L | 0% | 100.00% |
| Y | 29.54% | 70.46% |
| Wild Type | 28.00% | 72.00% |
| D202A | 4.87% | 95.13% |

Example 4: Impact of Buffer Composition on Wild Type and Variant TelA Activity

Figure 5:
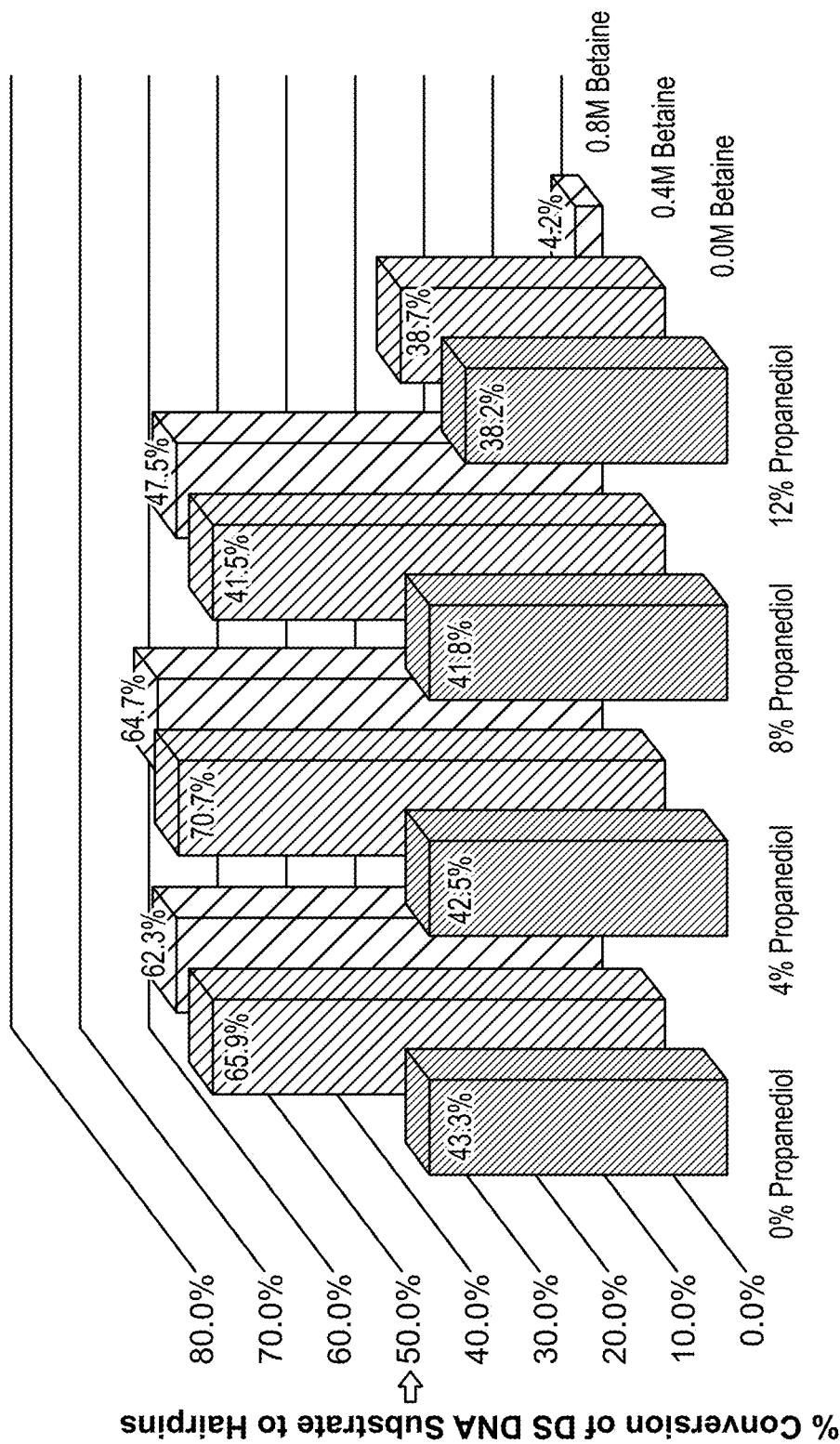
FIG. 5 shows results of an example protelomerase activity assay in which the wild type enzyme was incubated with a model substrate at a ratio of 0.5:1 in a ThermoPol® reaction buffer having 0%, 4%, 8% or 12% propanediol (w/v) and 0.0M, 0.4M, or 0.8M betaine. Under the conditions tested, the best results were observed with buffer containing 4% propane and 0.4M betaine.

Conversion of substrate (FAM-labeled linear dsDNA) to product (closed end hairpin) by WT TelA (D202) was monitored using 50 μL reactions in Thermopol buffer incubated at 30° C. for 60 minutes prior to quenching by SDS, dilution, and resolution by capillary electrophoresis. Substrate was provided in excess (2:1) over the enzyme and the arrow on the Y-axis indicates the expected % product formation if the reaction is stoichiometric. Supplementation with betaine (0.4M or 0.8 M) or propanediol (4% or 8%) was compared to reactions without supplementation. Higher % conversion by the combinations of betaine and propanediol are suggestive of enzyme turnover. Results are shown in FIG. 5.

Example 5: Activity of Wildtype TelA and Variants with Detergents

Figure 6:
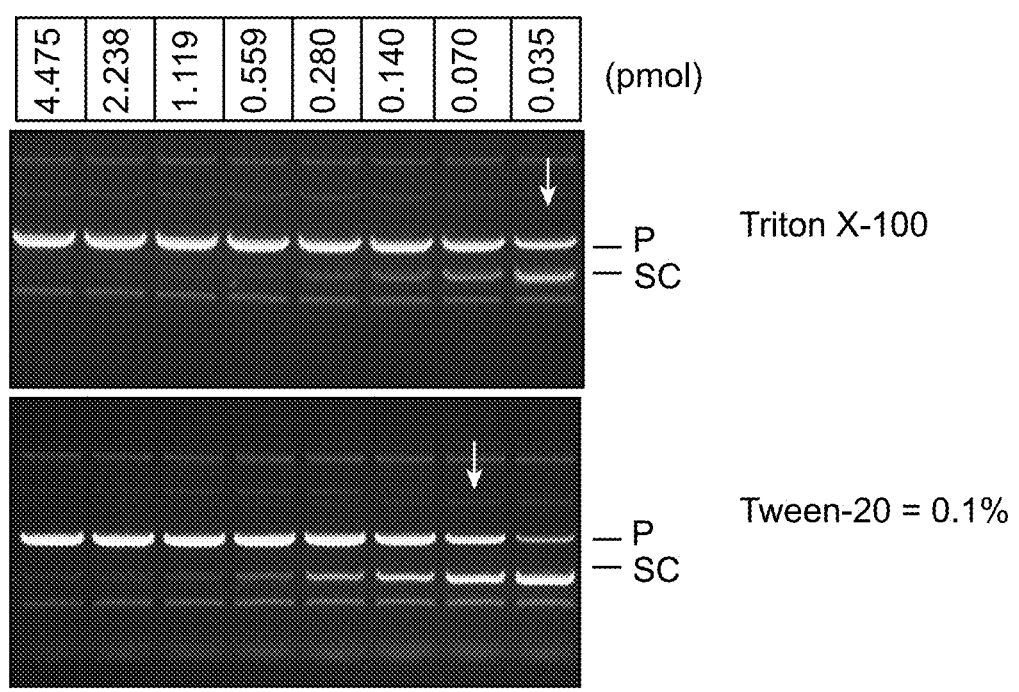
FIG. 6 shows results of an example protelomerase activity assay for a variant TelA (ΔN105/D97K) in the presence of Triton™ X-100 and Tween™ 20.

A protelomerase activity assay was performed in accordance with EXAMPLE 3 except that the detergent in the ThermoPol buffer was replaced with Triton X-100 (octoxinol-9) or Tween 20 (polysorbate20). Results are shown in FIG. 6. As shown, similar amounts of the variant enzyme were capable of converting 0.15 pmol supercoiled DNA to linear DNA with different non-ionic detergents, demonstrating that Triton X-100 contained in ThermoPol buffer may be replaced by another non-ionic detergent, namely, Tween 20. Arrow indicates the amount of enzyme required to convert supercoil DNA to linear DNA.

Example 6: Activity of a TelA Variant with a Detergent and an Amino Acid Salt

Figure 7:
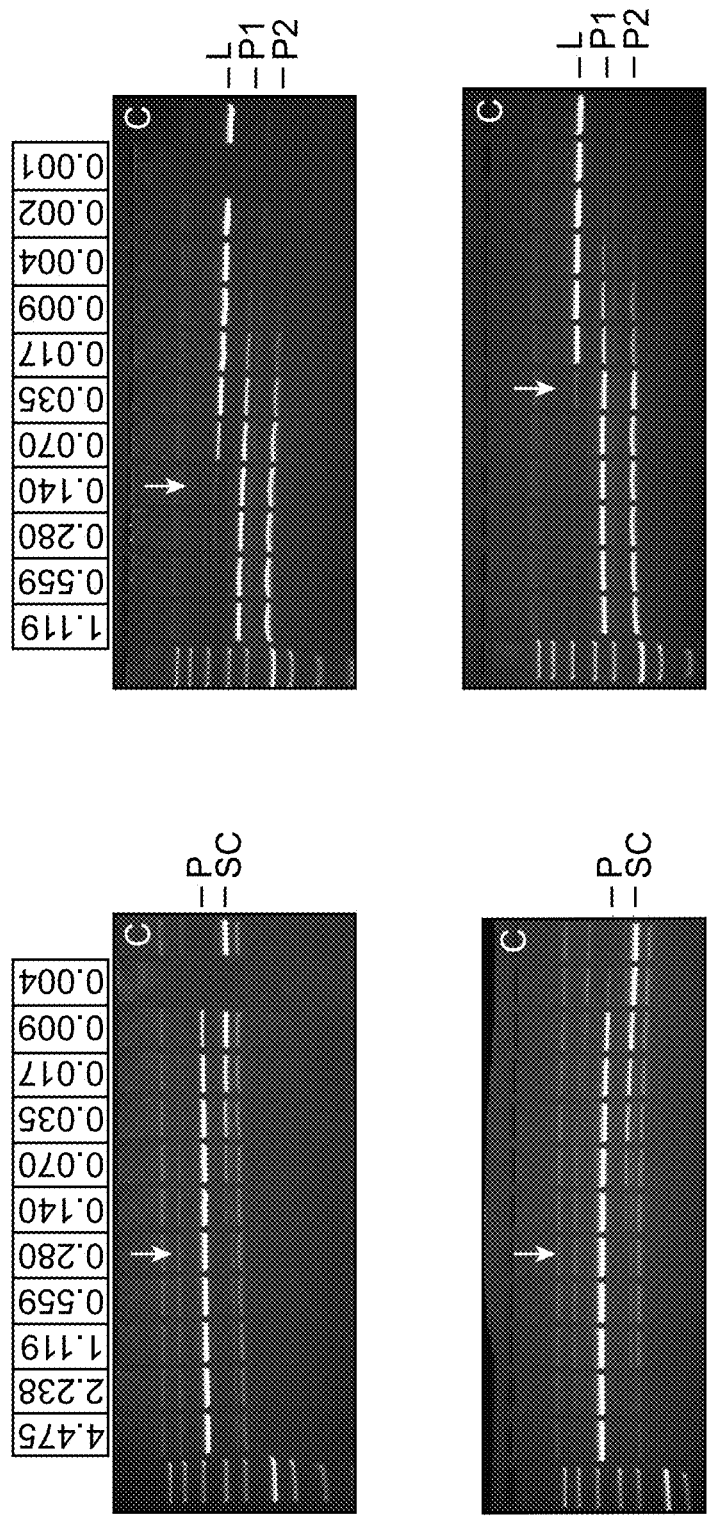
FIG. 7 shows results of an example protelomerase activity assay for a variant TelA. Indicated amounts of variant TelA (ΔN105/D97K) in picomoles were incubated with 0.15 pmol of supercoiled DNA (upper and lower left gels) or linear DNA (upper and lower right gels) at 30° C. for 30 min (left and right upper gels) or 16 hours (left and right lower gels) followed by 80° C. for 10 min in ThermoPol (DF) buffer (NEB #B9013) with a detergent and an amino acid salt. Arrows indicate the amounts of enzymes required to convert 95% of substrates ("SC" or "L") to designated products ("P2" or "P" and "P1"). Lanes marked "C" show results without enzyme.

A protelomerase activity assay was performed in accordance with EXAMPLE 3 and results are shown in FIG. 7.

Indicated amounts of variant TelA (ΔN105/D97K) in picomoles were incubated with 0.15 pmol of supercoiled DNA (upper and lower left gels) or linear DNA (upper and lower right gels) at 30° C. for 30 min (left and right upper gels) or 16 hours (left and right lower gels) followed by 80° C. for 10 min in ThermoPol (DF) buffer (NEB #B9013) with a detergent and an amino acid salt. Arrows indicate the amounts of enzymes required to convert 95% of substrates ("SC" or "L") to designated products ("P2" or "P" and "P1"). Lanes marked "C" show results without enzyme. The same amount (0.28 μmol) of ΔN105/D97K was required to convert supercoiled substrate to product regardless of whether reactions were stopped after 30 minutes or 16 hours suggesting little or no enzymatic turnover under the conditions tested. However, only 0.035 pmol of the variant enzyme were required to convert a linear substrate over 16 hours compared to 0.14 pmol required for a 30 min reaction, suggesting the enzyme may turn-over with linear DNA. Under the conditions tested, observed turnover was higher for linear DNA than supercoiled DNA.

Example 7: Activity of TelN in MOPS and ThermoPol Buffers

Figure 8:
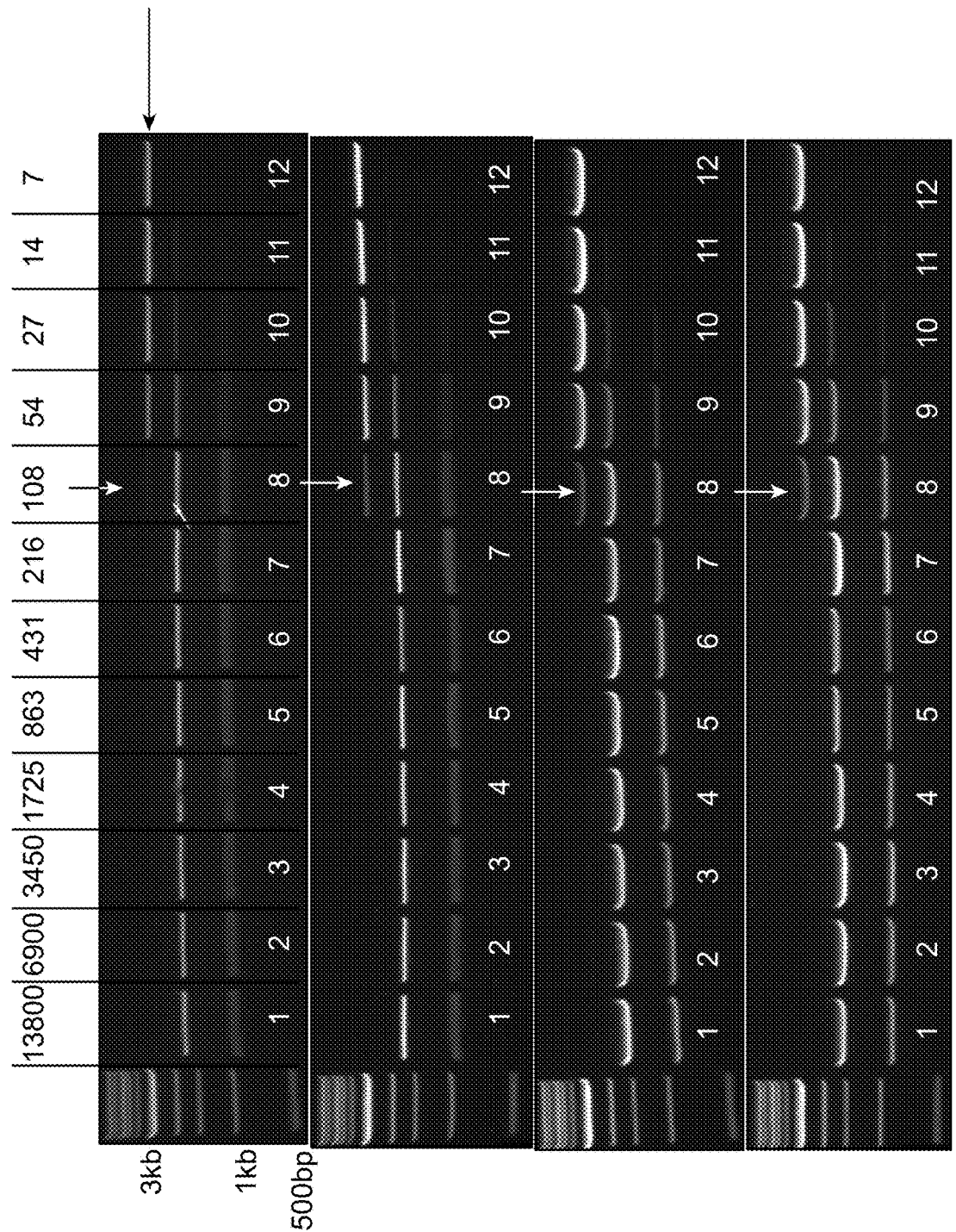
FIG. 8 shows results of an example protelomerase activity assay for TelN. Indicated amounts of TelN (fmoles) were incubated with 120 fmoles of linear DNA at 30° C. for 30 min (top gel and third from top gel) or overnight (second from top gel and bottom gel) followed by 80° C. for 10 min in MOPS buffer (top and second from top gels) or ThermoPol buffer (third from top gel and bottom gel). Arrows indicate the amounts of enzymes required to convert 95% of substrates to products. Arrow indicates undigested initial substrate.

In light of results with TelA D97K and wild-type TelN on supercoiled substrates, a protelomerase activity assay was performed in accordance with EXAMPLE 3 to assess performance with linear substrates. Results are shown in FIG. 8. Indicated amounts of TelN (fmoles) were incubated with 120 fmoles of linear DNA at 30° C. for 30 min (top gel and third from top gel) or overnight (second from top gel and bottom gel) followed by 80° C. for 10 min in MOPS buffer (top and second from top gels) or ThermoPol buffer (third from top gel and bottom gel). Arrows indicate the amounts of enzymes required to convert 95% of substrates to products. Arrow indicates undigested initial substrate. The same amount of TelN (108 fmoles) is required for conversion regardless of whether reactions are stopped after 30 minutes or incubation overnight. These results are inconsistent with TelN having a turnover number exceeding 1.

Example 8: Activity of a TelA Variant in MOPS and ThermoPol Buffers

Figure 9:
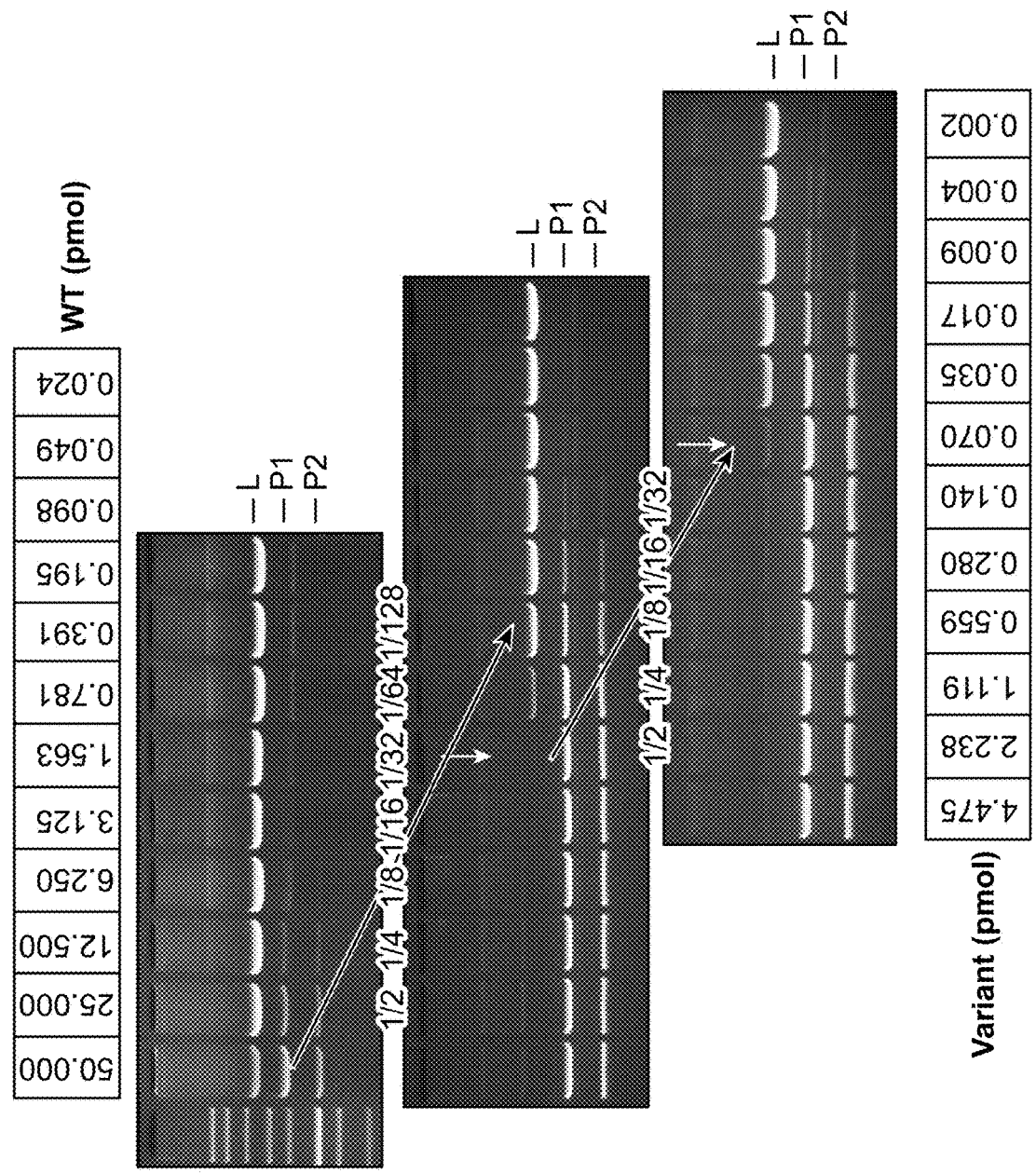
FIG. 9 shows results of an example protelomerase activity assay for TelA. Indicated amounts of wild type TelA (upper and middle gel) or variant TelA (ΔN105/D97K; bottom gel) were incubated with 0.15 pmol of linear DNA at 30° C. for 30 min followed by 80° C. for 10 min in ThermoPol buffer (upper gel), ThermoPol buffer with an amino acid salt (middle gel and bottom gel). Arrows indicate the amounts of enzymes required to convert 95% of substrates to products.

A protelomerase activity assay was performed in accordance with EXAMPLE 3 and results are shown in FIG. 9.
Indicated amounts of wild type TelA (upper and middle gel) or variant TelA (ΔN105/D97K; bottom gel) were incubated with 0.15 pmol of linear DNA at 30° C. for 30 min followed by 80° C. for 10 min in ThermoPol buffer (upper gel), ThermoPol buffer with an amino acid salt (middle gel and bottom gel). Arrows indicate the amounts of enzymes required to convert 95% of substrates to products. Wild type enzyme achieved 50% substrate cleavage at a protein: enzyme ratio of 333 without an amino acid salt (upper gel) and a ratio of 2.6 in the presence of an amino acid salt (middle gel) representing a 32-fold increase in activity (line connecting top and middle gels). Variant TelA (ΔN105/D97K) achieved 50% substrate cleavage at a protein:enzyme ratio of 0.23 representing a 10-fold increase over wild type (line connecting middle and bottom gels).

Example 9: Preparation of RCA-Amplified Concatemers DNA with a TelA Site

Figure 10:
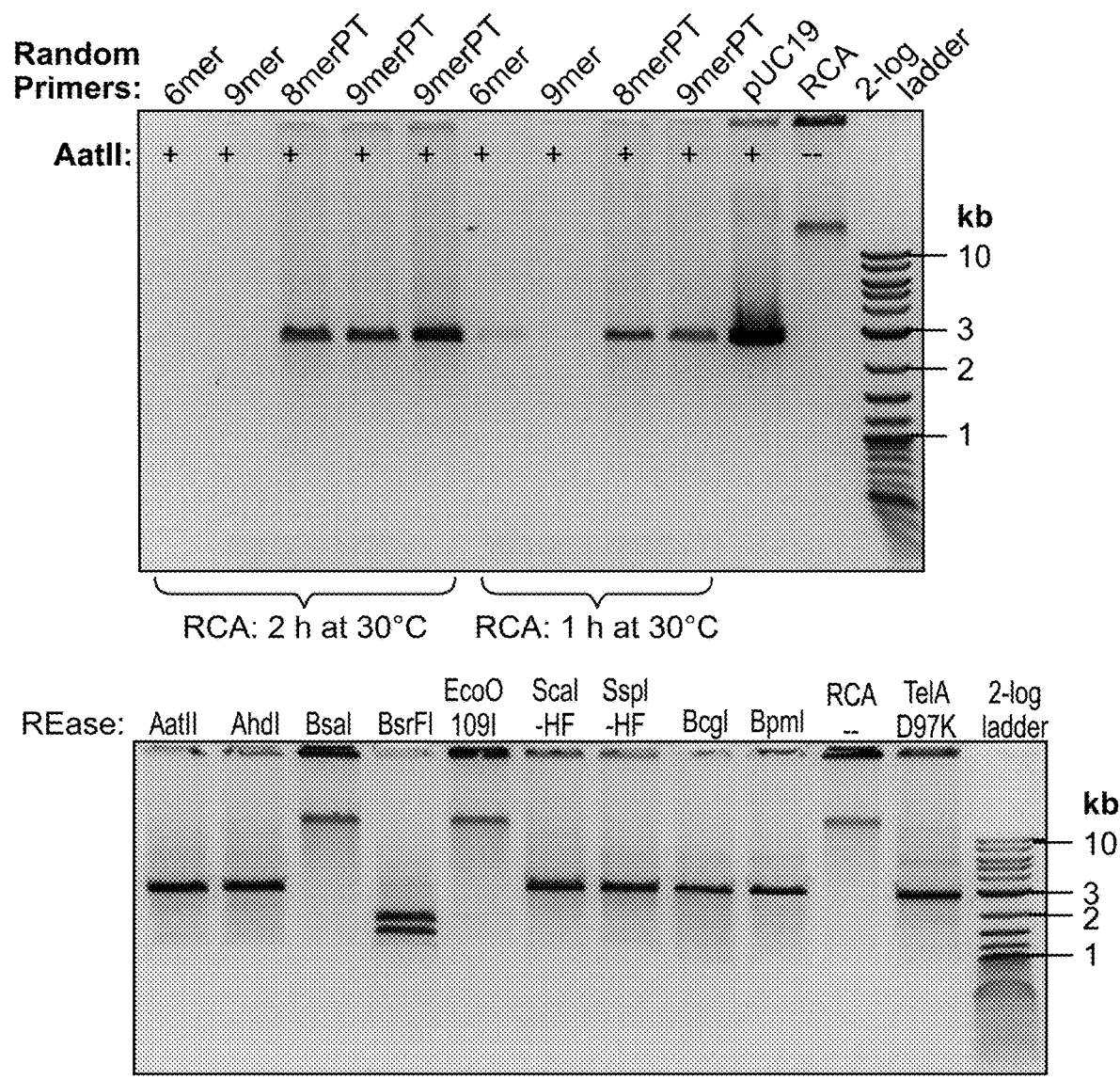
FIG. 10 shows example results of preparation of an RCA-amplified TelA substrate.

A pUC19 derivative containing a 26 bp TelA target site was amplified by phi 29 DNA polymerase and phosphorothioated (PT) random primers (unmodified hexamer, 9mer, 8merPT, 5' NNNNNN*N*N 3', or 9merPT, 5' NNNNNNN*N*N 3'. * indicates phosphorothioate (PT) modified site) at 30° C. for 1-2 h. 2 µg RCA-amplified DNA was digested by individual restriction enzymes or TelA D97K. Cleavage products were analyzed by agarose gel electrophoresis. Unmodified hexamer and 9mer worked poorly in RCA due to the strong exonuclease activity of the phi 29 DNA polymerase. 8merPT and 9merPT random primers worked efficiently (top panel). The RCA amplified DNA was digested by individual restriction enzymes as indicated on the top of each lane. AatII, AhdI, ScaI-HF, SspI-HF, BcgI, and BpmI digested the RCA DNA and generated a unit length plasmid DNA (~2.8 kb, bottom panel). Results are shown in FIG. 10.

Example 10: Activity of TelA Variant on RCA Amplified DNA

Figure 11:
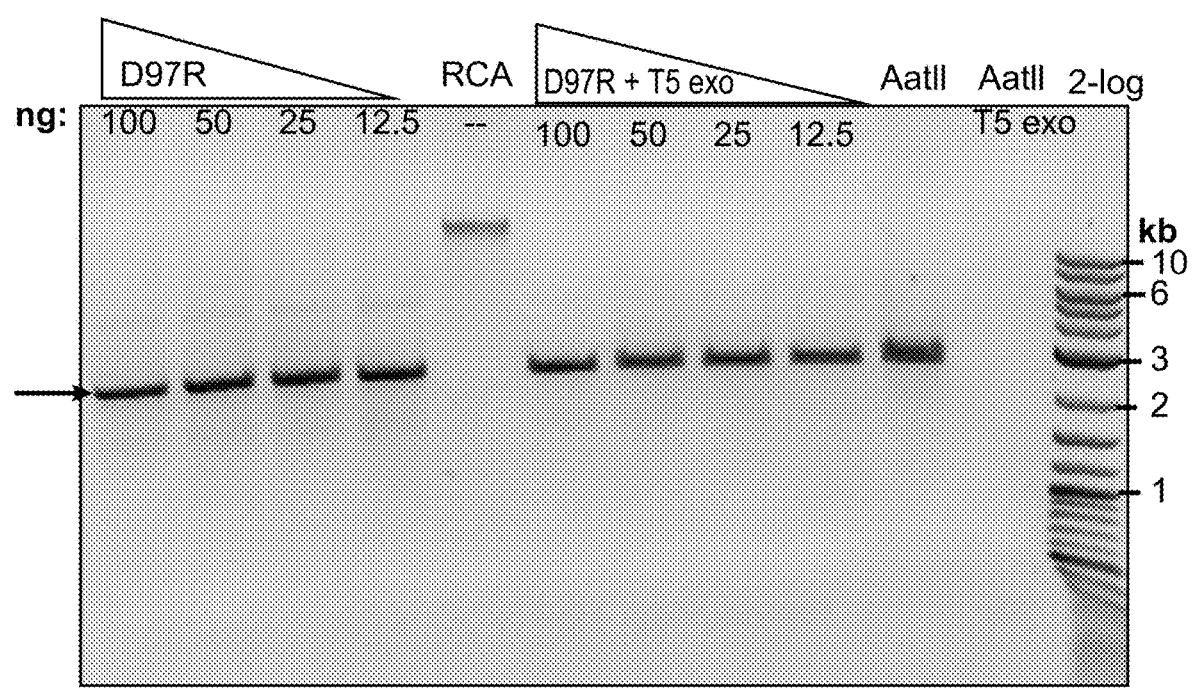
FIG. 11 shows results of an example protelomerase activity assay for TelA variants on RCA-amplified DNA.
Figure 12:
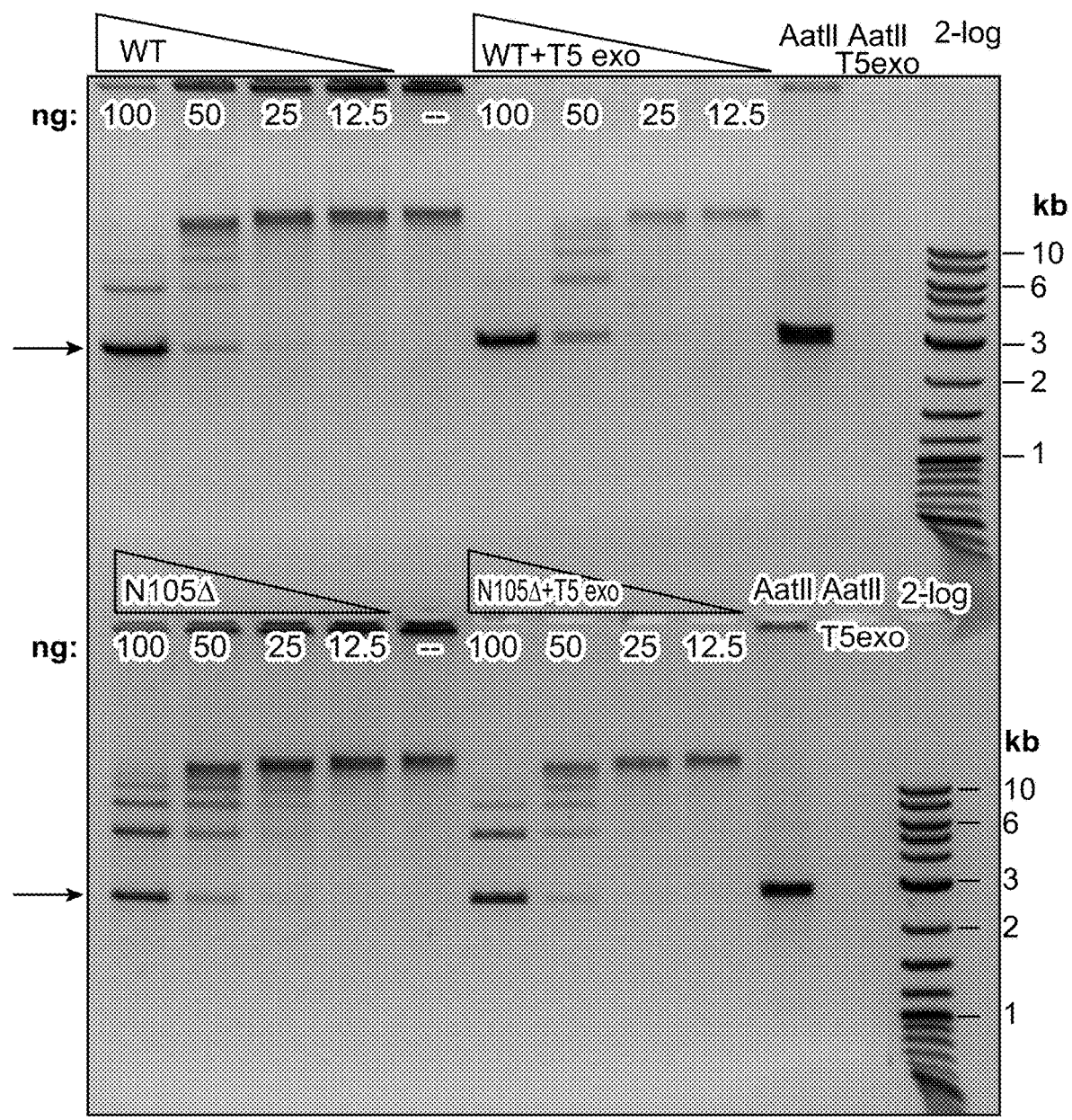
FIG. 12 shows results of an example protelomerase activity assay of purified wild type TelA on RCA-amplified DNA (upper gel) and shows results of an example protelomerase activity assay of purified variant TelA (ΔN105) on RCA-amplified DNA (lower gel).

A protelomerase activity assay was performed in accordance with EXAMPLE 3 and results are shown in FIG. 11, FIG. 12A, and FIG. 12B.
With respect to FIG. 11, variant TelA (ΔN105/D97R) was diluted in enzyme storage buffer to 50, 25, 12.5, 6.75 ng/4 and 2 µL of the diluted enzyme was used to digest 2 µg of RCA-amplified concatemer DNA. The single unit length plasmid DNA is expected to be ~2.8 kb as indicated by an arrow. AatII and AatII+T5 exonuclease (exo) served as controls (AatII digested cohesive ends were susceptible to exonuclease digestion while the D97R treated DNA was resistant to T5 exonuclease digestion). 2-log, DNA size marker in 0.1-10 kb (NEB). The specific activity was estimated at 40,000-80,000 U/mg protein for ΔN105/D97R.
With respect to FIG. 12A and FIG. 12B, TelA proteins were diluted in enzyme storage buffer to 100, 50, 25, 12.5, ng/4 and 2 µL of the diluted enzyme was used to digest 2 µg of RCA-amplified concatemer DNA. The single unit length plasmid DNA is expected to be ~2.8 kb as indicated by an arrow. AatII and AatII+T5 exonuclease (exo) served as control digests (AatII digested cohesive ends were susceptible to exonuclease digestion, while the WT and ΔN105-treated DNA was resistant to T5 exonuclease digestion). 2-log, DNA size marker in 0.1-10 kb (NEB). The specific activity of the WT enzyme and the N-terminal deletion mutant ΔN105 was estimated at 5000 to 10,000 U/mg protein. 1 unit of enzyme is defined as the amount of enzyme required to complete 95% telomere resolution (cleavage and ligation) of 1 µg of RCA amplified DNA in 60 min at 30° C. followed by T5 exonuclease treatment for 30 min at 30° C. T5 exonuclease digestion eliminated the non-specifically amplified DNA and linear (unprotected) DNA.

Example 11: Activity of TelA Variants on RCA Amplified DNA

Figure 13:
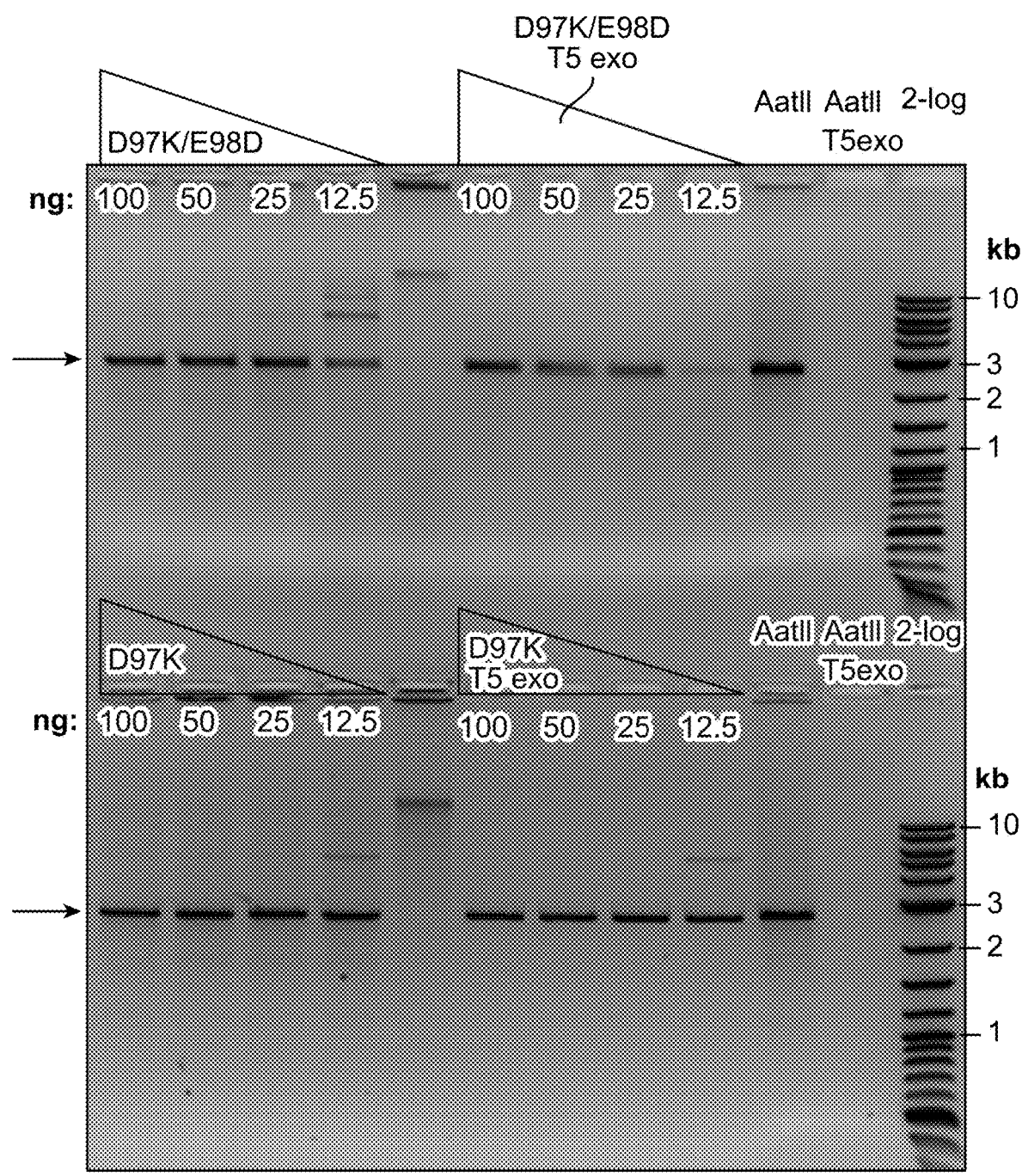
FIG. 13 shows results of an example protelomerase activity assay of variant TelA (ΔN105/D97K/E98D) on RCA-amplified DNA (upper gel) and shows results of an example protelomerase activity assay of another variant TelA (ΔN105/D97K) on RCA-amplified DNA (lower gel).

A protelomerase activity assay was performed in accordance with EXAMPLE 11 and results are shown in FIG. 13A and FIG. 13B.
TelA mutant proteins were diluted in enzyme storage buffer to 50, 25, 12.5, 6.25 ng/4 and 2 µL of the diluted enzyme was used to digest 2 µg of RCA-amplified concatemer DNA. The single unit length plasmid DNA is expected to be ~2.8 kb as indicated by an arrow. AatII and AatII+T5 exonuclease (exo) served as control digests (AatII digested cohesive ends were susceptible to exonuclease digestion, while the ΔN105/D97K and ΔN105/D97K/E98D treated DNA was resistant to T5 exonuclease digestion). 2-log, DNA size marker in 0.1-10 kb (NEB). The specific activity was estimated at 40,000 U/mg protein for the two mutants as compared to the WT enzyme (10,000 U/mg).

Example 12: Activity of TelA Variants on RCA Amplified DNA

Figure 14:
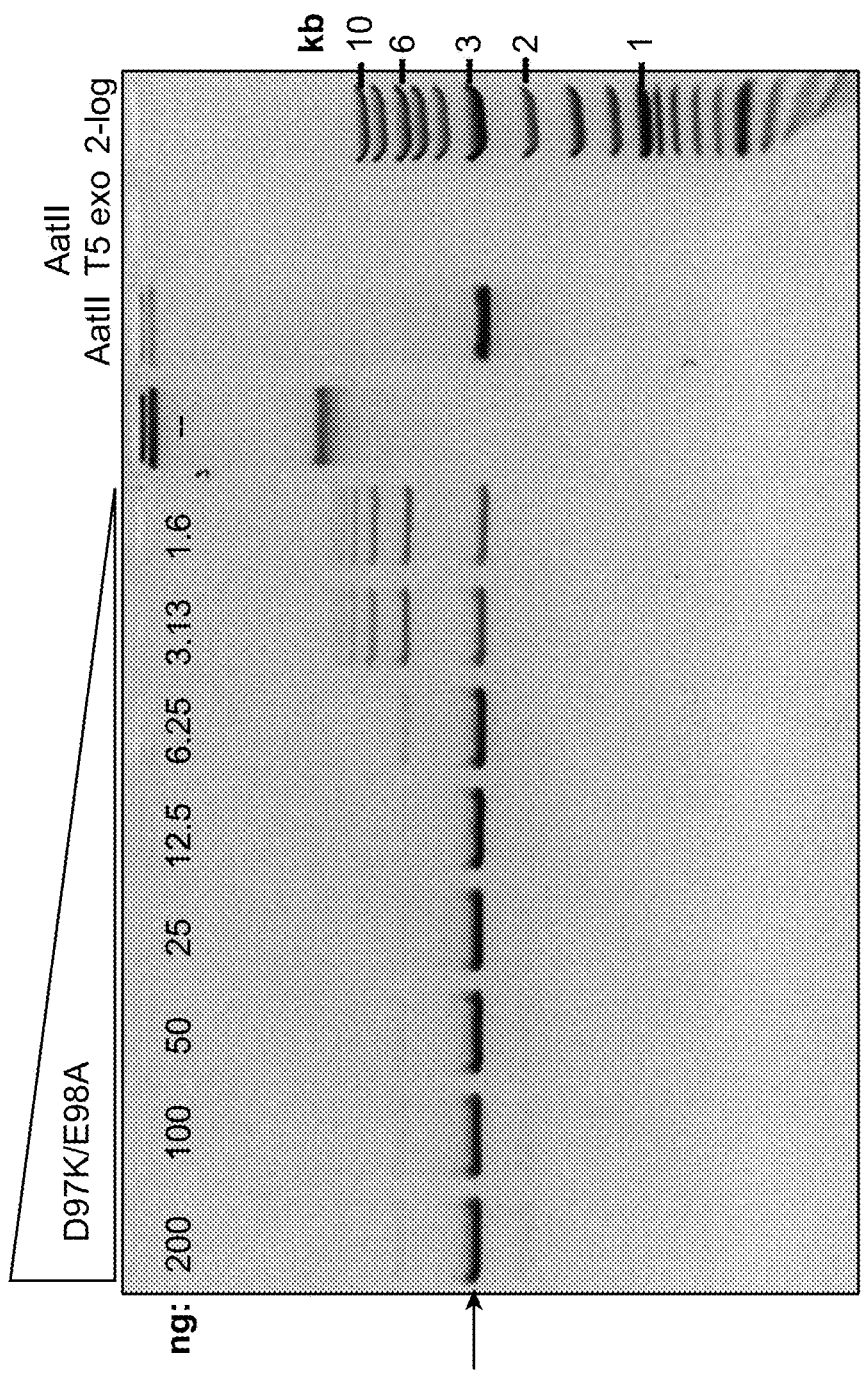
FIG. 14 shows results of an example protelomerase activity assay for variants ΔN105/D97A (bottom panel), ΔN105/D97K/E98D (bottom panel), ΔN105/D97K/R100H (top panel), ΔN105/D97K/E98D/R100K (top panel) on RCA-amplified concatemers DNA.

A protelomerase activity assay was performed in accordance with EXAMPLE 11 and results are shown in FIG. 14.
Variant TelA protein (ΔN105/D97K/E98A) was diluted in enzyme storage buffer to 100 to 0.8 ng/4 and 2 µL of the diluted enzyme was used to digest 2 µg of RCA-amplified concatemer DNA. The single unit length plasmid DNA is expected to be ~2.8 kb as indicated by an arrow. AatII and AatII+T5 exonuclease served as control digestions (the AatII-digested unit length linear DNA with cohesive ends are not protected and therefore degraded by T5 exonuclease treatment while ΔN105/D97K/E98A treated DNA was resistant to T5 exonuclease digestion). 2-log, DNA size marker in 0.1-10 kb (NEB). The specific activity was estimated at 80,000 U/mg protein for the double mutant ΔN105/D97K/E98A, which is more active than the single mutant ΔN105/D97K (40,000 U/mg). 1 unit of enzyme is defined as the amount of enzyme required to complete 95% telomere resolution (cleavage and ligation) of 1 μg of RCA amplified DNA in 30-60 min at 30° C. followed by T5 exonuclease treatment for 30 min at 30° C.

Example 13: Activity of TelA Variants on RCA Amplified DNA

Figure 15:
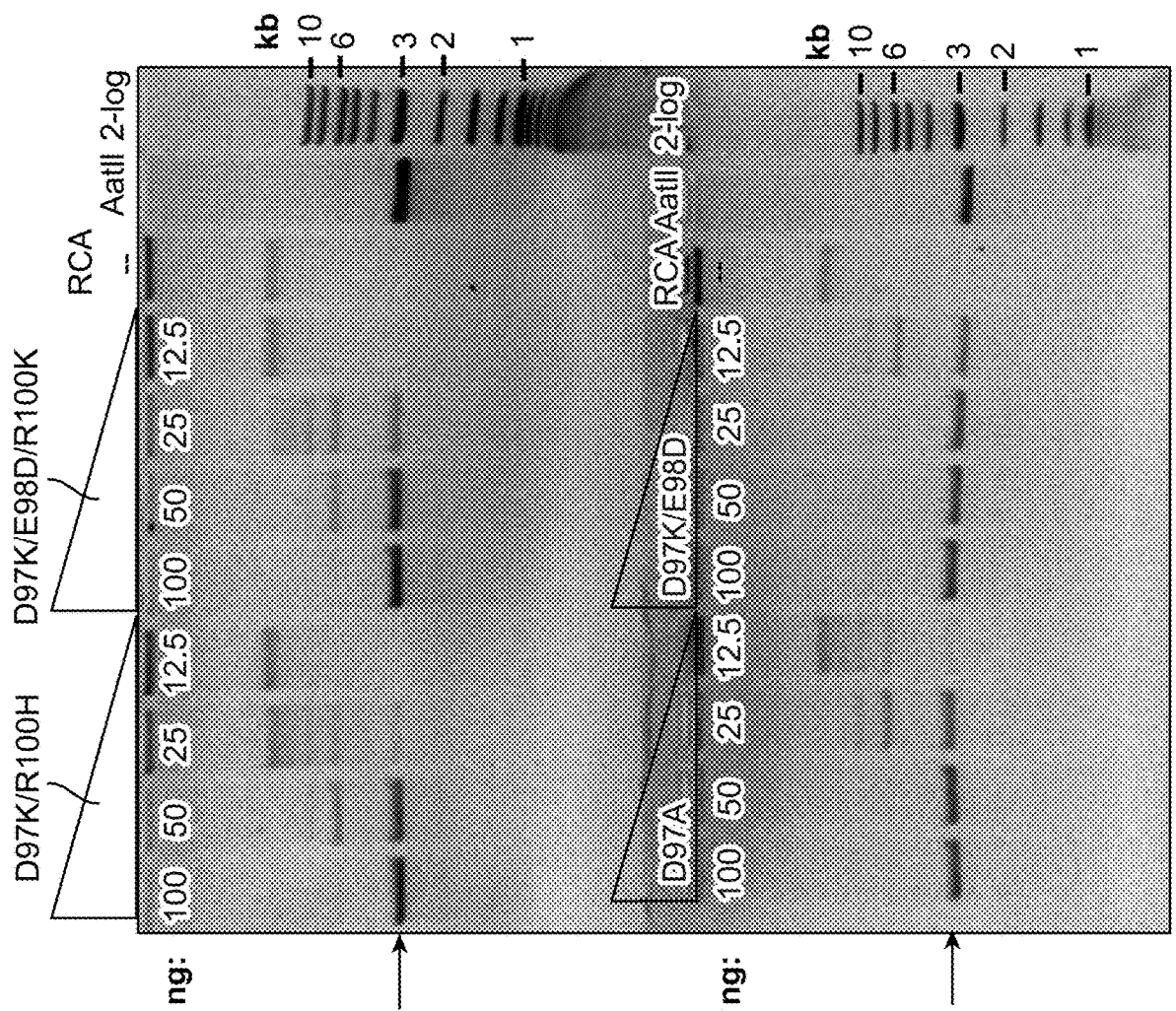
FIG. 15 shows results of an example protelomerase activity assay for a variant TelA (ΔN105/D97K/E98A).

A protelomerase activity assay was performed in accordance with EXAMPLE 11 and results are shown in FIG. 15.

TelA mutant proteins were diluted in enzyme storage buffer to 50, 25, 12.5, 6.25 ng/4 and 2 μL of the diluted enzyme was used to digest 2 μg of RCA-amplified concatemer DNA. The single unit length plasmid DNA is expected to be ~2.8 kb as indicated by an arrow. AatII served as a control digest. 2-log, DNA size marker in 0.1-10 kb (NEB). The specific activity was estimated at 20,000 U/mg protein for ΔN105/D97A, 40,000 U/mg protein for ΔN105/D97K/E98D, 10,000 U/mg protein for the triple mutant ΔN105/D97K/E98D/R100K.

Figure 16:
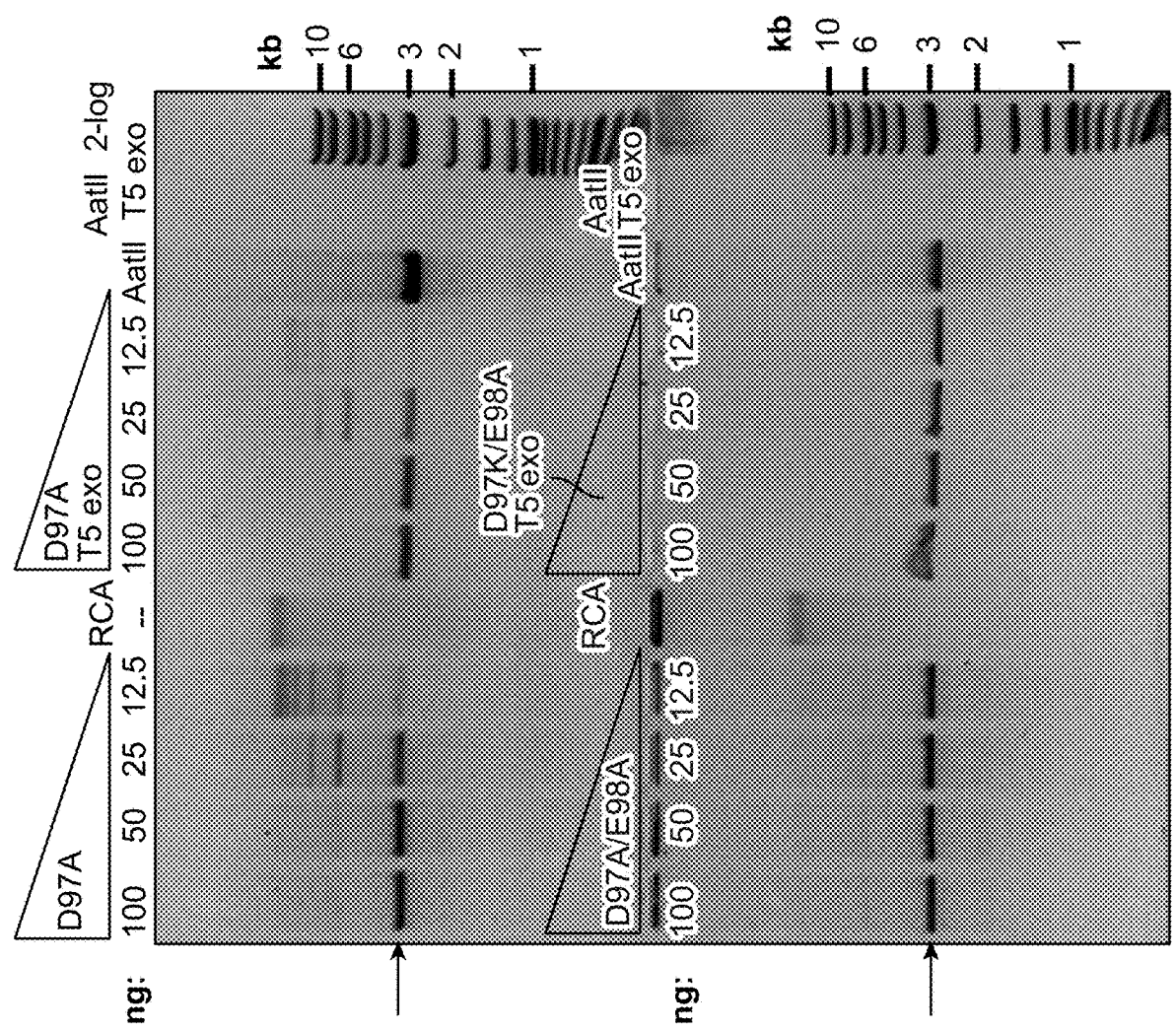
FIG. 16 shows results of an example protelomerase activity assay for two variants of TelA, namely, ΔN105/D97A (upper gel) and ΔN105/D97K/E98A (lower gel).

Due to the multiple pipetting steps and small amount of substrate DNA and diluted proteins and other variables (e.g. temperature, shaker speed) in the activity assay, a repeat experiment was carried out to define the units of variant ΔN105/D97A and variant ΔN105/D97K/E98A to see whether the result was reproducible. Results from the repeat experiment are shown in FIG. 16. TelA mutant protein was diluted in enzyme storage buffer to 50, 25, 12.5, and 6.25 ng/4 and 2 μL of the diluted enzyme was used to digest 2 μg of RCA-amplified concatemer DNA. The single unit length plasmid DNA is expected to be ~2.8 kb as indicated by an arrow. AatII and AatII+T5 exonuclease served as controls (the AatII-digested unit length linear DNA with cohesive ends was not protected and therefore degraded by T5 exonuclease treatment). The specific activity was estimated at 20,000 U/mg protein for ΔN105/D97A and 80,000 U/mg for the double mutant ΔN105/D97K/E98A. It was concluded that the results were reproducible in the unit definition. T5 exonuclease treatment removed the background smearing and a few weak non-specific bands.

Specific activity results for variants tested are shown in Table 3. Note: the unit definition on RCA-amplified DNA may be different from the unit definition derived from duplex oligos with a TelA site due to the different substrates.

TABLE 3

Variant TelA specific activity on RCA substrate

| TelA mutant | Specific activity on RCA-DNA (U/mg) | x-fold of enhanced activity |
|---|---|---|
| ΔN105/D97A (control) | 20,000 U/mg | 2 |
| WT (full-length, control) | 5,000-10,000 U/mg | 0.5-1 |
| ΔΔN105 | 5000 U/mg | 0.5 |
| ΔN105/D97K | 40,000 U/mg | 4 |
| ΔN105/D97R | 40,000-80,000 U/mg | 4-8 |
| ΔN105/D97K/E98D | 40,000 U/mg | 4 |

TABLE 3-continued

Variant TelA specific activity on RCA substrate

| TelA mutant | Specific activity on RCA-DNA (U/mg) | x-fold of enhanced activity |
|---|---|---|
| ΔN105/D97K/R100K | 40,000 U/mg | 4 |
| ΔN105/D97K/E98A | 80,000 U/mg | 8 |
| ΔN105/D97K/E98D/R100K | 10,000 U/mg | 1 |

The ΔN105/D97K/E98A variant performed the best under the conditions tested. The ΔN105/D97K/E98D/R100K variant did not show highly enhanced activity or accumulated effects of the component alterations.

Example 14: Activity of TelN and TelA Variants on RCA Amplified DNA

Figures 17A, 17B:
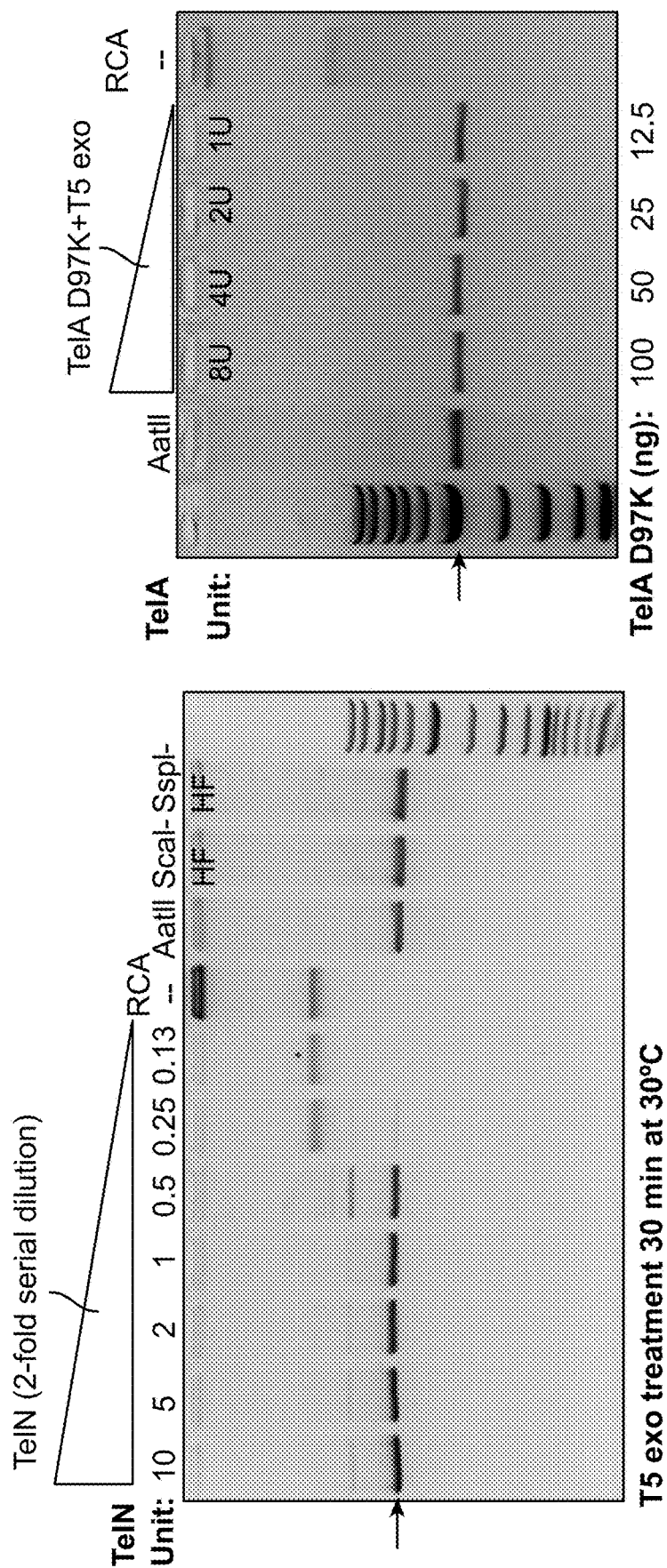
FIG. 17A shows results of an example protelomerase activity assay for TelN.
FIG. 17B shows results of an example protelomerase activity assay for variant TelA (ΔN105/D97K).

A protelomerase activity assay was performed in accordance with EXAMPLE 11 and results are shown in FIG. 17.

The plasmids containing TelA or TelN site was amplified in RCA by phi 29 DNA polymerase and random primer (8mer-phosphorothiate modified) and 1 μg RCA-amplified DNA was digested by ΔN105/D97K for pUC-TelA26 concatemers or digested by TelN for pUC-TelN54 concatemers. Figure x shows that TelN protelomerase has ~5 U/μl of enzyme by 2-fold serial dilutions (equivalent of 5 U/μl of the enzyme on linearized plasmid DNA with a single TelN site), which was calculated as 9,000 U/mg protein in term of specific activity (i.e. 1 μg TelN protein has approximately –9 U). TelA mutant ΔN105/D97K has 40,000 U/mg protein that displays 4.4× higher specific activity than TelN. TelA mutant ΔN105/D97K/E98A has approximately 80,000 U/mg protein that shows 8.9× higher specific activity than TelN, indicating a significant activity improvement. Unit definition of TelA mutant and TelN on RCA-amplified DNA: 1 unit of enzyme is defined as the amount of enzyme required to complete 95% telomere resolution (cleavage and ligation) of 1 μg of RCA amplified DNA in 30-60 min at 30° C. followed by T5 exonuclease treatment for 30 min at 30° C.

Comparison of TelN and variant TelA cleavage results allow specific activity to be determined. TelN digest condition (FIG. 17A): 1 ng RCA amplified DNA, 5 μL of 10× ThermoPol buffer, 1 μL of TelN (2-fold serial dilutions), 43 μL 10 mM Tris-HCl, at 30° C. for 30 min (the same digestion recommended by NEB (www.neb.com). 2 μL of T5 exonuclease (20 U) was added and incubation at 30° C. continued for 30 min. The reaction was terminated by addition of 10 IA of 5× stop dye and analyzed on a 0.8% agarose gel. The restriction digestions (AatII, ScaI-HF, SspI-HF) served as controls to linearize the concatemers. Prolonged TelN digestion for 60 min did not improve the digestion efficiency. TelA ΔN105/D97K digest condition (FIG. 17B): ΔN105/D97K digest for 60 min at 30° C., plus T5 exonuclease treatment for 30 min. 1 μg of RCA amplified DNA, 5 μL of 10× ThermoPol buffer, 1 μL of TelA ΔN105/D97K (12.5-100 ng), 43 μL 10 mM Tris-HCl, incubated in a small shaker with low-speed agitation at 30° C. for 60 min. The reaction was terminated by addition of 10 μL of 5× stop dye and the products were analyzed on a 0.8% agarose gel. The conclusion is that TelA mutant ΔN105/D97K has 40,000 U/mg protein that displays 4.4× higher specific activity than TelN.

Example 15: Activity of TelA Variants on RCA Amplified DNA

Figure 18:
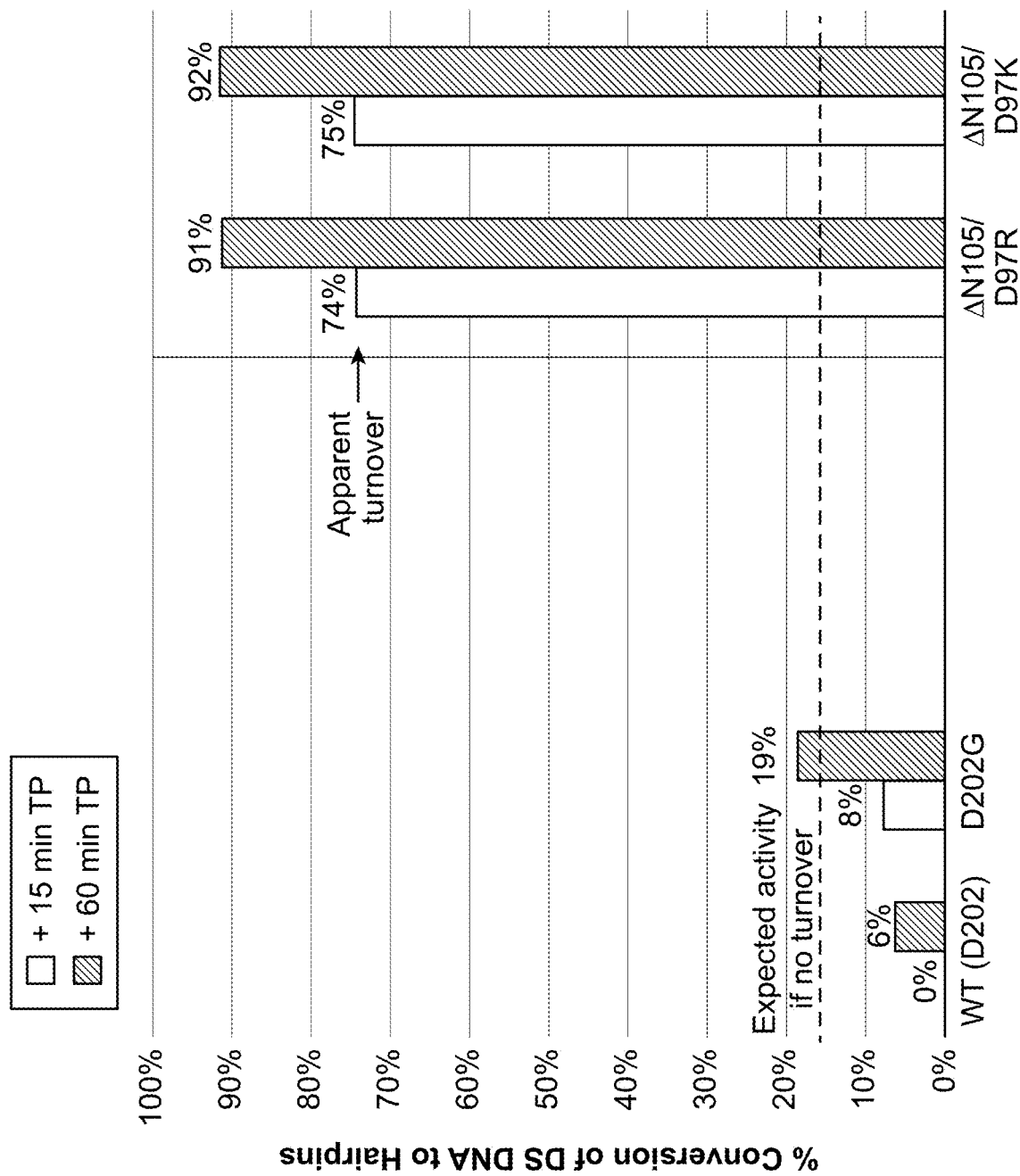
FIG. 18 shows example results of conversion of substrate (FAM-labeled linear dsDNA) to product (closed end hairpin) by WT TelA (D202) and TelA variants (D202G; ΔN105/D97R; ΔN105/D97K).

Protelomerase activity assay reactions (50 μL) were performed in ThermoPol buffer with a linear oligo nucleotide set comprising SEQ ID NO:16 and incubated at 30° C. for 15 or 60 minutes, quenched, diluted, and resolved by capillary electrophoresis. Results are shown in FIG. 18. Substrate was provided in excess (6:1) over the enzyme and the dotted line shows the expected % product formation if the reaction is stoichiometric. Higher % conversion by the ΔN105/D97R, ΔN105/D97K variants is consistent with enzyme turnover.

Example 16: Capacity of Variant TelA to Turnover

To estimate the turnover number of TelA and the selected D97 variants (ΔN105/D97K, ΔN105/D97N, and ΔN105/D97R), were set up by mixing limiting amount of enzyme with excess substrate (as described in EXAMPLE 15) at a concentration series. The turnover number is defined by the ratio of product amount over 0.5× of the protein amount (as dimeric TelA protein is required to bind each inverted-repeat target site to form two different hairpin products, in which one is monitored here). In a total of 50 μl reaction, 25 nM of TelA or the engineered variants N105Δ/D97K, N105Δ/D97N, or N105Δ/D97R were reacted with the duplex oligo target (78-bp oligo set3 with a 26 bp target site) at 25 nM, 50 nM, 100 nM, and 200 nM final concentration in 1× ThermoPol buffer. The reactions were started by addition of the enzyme and incubated at 30° C. An aliquot of 5 μl was removed and thoroughly mixed with 5 μl of 2% (w/v) SDS stop solution at specific time points: 1 min, 10 min, 30 min, 1 h, 2 h, 3 h, 4 h, and overnight (~20 h) to follow the reaction progression. All the reactions were then diluted to a final of ~5 nM with water and analyzed by CE.

Figure 19B:
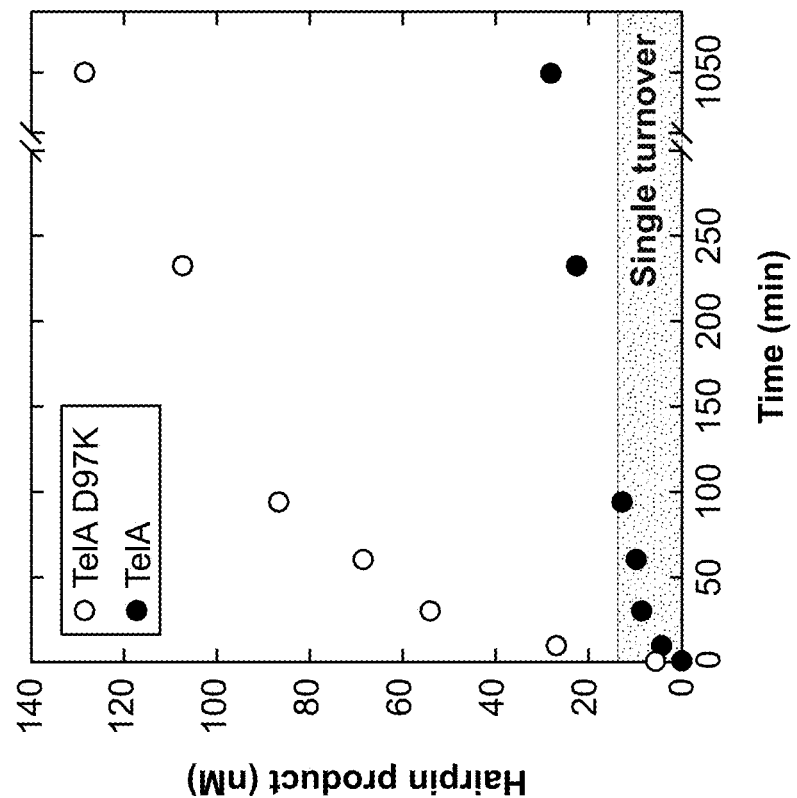
FIG. 19A and FIG. 19B show the results of a protelomerase assay in which a limiting amount of enzyme (25 nM final) was incubated with an excess of linear substrate (25 nM, 50 nM, 100 nM, or 200 nM final) in ThermoPol buffer at 30° C. overnight and turnover numbers were calculated by dividing the concentration of hairpin product by half the concentration of enzyme (as each reaction is catalyzed by an enzyme homodimer).
Figure 19A:
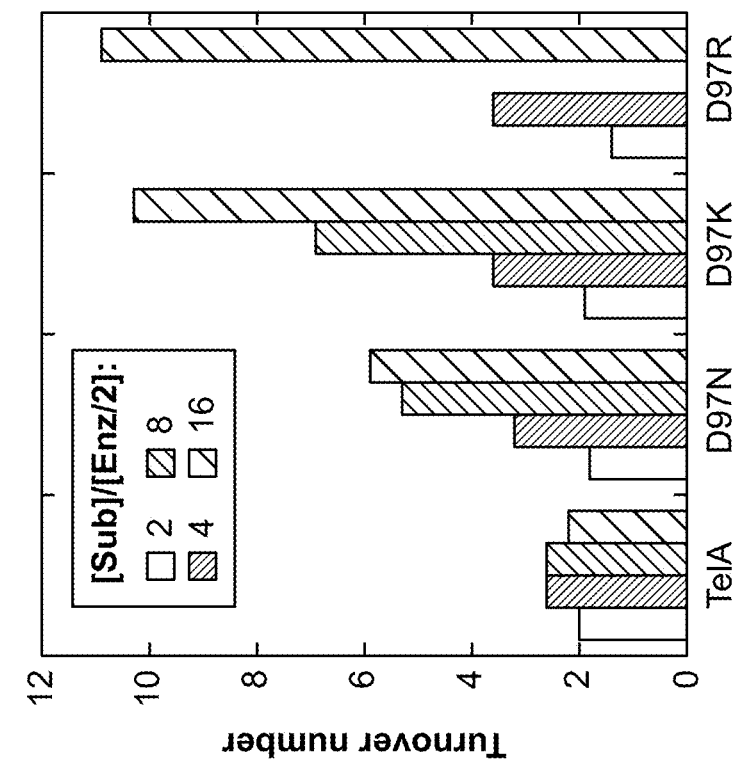

Turnover numbers were calculated by dividing the concentration of hairpin product by half the concentration of enzyme (as each reaction is catalyzed by an enzyme homodimer). Results shown in FIG. 19A indicate that the TelA variant enzymes, ΔN105/D97K, ΔN105/D97N, and ΔN105/D97R, showed higher turnover numbers than wild-type TelA under conditions with various ratios of substrate to enzyme. The assay was repeated with just the 200 nM substrate concentration and wild-type and variant TelA. Product formation was monitored over time. Aliquots of each reaction were removed and quenched with 1% final SDS solution at different time points to check the progression of the reaction. Results shown in FIG. 19B indicate that ΔN105/D97K catalyzes hairpin formation faster than wild-type TelA, as well as more turnovers (~10 times vs ~2 times).

Example 17: A TelA Variant (ΔN105/D97K) is Faster than Wild-Type TelA

Figure 20:
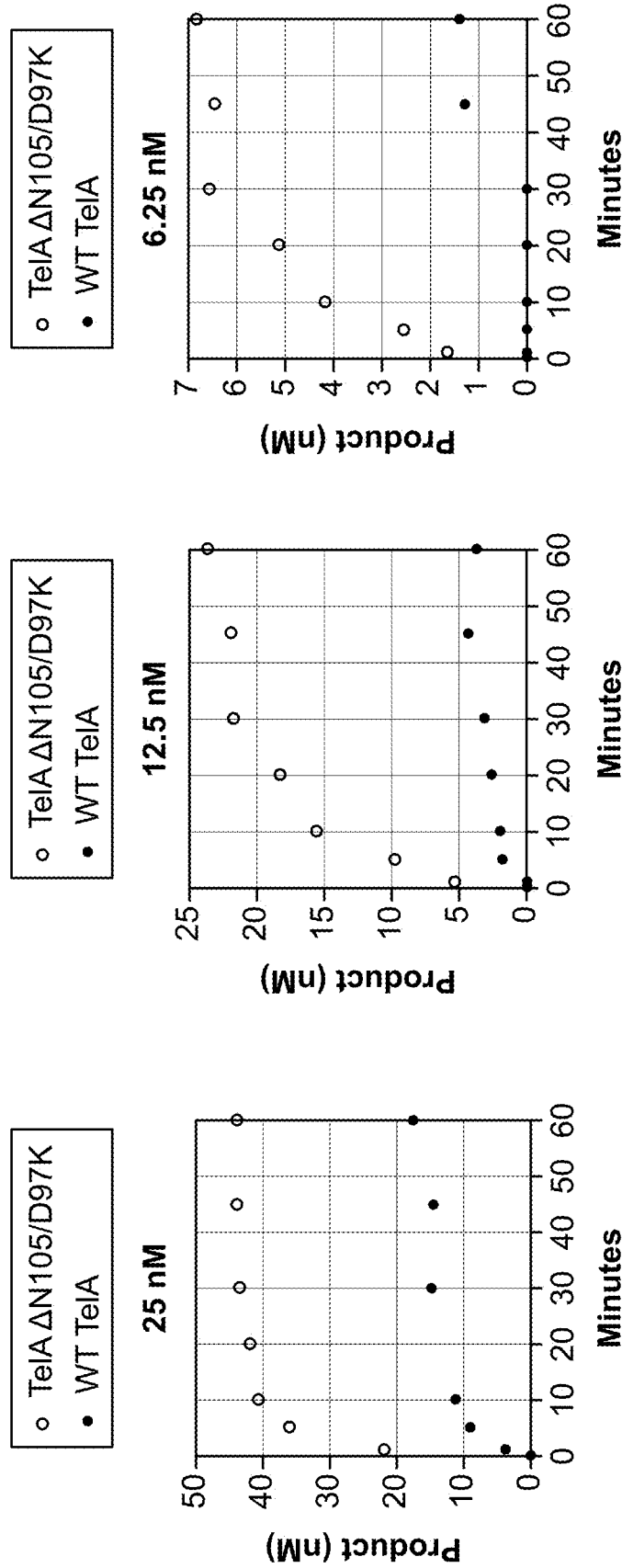
FIG. 20 shows results of an example protelomerase activity assay of wild type (filled circles) and variant TelA (open circles) at three serial dilutions of enzyme (25 nM, 12.5 nM, and 6.25 nM) incubated with FAM-labeled TelA DNA substrates (50 nM).

A protelomerase activity assay was performed in accordance with EXAMPLE 11 and results are shown in FIG. 20. Briefly, wild-type TelA and TelA ΔN105/D97K enzymes (each at (monomer) concentrations of 6.25 nM, 12.5 nM or 25 nM) were incubated with FAM-labeled TelA DNA substrates (50 nM) in 1× ThermoPol Buffer at 37° C. Reaction aliquots (10 μl) were sampled and reactions halted by the addition of 1% SDS at 0, 2, 5, 10, 20, 30, 45, and 60 minutes. Reactions were separated and analyzed by capillary electrophoresis using an ABI3730 xL DNA analyzer. Cleaved product (nM) was plotted versus time (FIG. 20). Wild-type TelA (filled circles) substrate cleavage is slower than TelA ΔN105/D97K (open circles). Almost 7 nM product was formed by the variant TelA at 6.25 nM (i.e., 3.125 nM homodimer), almost 25 nM product was formed by the variant TelA at 12.5 nM (i.e., 6.25 nM homodimer), and almost 45 nM product was formed by the variant TelA at 25 nM (i.e., 12.5 nM homodimer).

Example 18: Size Fractionation of His-Tagged TelA Variants

Figure 21:
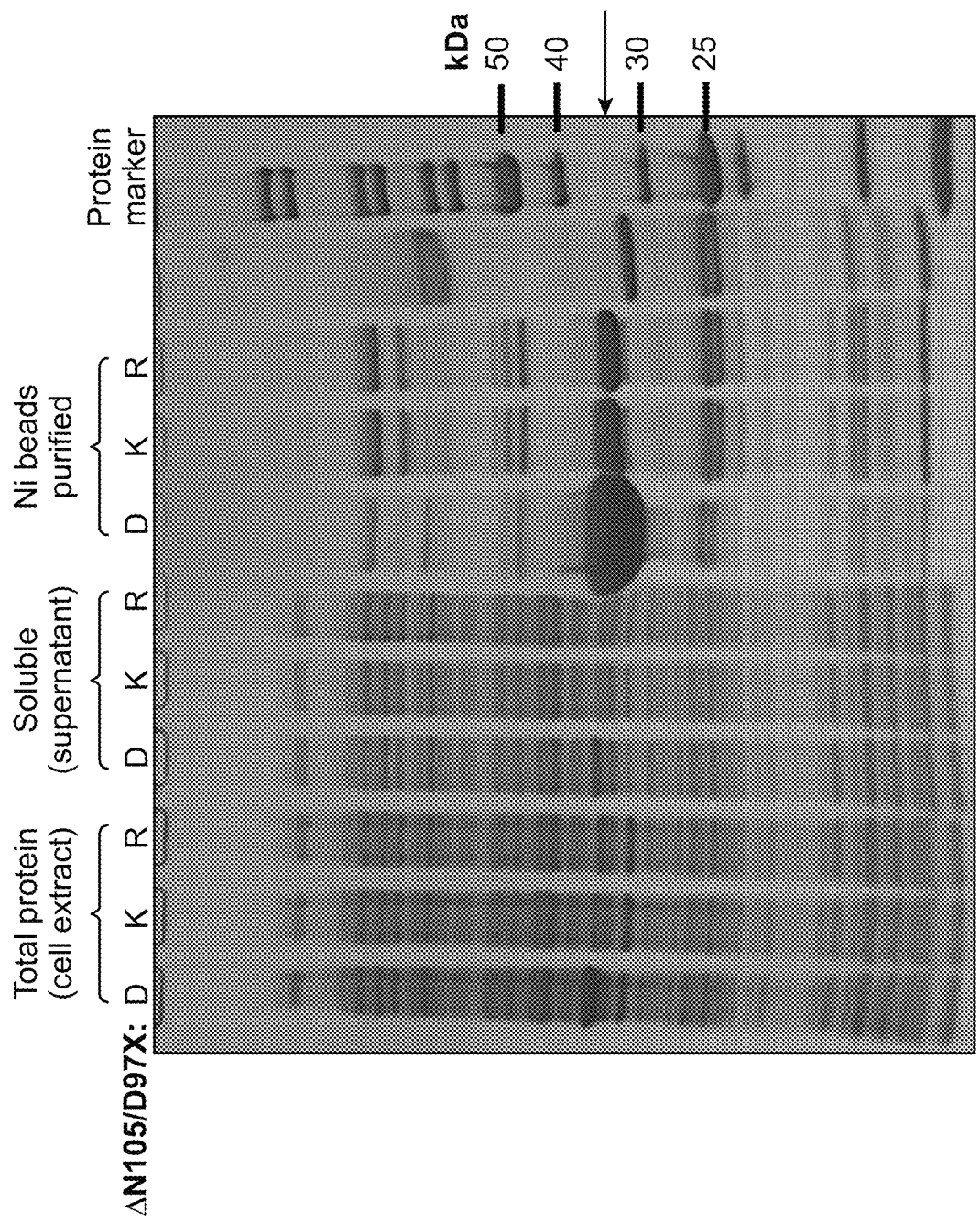
FIG. 21 shows SDS-PAGE fractionation of partially purified example TelA variants. Each lane marked "D" included a variant TelA in which the 105 N-terminal amino acid residues are deleted and replaced with a methionine (M) residue, an 8-residue His tag, and an SG linker (SEQ ID NO:14). Each lane marked "K" included a variant TelA having this N-terminal deletion/replacement and a single amino acid substitution D97K (SEQ ID NO:7). Each lane marked "R" included a variant TelA having this N-terminal deletion/replacement and a single amino acid substitution D97R (SEQ ID NO:8). Predicted molecular weight of these variants was 39.6 kDa while the apparent molecule weight on the gel was 35 kDa (arrow).

Variants evaluated in EXAMPLES 18-23 included C-terminal His tags. Cells expressing one of three N-terminally tagged TelA variants (SEQ ID NOS:7, 8, and 23) were grown to mid-log phase and IPTG was added to 0.5 mM for induction at 18° C. overnight. Induced cultures were spun and supernatants subjected to Ni bead purification of the 8×His tagged proteins in accordance with EXAMPLE 1. 1 μL of total protein or soluble supernatant was loaded in each lane to see induction and assess purity and yield. Results are shown in FIG. 21.

Figure 22:
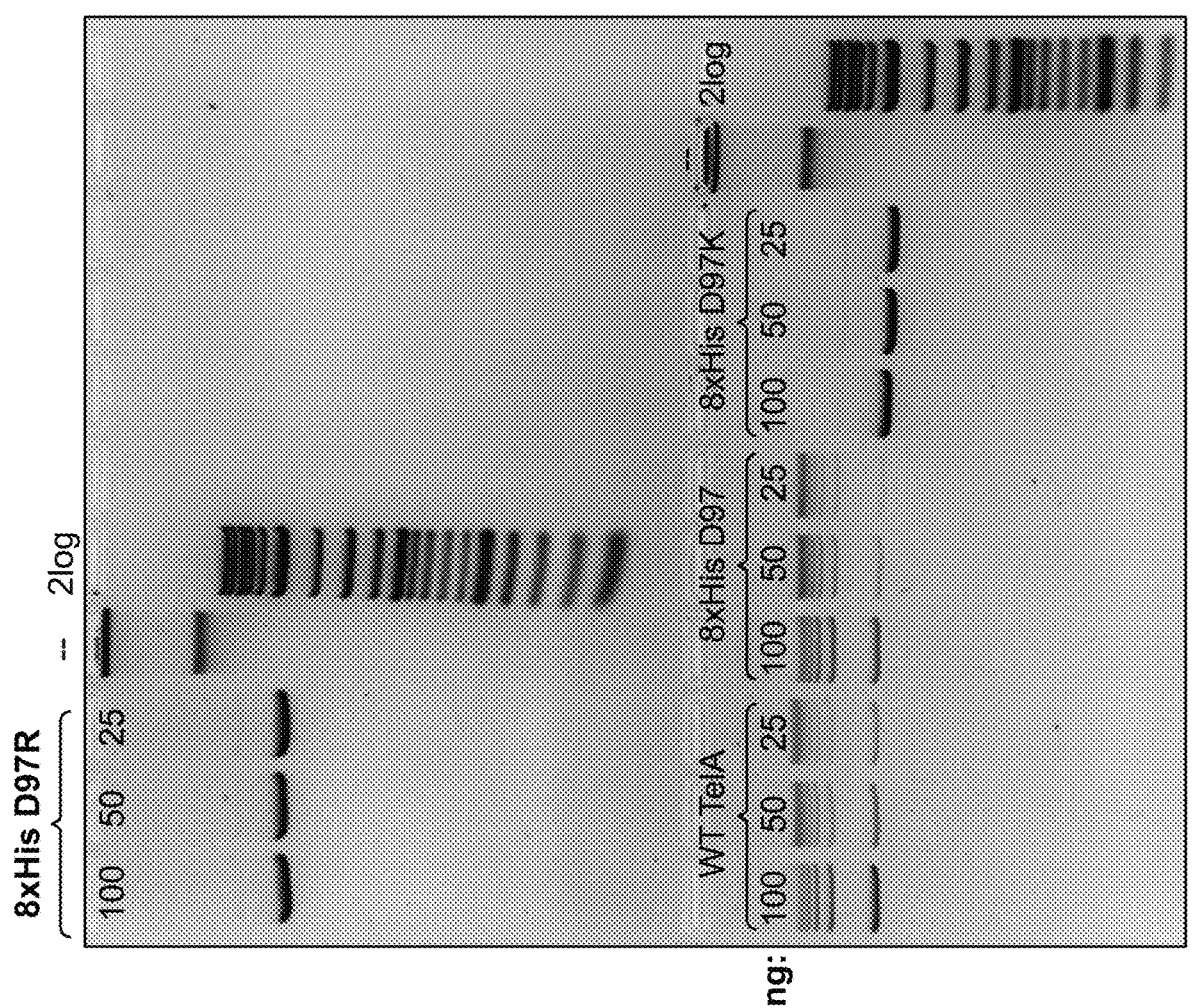
FIG. 22 shows results of an example protelomerase activity assay for the variants shown in FIG. 21.

Example 19: Hairpin Resolution Activity of Partially Purified His-Tagged TelA Variants Hairpin resolution activity of partially purified TelA variants of EXAMPLE 1 was assessed. RCA-amplified DNA having a TelA target site (2 μg) in a storage buffer was incubated with 100 ng, 50 ng, or 25 ng of protein at 37° C. for an hour in 1× ThermoPol buffer. T5 exonuclease (20 units in 2 μL) were added and reactions were incubated for 30 minutes at 37° C. Gel loading dye was added and reaction products were size fractionated on 1% agarose gel by electrophoresis. Results are shown in FIG. 22. His-tagged ΔN105/D97K (SEQ ID NO:7) and D97R (SEQ ID NO:8) display activity at least 4× higher than full-length WT and D97 (SEQ ID NO:23).

Figure 23:
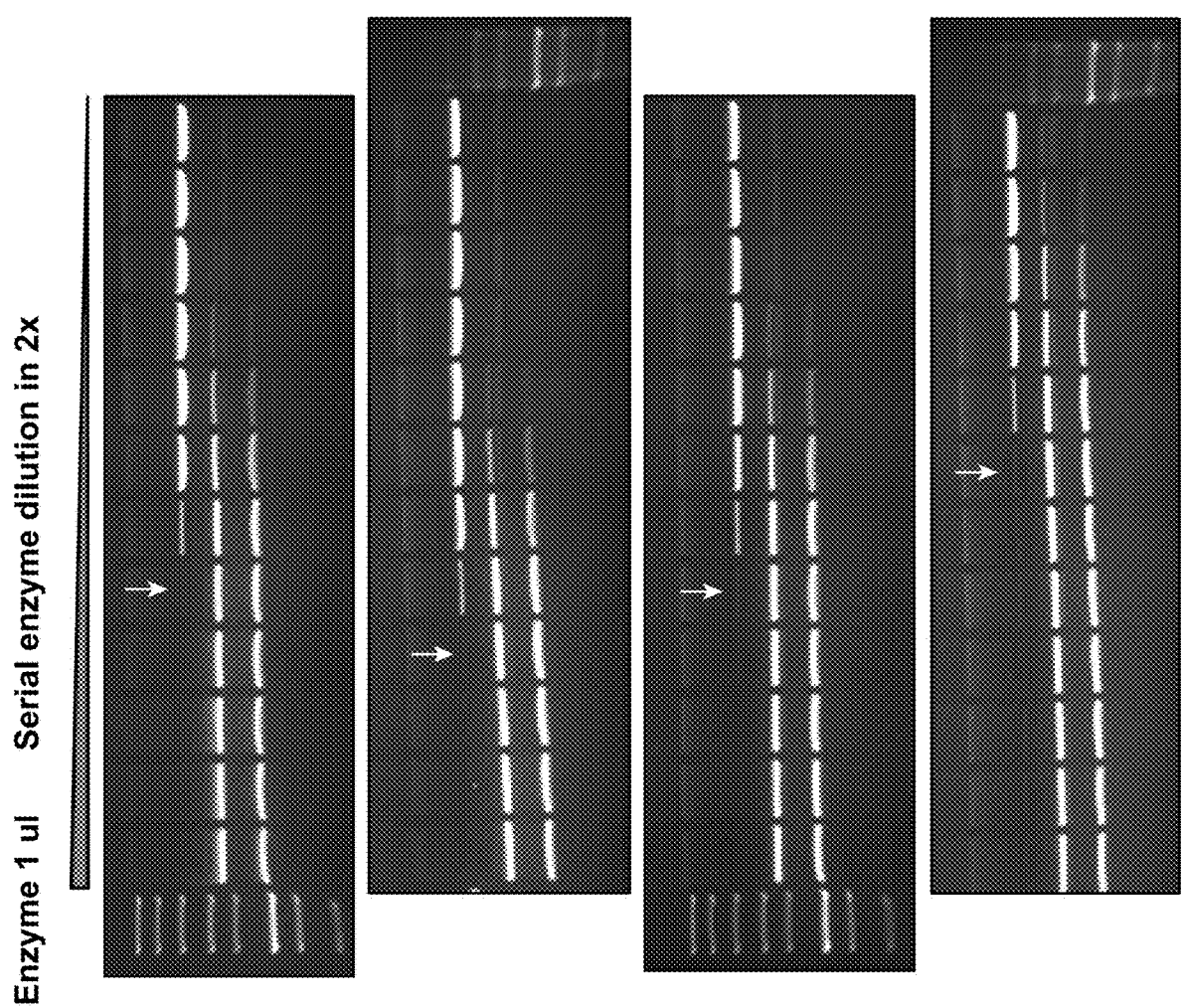
FIG. 23 shows results of an example protelomerase activity assay of wild type (WT; top panel) and TelA variant D97A (second panel from top), TelA variant ΔN105/D97A (third panel from top), and TelA variant ΔN105/D97K (bottom panel) with a linear pMT26 DNA substrate. Arrows indicate that the amounts of enzyme needed for conversion of at least 90% of initial substrates (L, 0.15 μmol) to product (P), namely 318 ng for WT, 90 ng for TelA (202A), 28.75 ng for ΔN-TelA(D97A), and 10.63 ng for ΔN-TelA(D97K). These results suggest ΔN-TelA(D97K) has the highest specific activity among all constructs of TelA tested.

Example 20: D97K Cleavage Efficiency and Specific Activity Vs Wild Type and D97A Specific activities of variant TelA constructs (WT, D202A, ΔN105/D97A and ΔN105/D97K) were determined using linear DNA pMT26 as the substrate. Results are shown in FIG. 23. Reactions loaded into lane 1 of each panel included 1 μL of each of the indicated enzymes at the indicated concentrations (TABLE 4) followed by 2-fold serial dilutions from left to right. Arrows indicate that the amount of enzymes needed for conversion of at least 90% of initial substrates (L, 0.15 μmol) to products (P). Reactions were setup in a 50 μL with ThermPol buffer supplemented with a detergent and amino acid salt at 30° C. for 30 min. As shown in FIG. 23, the amounts of each enzyme needed were 318 ng of WT-TelA, 90 ng TelA D202A, 28.75 ng ΔN105/D97A, and 10.63 ng ΔN105/D97K to complete 90% of substrate conversion to product. Accordingly, TelA variant ΔN105/D97K displayed the highest specific activity under the conditions tested.

TABLE 4

| Enzyme | Minimum amount of enzyme required to completely digest linear DNA |
|---|---|
| Wild Type (full length) (5100 μg/mL) | 318 ng |
| Variant TelA (full length with D202A substitution) (730 μg/mL) | 90 ng |
| Variant ΔN105/D97A (460 μg/mL) | 28.75 ng |
| Variant ΔN105/D97K (680 μg/mL) | 10.63 ng |

What is claimed is:

1. A variant protelomerase capable of cleaving and rejoining a polynucleotide comprising a nucleotide sequence according to SEQ ID NO:16 and having a turnover number≥1.1, wherein the variant protelomerase comprises an amino acid sequence having at least 95% identity to SEQ ID NO:1 and having the following properties:
   (a) X1 is T, M-T or M-$H_8$-S-G-T;
   (b) X97 is K or R;
   (c) X98 is A; and
   (d) X337 is G or G-$H_6$,
   provided that if X1 is M-$H_8$-S-G-T, X337 is G and if X337 is G-$H_6$, X1 is T or M-T.

2. A variant protelomerase according to claim 1, wherein the amino acid sequence further has the following additional properties:
   (e) Y96 is Y;
   (f) R100 is R;
   (g) R101 is R; and
   (h) K103 is K.

3. A variant protelomerase according to claim 1, wherein the amino acid sequence has (a) X1 is M-T, (b) X97 is K or R, and (d) X337 is G.

4. A variant protelomerase according to claim 1, wherein the amino acid sequence has (a) X1 is M-$H_8$-S-G-T, (b) X97 is K or R, and (d) X337 is G.

5. A variant protelomerase according to claim 1, wherein the amino acid sequence has (a) X1 is M-T, (b) X97 is K or R, and (d) X337 is G-$H_6$.

6. A variant protelomerase according to claim 1, wherein the amino acid sequence has at least 97% identity to SEQ ID NO:1.

7. A composition comprising:
   a variant protelomerase according to claim 1; and
   a buffer.

8. A composition according to claim 7, wherein the buffer is a storage buffer or a reaction buffer.

9. A composition according to claim 7 further comprising a salt, a protein, a stabilizer, a detergent, a polyanion, a polynucleotide, a cell, a biological fluid or secretion, an aptamer, a pH indicator, a crowding agent, a sugar, a starch, cellulose, a glass-forming agent, a lipid, an oil, aqueous media, a support, or any combination thereof.

10. A composition according to claim 9, wherein the salt comprises NaCl, $MgCl_2$, $MnCl_2$, $CaCl_2$, an amino acid salt or any combination thereof.

11. A composition according to claim 9, wherein the detergent is selected from an ionic detergent, a non-ionic detergent, and a zwitterionic detergent.

12. A composition according to claim 9, wherein the polynucleotide is a variant TelA DNA substrate having a nucleotide sequence comprising at least one copy of SEQ ID NO:16.

13. A composition according to claim 7 further comprising propanediol, betaine, $CaCl_2$, NaCl, KCl, potassium glutamate, poloxamer, octoxinol-9, polysorbate20, or combinations thereof.

14. A kit comprising:
   a variant protelomerase according to claim 1; and
   a buffer.

15. A kit according to claim 14, wherein the buffer is a storage buffer or a reaction buffer.

16. A kit according to claim 14 further comprising a salt, a protein, a stabilizer, a detergent, a polyanion, a polynucleotide, a cell, a biological fluid or secretion, an aptamer, a pH indicator, a crowding agent, a sugar, a starch, cellulose, a glass-forming agent, a lipid, an oil, aqueous media, a support, or any combination thereof.

17. A kit according to claim 16, wherein the salt comprises NaCl, $MgCl_2$, $MnCl_2$, $CaCl_2$, an amino acid salt or any combination thereof.

18. A kit according to claim 16, wherein the detergent is selected from an ionic detergent, a non-ionic detergent, and a zwitterionic detergent.

19. A kit according to claim 14, wherein the variant protelomerase and the buffer are in separate containers.

20. A kit according to claim 16, wherein the polynucleotide is an adapter.

21. A kit according to claim 16, wherein the polynucleotide is a variant protelomerase DNA substrate having a nucleotide sequence comprising at least one copy of SEQ ID NO:16.

* * * * *